US011781116B2

(12) United States Patent
Feary et al.

(10) Patent No.: US 11,781,116 B2
(45) Date of Patent: Oct. 10, 2023

(54) MAMMALIAN CELLS FOR PRODUCING ADENO-ASSOCIATED VIRUSES

(71) Applicant: LONZA LTD., Visp (CH)

(72) Inventors: Marc Feary, Suffolk (GB); Robert J. Young, London (GB); Anandita Seth, Sugar Land, TX (US)

(73) Assignee: LONZA LTD., Visp (CH)

( * ) Notice: Subject to any disclaimer, the term of this patent is extended or adjusted under 35 U.S.C. 154(b) by 812 days.

(21) Appl. No.: 16/486,360

(22) PCT Filed: Feb. 17, 2018

(86) PCT No.: PCT/IB2018/000239
§ 371 (c)(1),
(2) Date: Aug. 15, 2019

(87) PCT Pub. No.: WO2018/150271
PCT Pub. Date: Aug. 23, 2018

(65) Prior Publication Data
US 2020/0002682 A1    Jan. 2, 2020

Related U.S. Application Data

(60) Provisional application No. 62/460,457, filed on Feb. 17, 2017.

(51) Int. Cl.
C12N 15/86     (2006.01)
C12N 7/00      (2006.01)
C12N 15/90     (2006.01)

(52) U.S. Cl.
CPC ............. *C12N 7/00* (2013.01); *C12N 15/86* (2013.01); *C12N 15/90* (2013.01); *C12N 2750/14143* (2013.01); *C12N 2750/14152* (2013.01); *C12N 2800/30* (2013.01)

(58) Field of Classification Search
CPC ..................................................... C12N 15/86
See application file for complete search history.

(56) References Cited

U.S. PATENT DOCUMENTS

| | | | |
|---|---|---|---|
| 5,190,871 A | 3/1993 | Cox et al. |
| 5,656,491 A | 8/1997 | Cassani et al. |
| 5,658,776 A | 8/1997 | Flotte et al. |
| 5,837,484 A | 11/1998 | Trempe et al. |
| 6,033,885 A | 3/2000 | Latta et al. |
| 7,074,618 B2 | 7/2006 | Li et al. |
| 7,094,604 B2 | 8/2006 | Snyder et al. |
| 7,629,167 B2 | 12/2009 | Hodge et al. |
| 7,771,997 B2 | 8/2010 | Chen et al. |
| 8,236,293 B2 | 8/2012 | Fallaux et al. |
| 8,298,054 B2 | 10/2012 | Hodge et al. |
| 9,422,576 B2 | 8/2016 | Nishie et al. |
| 10,072,250 B2 | 9/2018 | Sakamoto et al. |
| 10,280,436 B2 | 5/2019 | Rance et al. |
| 2004/0087026 A1 | 5/2004 | Bertran et al. |
| 2004/0219516 A1 | 11/2004 | Bennett et al. |
| 2009/0305626 A1 | 12/2009 | Hope |
| 2011/0280797 A1 | 11/2011 | Mohtadi et al. |
| 2012/0077429 A1 | 3/2012 | Wernimont et al. |
| 2013/0280797 A1 | 10/2013 | Rao et al. |
| 2014/0127162 A1 | 5/2014 | Balazs et al. |
| 2016/0097074 A1 | 4/2016 | Collins et al. |

FOREIGN PATENT DOCUMENTS

| | | | | |
|---|---|---|---|---|
| EP | 2711428 A1 | 3/2014 | | |
| WO | 98/27207 A1 | 6/1998 | | |
| WO | 2013/190032 A1 | 12/2013 | | |
| WO | WO-2013190032 A1 * | 12/2013 | ............. | C07K 16/00 |
| WO | 2015/018703 A1 | 2/2015 | | |
| WO | 2015/031686 A1 | 3/2015 | | |
| WO | WO-2015031686 A1 * | 3/2015 | ............. | C12N 15/86 |

OTHER PUBLICATIONS

NCBI Printout NL1 locus sequence (Year: 2020).*
NCBI Printout NL2 locus sequence (Year: 2020).*
Argos et al., "The integrase family of site-specific recombinases: regional similarities and global diversity," EMBO J 5:433 (1986).
Bandaranayake et al., "Recent advances in mammalian protein production," Federation of European Biochemical Societies Letters 588(2):253-260 (2014).
Bannam et al., "Molecular genetics of the chloramphenicol-resistance transposon Tn4451 from Clostridium perfringens: the TnpX site-specific recombinase excises a circular transposon molecule.," Mol Microbiol 16:535-551 (1995).
Baser et al., "A method for specifically targeting two independent genomic integration sites for co-expression of genes in CHO cells," Methods 95:3-12 (2015).
Birch et al., "Antibody production," Adv Drug Delivery Rev, 58:671-685 (2006).
Carrasco et al., "Anabaena xisF gene encodes a developmentally regulated site-specific recombinase," Genes Dev 8:74-83 (1994).
Crellin et al., "The resolvase/invertase domain of the site-specific recombinase TnpX is functional and recognizes a target sequence that resembles the junction of the circular form of the Clostridium perfringens transposon Tn4451," J Bacteriol 179:5148-5156 (1997).
De Vries et al., "Increased virus replication in mammalian cells by blocking intracellular innate defense responses," Gene Ther 15:545-552 (2008).
Graham et al., "Characteristics of a human cell line transformed by DNA from human adenovirus type 5," J Gen Virol 36:59-74 (1977).
Kotin, "Prospects for the use of adeno-associated virus as a vector for human gene therapy," Human Gene Therapy 5:793-801 (1994).

(Continued)

*Primary Examiner* — Anoop K Singh
*Assistant Examiner* — David A Montanari
(74) *Attorney, Agent, or Firm* — MEDLER FERRO WOODHOUSE & MILLS PLLC

(57) ABSTRACT

A mammalian cell comprising at least four distinct recombination target sites (RTS), an adenovirus (Ad) gene comprising E1A, E1B or a combination thereof, and a promoter operatively linked to the Ad gene, wherein the RTS, the Ad gene, and the promoter are chromosomally-integrated; methods for using the cell for generating a recombinant adeno-associated virus (rAAV) producer host cell; and methods for using the AAV producer host cell to produce, package and purify rAAV.

12 Claims, 21 Drawing Sheets

Specification includes a Sequence Listing.

(56) References Cited

OTHER PUBLICATIONS

Kuhstoss et al., "Analysis of the integration function of the streptomycete bacteriophage phi C31," J Mol Biol 222:897-890 (1991).
Louis et al., "Cloning and Sequencing of the Cellular-Viral Junctions from the Human Adenovirus Type 5 Transformed 293 Cell Line," Virology 233:423-429 (1997).
Low et al., "Stabilization of the p53 tumor suppressor is induced by adenovirus 5 E1A and accompanies apoptosis," Genes Dev 7:535-545 (1993).
Matsuura et al., "The sre gene (ORF469) encodes a site-specific recombinase responsible for integration of the R4 phage genome," J Bacteriol 178:3374-3376 (1996).
Muzyczka, "Use of adeno-associated virus as a general transduction vector for mammalian cells," Current Topics in Microbiol and Immunol 158:97-129 (1992).
Ow et al., "Conditionally replicating plasmid vectors that can integrate into the Klebsiella pneumoniae chromosome via bacteriophage P4 site-specific recombination," J Bacteriol 155:704-713 (1983).
Porter et al., "Strategies for selecting recombinant CHO cell lines for cGMP manufacturing: improving the efficiency of cell line generation," Biotechnol Prog 26:1455-1464 (2010).
Qiao et al., "Feasibility of generating adeno-associated virus packaging cell lines containing inducible adenovirus helper genes," J Virol 76:1904-1913 (2002).
Robert et al., "Manufacturing of recombinant adeno-associated viruses using mammalian expression platforms," Biotechnology Journal 12(3):1600193 (2017).
Samulski et al., "AAV-Mediated Gene Therapy for Research and Therapeutic Purposes," Annu Rev Virol 1:427-451 (2014).
Sanber et al., "Construction of stable packaging cell lines for clinical lentiviral vector production," Scientific Reports 5(1):1-74 (2015).
Sato et al., "The cisA cistron of Bacillus subtilis sporulation gene spoIVC encodes a protein homologous to a site-specific recombinase," J Bacteriol 172:1092-1098 (1990).
Sauer, "Functional expression of the cre-lox site-specific recombination system in the yeast Saccharomyces cerevisiae," Mol Cell Biol 7:2087-2096 (1987).
Sauer et al., "Site-specific DNA recombination in mammalian cells by the Cre recombinase of bacteriophage P1," Proc Natl Acad Sci USA 85:5166-5170 (1988).
Stragier et al., "Chromosomal rearrangement generating a composite gene for a developmental transcription factor," Science 243:507-512 (1989).
Strathdee et al., "Expression of Transgenes Targeted to the Gt(ROSA) 26or Locus is Orientation Dependent," PLOS One 1:e4 (2006).
Thorpe et al., "In vitro site-specific integration of bacteriophage DNA catalyzed by a recombinase of the resolvase/invertase family," Proc Natl Acad Sci USA, 95:5505-5510 (1998).
Tjio et al., "Genetics of Somatic Mammalian Cells," Exp Med 108:259-268 (1958).
Turan et al., "Multiplexing RMCE: Versatile Extensions of the Flp-Recombinase-Mediated Cassette-Exchange Technology," Journal of Molecular Biology 402(1):52-69 (2010).
Wirth et al., "Road to precision: recombinase-based targeting technologies for genome engineering," Curr Opin Biotech 18:411-419 (2007).
International Search Report issued in International Application No. PCT/IB2018/000239, dated Jul. 27, 2018.
Koichi Miyake et al., Journal of the Japanese Medical University, 2012, 8(2): 150-156. (English abstract provided).

* cited by examiner

Figure 2: pMF30.

Figure 3: pMF23.

Figure 4: pXC17.4_17Ad5PerProKZ

Figure 20. Titers of rAAV2.GFP from HEK293 and CHO cells

| | 1# | 2# | 3# | 4# | 5# |
|---|---|---|---|---|---|
| HEK293 | | | pHelper | | |
| CHOK1SV GS-KO | | | wt Ad5 (500 MOI) | | |
| Rep-Cap vector | pLMC32 | pLMC33 | pLMC34 | pLMC35 | pRC2-mi342 |
| GOI vector | | pLMC31 | | | pAAV-GFP |
| Titer/HEK293(vg/ml) | 4.9E+09 | 2.9E+09 | 2.9E+09 | 2.2E+09 | 8.4E+08 |
| Titer/CHO (vg/ml) | 1.4E+07 | 1.3E+07 | 1.8E+07 | 2.3E+07 | 3.7E+07 |

Figure 21. Primer sequences for TaqMan-qPCR and PCR analysis

| Oligo Name | Sequence (5' to 3') |
|---|---|
| Rep-Cap-P1-F | TTTGGGACGTTTCCTGAGTC |
| Rep-Cap-P1-R | CTCATCCACCACCTTGTTCC |
| Rep-Cap-P2-F | GCAAGACCGGATGTTCAAAT |
| Rep-Cap-P2-R | CCTCAACCACGTGATCCTTT |
| Rep-Cap-P3-F | CTGCAGACAATGCGAGAGAA |
| Rep-Cap-P3-R | CGACAGAAACGGGTTGAGAT |
| Rep-Cap-P4-F | GAGTGACATTCGGGACCAGT |
| Rep-Cap-P4-R | GTCTCTGCCATTGAGGTGGT |
| E1A-F | GAGGACCTGTGGCATGTTTG |
| E1A-R | CATTTTAGGACGGCGGGTAG |
| E1B-19K-F | GAAGTCCTGTGGTGAGCTGT |
| E1B-19K-R | TGGCCAGAAAATCCAGCAGG |
| E1B-55K-F | CTGGAAGGTGCTGAGGTACG |
| E1B-55K-R | CTCAGCTCCTCGGTCACATC |
| E2A-F | CTTTGGTAGCTGCCTTCCCA |
| E2A-R | GTATCCTAACGCCCAGACCG |
| E4-F | TAATAAACTCCCCGGGCAGC |
| E4-R | ACAACGCGTGGACTTCTC |
| VAI-F | CACTCTTCCGTGGTCTGGTG |
| VAI-R | GTTGTCTGACGTCGCACAC |
| VAII-F | TTTCCAAGGGTTGAGTCGCA |
| VAII-R | GAATTTGCAAGCGGGGTCTT |
| Actin-F | CGACATCCGCAAAGACCTCT |
| Actin-R | AGGATGCTTAGCTCACCTTGA |
| Fer1L4 with Rep-Cap integrated-P5-F | GGAGTTCAAAGCCAGCTTATACCAACATG |
| Fer1L4 with Rep-Cap integrated-P5-R | GCTAAAGTTGGTATGGCAGCCTGCACC |
| Fer1L4 landing pad-P6-F | GGATCACTCTCGGCATGGACGAG |
| Fer1L4 landing pad-P6-R | CCTCTTCTTCAGCCACAGTCACTTC |
| NL1 with GOI integrated-P7-F | GCAGCACGAACAAGAGTCAC |
| NL1 with GOI integrated-P7-R | GAACCTGCGTGCAATCCATC |
| NL1 landing pad-P8-F | GGACATATCTGGGTGAAGGGAGCTG |
| NL1 landing pad-P8-R | CAGCCGCACGGTAGGCTTGTACTCGGTCAT |

MAMMALIAN CELLS FOR PRODUCING ADENO-ASSOCIATED VIRUSES

SEQUENCE LISTING

The instant application contains a Sequence Listing which has been submitted electronically in ASCII format and is hereby incorporated by reference in its entirety. Said ASCII copy, created on Mar. 28, 2018, is named 0132-0025WO1_SL.txt and is 8,516,061 bytes in size.

FIELD OF THE INVENTION

The present disclosure relates to a mammalian cell comprising at least four distinct recombination target sites (RTS), an adenovirus (Ad) gene comprising E1A, E1B or a combination thereof, and a promoter operatively linked to the Ad gene, wherein the RTS, the Ad gene, and the promoter are chromosomally-integrated. The disclosure also relates to a method for using the cell to generate a recombinant adeno-associated virus (rAAV) producer cell and methods for using the rAAV producer cell to produce, package and purify rAAV without live helper virus.

BACKGROUND OF THE INVENTION

The use of recombinant adeno-associated virus (rAAV) is being aggressively pursued in clinical development to obtain long-lasting, efficient delivery of gene therapy products. Baculovirus-based platforms for rAAV production often require raw materials that can be variable and time consuming to generate. Triple transfection and transient expression in HEK293 can be limited by poor scalability. Existing scalable HeLa cell based producer cell line processes require wild-type (wt) adenovirus 5 (Ad5) as a helper virus, and clearance of helper virus in the final product is critical due to safety concerns. When constructing a cell line to produce rAAV, the gene of interest and ancillary helper genes can be either expressed transiently or integrated into the host chromosome. Conventional DNA transduction routes used for the modification of the cellular genome can be subject to unpredictable alterations and are not easily inter changeable to adjust for the differing requirements of virus serotypes.

Therapeutic recombinant adeno-associated virus (AAV) constructs are replication defective and require co-infection of wt adenovirus (Ad) for replication and subsequent rounds of infection. Generation of therapeutic recombinant adeno-associated virus (rAAV) vectors generally requires three different components be supplied to the host: (i) the adeno-associated virus genes Rep/Cap that provide replication and packaging elements, (ii) the helper virus functions from Ad genome for virus packaging, and (iii) a gene of interest (GOI) of interest located between 3' and 5' AAV inverted terminal repeat sequences (ITR). The Ad genes required for efficient gene expression, DNA replication and packaging are thought to include E1A, E1B, E2A, E4 and VA RNA. E1A is proposed to be the earliest gene product made during Ad infection (Shenk, T. et al., Fields Virology, $3^{rd}$ ed., 2211-2148 (1996)). E1A is believed to act as a cue to begin virus replication by up-regulating transcription from the AAV Rep gene promoters, p5 and p19 and by activating early adenovirus promoters for E1B, E2A and E4. E1A is also believed to be used to drive the host cells into the S-phase of the cell cycle for viral DNA replication as the AAV encoded proteins (Rep and Cap) are not capable of this function. An adverse effect of EA is that it stabilizes p53, which leads to apoptosis (Low et al., Genes & Dev. 7:535-545 (1993)). Leaky expression of E1A can turn on Ad genes as well as the AAV Rep gene. The latter is reported to be cytostatic and cytotoxic, making it difficult to obtain a stable cell line from cells that constitutively express E1A. Regulated E1A gene expression appears to be critical to the success of a helper virus free AAV packaging cell line.

Different cell lines and different approaches to bringing these elements together to produce rAAV have been attempted. These different cell lines include HEK293 and HeLa cell lines. The different approaches have also included the use of the baculovirus system. However, each cell line and approach has its drawbacks and none is an ideal platform for scalable, robust rAAV production process.

One rAAV production process includes HEK293 cells, which were generated by transfection of primary embryonic kidney cells using physically sheared Ad5 DNA (Graham F. L. et al., J. Gen. Virol. 36:59-74 (1977)). Genomic analysis reportedly demonstrated that HEK293 cells carry an integrated fragment of the left-hand end of the adenovirus genome (bases 1-4344), containing the E1 region and additional flanking sequences (Louis N. et al, Virology 233:423-9 (1997)). Some triple-transfection processes have used adherent HEK293 cells for transfection with plasmids containing the remaining essential elements. Although using HEK293 in rAAV production is possible, an adherent cell based process in not scalable to meet the increasing vector needs for various indications and relies on transient transfection instead of a stable producer cell line.

A second rAAV production process features generation and selection of stably transfected HeLa cell clones that contain both the AAV genes Rep/Cap and the GOI. These cell lines then can be infected by wt Ad5 to trigger the packaging of rAAV particles. While this method is scalable, the generation of these clones can be a long and labor intensive process and the removal of wt Ad5 virus from the final product of this process adds multiple steps to the process.

A third rAAV production process relies on recombinant baculovirus for introducing AAV genes (Rep/Cap) and directly performs the necessary helper virus functions for rAAV production in SF9 insect cells. While this method is scalable in suspension culture, it requires generation of plaque purified recombinant baculovirus constructs, and results in a longer time to product development.

A novel, efficient platform for rAAV production, which addresses these deficiencies by providing a rapid process to generate a stable producer cell line for any desired AAV serotype that additionally provides high, scalable production yields without the addition of live helper virus is needed to provide high-quality vectors for use in both preclinical and clinical studies.

The type I interferons (IFN) were the first cytokines discovered and named for their potent ability to "interfere" with viral replication. Many viral products can block the IFN associated signal, such as the influenza NS1 protein and vaccinia virus E3L protein which inhibit protein kinase (PKR), and vaccinia virus-encoded soluble IFN-alpha/beta receptor decoys.

Chinese hamster ovary (CHO) cells (Puck, J. Exp. Med., 108: 259-268 (1958)) are a well characterized cell line often used for the commercial production of recombinant proteins from mammalian cells due to their high productivity, robust nature, safety record and track record in industry (Birch and Racher, Adv. Drug Delivery Rev., 58:671-685 (2006)). However, CHO cells have not been previously used in the production of rAAV.

Various publications are cited herein, the disclosures of which are incorporated by reference herein in their entireties.

BRIEF DESCRIPTION OF THE INVENTION

In some embodiments, the present disclosure provides a mammalian cell comprising (i) at least four distinct recombination target sites (RTS), (ii) an adenovirus (Ad) gene comprising E1A, E1B or a combination thereof, and (iii) a promoter operatively linked to an Ad gene, wherein the RTS, the Ad gene, and the promoter are chromosomally-integrated. In some embodiments, the cell is a mouse cell, a human cell, a Chinese hamster ovary (CHO) cell, a CHO-K1 cell, a CHO-DXB11 cell, a CHO-DG44 cell, a CHOK1SV™ cell (Lonza, Slough, UK) including all variants, a CHOK1SV GS-KO™ (glutamine synthetase knockout) cell (Lonza, Slough, UK) including all variants, a HEK293 cell including adherent and suspension-adapted variants, a HeLa cell, or a HT1080 cell. In some embodiments, the cell comprises four RTSs. In some embodiments, the cell comprises six RTSs. In some embodiments, at least one RTS is selected from the group consisting of SEQ ID NOs.: 1-30. In some embodiments, at least one RTS, the Ad gene, and the promoter are integrated at a single chromosomal locus. In some embodiments, the chromosomal locus is Fer1L4, ROSA26, HGPRT, DHFR, COSMC, LDHa, MGAT1, GRIK1, NL1, NL2, the first intron of MID1 on the X chromosome, or enhanced expression and stability regions (EESYRs, see, e.g., U.S. Pat. No. 7,771,997). In some embodiments, the cell comprises a site-specific recombinase gene. In some embodiments, the site-specific recombinase gene is chromosomally-integrated. In some embodiments, the cell comprises a second Ad gene, wherein the second Ad gene is chromosomally-integrated. In some embodiments, the second Ad gene comprises E1A, E1B, E2A, E4, VA, MIR342, or a combination thereof. In some embodiments, the second Ad gene is from Ad5. In some embodiments, the second Ad gene is located between two of the RTS. In some embodiments, the cell further comprises an adeno-associated virus (AAV) gene, wherein the AAV gene is chromosomally-integrated. In some embodiments, the AAV gene comprises Rep, Cap, or a combination thereof. In some embodiments, the AAV gene is from adeno-associated virus type 2. In some embodiments, the AAV gene is located between two of the RTS. In some embodiments, the cell further comprises an AAV vector cassette, wherein the AAV vector cassette is chromosomally-integrated. In some embodiments, the AAV vector cassette comprises a reporter gene, a selection gene, a gene of therapeutic interest, or a combination thereof. In some embodiments, the AAV vector cassette is located between two of the RTS. In some embodiments, the cell is substantially free of helper virus.

In some embodiments, the present disclosure provides a mammalian cell comprising (i) at least four distinct recombination target sites (RTS), (ii) an Ad gene E2A, E4, VA, MIR342 or a combination thereof, and (iii) a promoter operatively linked to the Ad gene, wherein the RTS, the Ad gene and the promoter are chromosomally-integrated. In some embodiments, the cell is a mouse cell, a human cell, a Chinese hamster ovary (CHO) cell, a CHO-K1 cell, a CHO-DXB11 cell, a CHO-DG44 cell, a CHOK1SV™ cell including all variants, a CHOK1SV GS-KO™ (glutamine synthetase knockout) cell including all variants, a HEK293 cell including adherent and suspension-adapted variants, a HeLa cell, or a HT1080 cell. In some embodiments, the cell comprises four RTSs. In some embodiments, the cell comprises six RTSs. In some embodiments, at least one RTS is selected from the group consisting of SEQ ID Nos.: 1-30. In some embodiments, the RTS, the Ad gene, and the promoter are integrated at a single chromosomal locus. In some embodiments, the chromosomal locus is Fer1L4, ROSA26, HGPRT, DHFR, COSMC, LDHa, MGAT1, GRIK1, NL1, NL2, the first intron of MID1 on the X chromosome, or enhanced expression and stability regions (EESYRs). In some embodiments, the cell comprises a site-specific recombinase gene. In some embodiments, the site-specific recombinase gene is chromosomally-integrated. In some embodiments, the cell further comprises a second Ad gene, wherein the second Ad gene is chromosomally-integrated. In some embodiments, the second Ad gene comprises E1A, E1B, E2A, E4, VA, MIR342, or a combination thereof. In some embodiments, the second Ad gene is from Ad5. In some embodiments, the second Ad gene is located between two of the RTS. In some embodiments, the cell further comprises an adeno-associated virus (AAV) gene, wherein the AAV gene is chromosomally-integrated. In some embodiments, the AAV gene comprises Rep, Cap, or a combination thereof. In some embodiments, the AAV gene is from adeno-associated virus type 2. In some embodiments, the AAV gene is located between two of the RTS. In some embodiments, the cell further comprises an AAV vector cassette, wherein the AAV vector cassette is chromosomally-integrated. In some embodiments, the AAV vector cassette comprises a reporter gene, a selection gene, a gene of therapeutic interest or a combination thereof. In some embodiments, the AAV vector cassette is located between two of the RTS. In some embodiments, the cell is substantially free of helper virus.

In some embodiments, the present disclosure provides a mammalian cell comprising (i) at least four distinct recombination target sites (RTS), (ii) and an adeno-associated virus (AAV) gene comprising Rep, Cap, or a combination thereof, wherein the RTS and the AAV gene are chromosomally-integrated. In some embodiments, the AAV gene is from adeno-associated virus type 2. In some embodiments, the cell is a mouse cell, a human cell, a Chinese hamster ovary (CHO) cell, a CHO-K1 cell, a CHO-DXB11 cell, a CHO-DG44 cell, a CHOK1SV™ cell including all variants, a CHOK1SV GS-KO™ cell including all variants, a HEK293 cell including adherent and suspension-adapted variants, a HeLa cell, or a HT1080 cell. In some embodiments, the cell comprises four RTS. In some embodiments, the cell comprises six RTS. In some embodiments, at least one RTS is selected from the group consisting of SEQ ID NOs.: 1-30. In some embodiments, the RTS and the AAV gene are integrated at a single chromosomal locus. In some embodiments, the chromosomal locus is Fer1L4, ROSA26, HGPRT, DHFR, COSMC, LDHa, MGAT1, GRIK1, NL1, NL2, the first intron of MID1 on the X chromosome, or Enhanced Expression and stability regions (EESYRs). In some embodiments, the cell comprises a site-specific recombinase gene. In some embodiments, the site-specific recombinase gene is chromosomally-integrated. In some embodiments, the cell further comprises an Ad gene and a promoter operatively linked to the Ad gene, whereby the Ad gene and the promoter are chromosomally-integrated. In some embodiments, the Ad gene comprises E1A, E1B, E2A, E4, VA, MIR342 or a combination thereof. In some embodiments, the Ad gene is from Ad5. In some embodiments, the AAV gene is located between two of the RTS. In some embodiments, the cell further comprises an AAV vector cassette, wherein the AAV vector cassette is chromosomally-integrated. In some embodiments, the AAV vector cassette comprises a reporter gene, a selection gene, a gene of therapeutic interest or a combination thereof. In some embodiments, the AAV vector cassette is located between two of the RTS. In some embodiments, the cell is substantially free of helper virus.

In some embodiments, the present disclosure provides a Chinese hamster ovary (CHO) cell comprising: six distinct recombination target site (RTS) wherein at least one RTS is selected from the group consisting of SEQ ID NOs. 1-30, an adenovirus (Ad) gene comprising E1A and E1B, a promoter operatively linked to the Ad gene, wherein the RTS, the Ad gene and the promoter are chromosomally-integrated, a second Ad gene comprising E2A, E4, VA, and M1R342, wherein the second Ad gene is chromosomally-integrated and located between two of the RTS, an adeno-associated virus (AAV) gene comprising Rep and Cap, wherein the AAV gene is chromosomally-integrated and located between two of the RTS, and an AAV vector cassette comprising a reporter gene, a selection gene or a gene of therapeutic interest, wherein the AAV vector cassette is chromosomally-integrated and located between two of the RTS.

In some embodiments, the present disclosure provides a Chinese hamster ovary (CHO) cell comprising an adenovirus (Ad) gene comprising E1A and E1B and a promoter operatively linked to the Ad gene, a second Ad gene comprising E2A, E4, VA, and MIR342, an adeno-associated virus (AAV) gene comprising Rep and Cap, and an AAV vector cassette comprising a reporter gene, a selection gene, a gene of therapeutic interest or a combination thereof.

In some embodiments, the present disclosure provides a method for producing a recombinant adeno-associated virus (rAAV) producer cell comprising: providing a cell that comprises at least four distinct recombination target sites (RTS), an adenovirus (Ad) gene comprising E1A, E1B, or a combination thereof, and a promoter operatively linked to the Ad gene, wherein the RTS, the Ad gene and the promoter are chromosomally-integrated, transfecting the cell provided with a vector comprising an exchangeable cassette encoding an adeno-associated virus (AAV) gene, a second Ad gene, an AAV vector cassette, or a combination thereof, integrating the exchangeable cassette into the chromosome, and selecting rAAV producer cells with the exchangeable cassette integrated into the chromosome. In some embodiments, the transfection is with two vectors, the first vector comprising an exchangeable cassette comprising the second Ad gene and the AAV gene and the second vector comprising an exchangeable cassette comprising the AAV vector cassette. In some embodiments, the transfection is with two vectors, the first vector comprising an exchangeable cassette comprising the second Ad gene and the second vector comprising an exchangeable cassette comprising the AAV gene. In some embodiments, the transfection is with three vectors, the first vector comprising an exchangeable cassette comprising the second Ad gene, the second vector comprising an exchangeable cassette comprising the AAV gene, and the third vector comprising the exchangeable cassette comprising the AAV vector cassette. In some embodiments, each exchangeable cassette further comprises two RTS, matching two of the RTS of the cell. In some embodiments, the second Ad gene comprises E1A, E1B, E2A, E4, VA, MIR342, or a combination thereof. In some embodiments, the AAV gene comprises Rep, Cap, or a combination thereof. In some embodiments, the AAV vector cassette comprises a reporter gene, a selection gene, a gene of therapeutic interest or a combination thereof.

In some embodiments, the present disclosure provides a method for producing recombinant adeno-associated virus (rAAV) comprising of (i) infecting a host cell with rAAV, (ii) producing rAAV packaged with an AAV vector cassette, and (iii) purifying the packaged rAAV, wherein the host cell comprises: at least four distinct recombination target sites (RTS), an adenovirus (Ad) gene comprising E1A, E1B or a combination thereof, a promoter operatively linked to the Ad gene, wherein the RTS, the Ad gene and the promoter are chromosomally-integrated a second Ad gene comprising E1A, E1B, E2A, E4, VA, MIR342, or a combination thereof, an adeno-associated virus (AAV) gene comprising Rep, Cap, or a combination thereof, and the AAV vector cassette comprising a reporter gene, a selection gene, a gene of therapeutic interest or a combination thereof. In some embodiments, no live wild-type helper virus is required for rAAV production and packaging. In some embodiments, expression of E1A is not required for rAAV production. In some embodiments, a minimum of $1.0 \times 10^9$ vg/mL active AAV is obtained after purification.

BRIEF DESCRIPTION OF THE DRAWINGS

FIG. 1A shows a schematic of the experimental design. FIG. 1B shows the detection of green fluorescent protein (GFP) signals in transfected CHOK1SV GS-KO™ cells (left) and HEK293 cells infected with lysate from transfected CHOK1SV GS-KO™ cells (right). FIG. 1C shows the quantification of rAAV titer CHOK1SV GS-KO™ and HEK293 (control) cells by qPCR analysis of viral genomic DNA.

FIG. 5A is a schematic of the experimental design. FIG. 5B shows agarose gel analysis of genomic PCR products for E1A in HEK293F, HEK293L, CHOK1SV GS-KO™ and the CHOK1SV GS-KO™ MOCK and CHOK1SV GS-KO™ (E1A_E1B) pools. FIG. 5C shows agarose gel analysis of genomic PCR products for E1B in HEK293F, HEK293L, CHOK1SV GS-KO™ host and the CHOK1SV GS-KO™ MOCK and CHOK1SV GS-KO™ E1A_E1B pools. FIG. 5D shows agarose gel analysis of RT-PCR products for E1A in HEK293F, HEK293L, CHOK1SV GS-KO™ host and the CHOK1SV GS-KO™ MOCK and CHOK1SV GS-KO™ E1A_E1B pools treated with doxycycline. FIG. 5E shows agarose gel analysis of RT-PCR products for E1B in HEK293F, HEK293L, CHOK1SV GS-KO™ and the CHOK1SV GS-KO™ MOCK and CHOK1SV GS-KO™ E1A_E1B pools treated with doxycycline. Panel F shows western blot analysis of protein lysates for E1A and β-actin in the CHOK1SV GS-KO™ MOCK and CHOK1SV GS-KO™ E1A_E1B pools.

FIG. 7A shows the arrangement of landing pad 1 containing a single or dual function report/marker gene. The reporter gene is under the control of a SV40E promoter and has an SV40 PolyA sequence. Incompatible Frt sites are located between the SV40 promoter and hpt-eGFP gene (Frt-A) and 5' of the SV40 poly A sequence (Frt-B) for recombinase-mediated cassette-exchange (RMCE). FIG. 7B and FIG. 7C show the arrangement of subsequent landing pads contain incompatible Frt sites (C, D, E and F) and a different reporter to allow independent targeting of payload sequences. In this instance Frt sites A-F could be any of those described in Table 2.

FIG. 8A shows the arrangement for a single site CHOK1SV GS-KO™ and HEK293 host. The Ad helper genes are integrated at an SSIS and GOI/Rep/Cap genes are expressed transiently from a plasmid. FIG. 8B shows the arrangement for a double site CHOK1SV GS-KO™ and HEK293 host. The Ad helper and Rep/Cap genes are integrated at two separate SSISs and GOIs are expressed transiently from a plasmid. FIG. 8C shows the arrangement for a triple site CHOK1SV GS-KO™ and HEK293 host. The helper, Rep/Cap and GOI genes are integrated at three separate SSISs. In some instances, the E1A and E1B genes are also integrated in a SSIS to enhance expression.

FIG. 10A shows schematically the architecture of vector pLMC31 (encoding an rAAV vector with an eGFP reporter gene flanked by ITRs at either end of the AAV cassette). The selection marker in this vector is the Neomycin phosphotransferase I gene and Frt sites are arranged for targeting to NL1. FIG. 10B shows schematically the architecture of vector pLMC32 (encoding AAV2 Rep/Cap genes. This vector includes the min p5 promoter (white square) 5' of Rep, containing two enhancer elements to reduce Rep expression and inhibition of rAAV production, and a full p5 promoter (black and white square) 3' of Cap to enhance Cap expression. FIG. 10C shows schematically the architecture of vector pLMC33 (encoding AAV2 Rep/Cap.genes). This vector includes the min p5 promoter (white square) 5' of Rep and a p5$^{mut}$ promoter (black and grey square) with the TATA box mutated to GGGGGGG to reduce promoter activity 3' of Cap. FIG. 10D shows schematically the architecture of vector pLMC34 also encoding AAV2 Rep/Cap genes. The vector includes the wild-type p5 promoter (black and white square) 5' of Rep, and a mutated p5 promoter (black and grey square) 3' of Cap. FIG. 10E shows schematically the architecture of vector of pLMC35 (also encoding AAV2 Rep/Cap genes). This vector includes the mutated p5 promoter (black and grey square) 5' of Rep and 3' of Cap. The selection marker in pLMC32 to pLMC35 is GS cDNA and Frt sites are arranged for targeting to Fer1L4.

FIG. 11. A shows the level of three E1A isoforms: E1A 289R, E1A 243R and E1A 171R (Radko et al. (2015) *PLoS One*. 10:e0140124). E1A protein levels were detected using a mouse anti-E1A antibody diluted 1:1000 (Abcam, ab33183). The molecular weight of E1A, Rep and Cap protein isoforms are shown in brackets. There was no change in E1A protein levels in HEK293 or CHOK1SV GS-KO™ cells transfected with different vectors, but the protein level of each E1A isoform was different between HEK293 and CHOK1SV GS-KO™ cells. FIG. 11. B shows the levels of Rep78 and Rep52 protein. Rep protein levels were detected using a mouse anti Rep antibody diluted 1:1000 (ARP, 03-61069). Shown in brackets is the molecular weight. There was no change in Rep52 protein levels in HEK293 or CHOK1SV GS-KO™ cells transfected with different vectors, but Rep78 protein levels were higher in cells transfected with pLMC34 and pLMC35. FIG. 11. C shows the level of three Cap isoforms: VP1, VP2 and VP3 using a mouse anti Cap antibody diluted 1:1000 (ARP, 03-61058). Shown in brackets is the molecular weight. There was no change in VP3 protein levels in HEK293 cells transfected with different vectors, and VP1 and VP2 were not detectable in HEK293 cells. VP1, VP2 and VP3 were not detectable in CHOK1SV GS-KO™ cells. FIG. 11. D shows the beta-actin loading control using a mouse anti beta-actin antibody diluted 1:1000 (TFS, MA5-1573).

FIG. 15A shows agarose gel analysis of genomic DNA PCR products for specific Rep/Cap integration into a landing pad located in the Fer1L4 gene using primer set P5. The expected product size is 1524 bp. Results show specific Rep/Cap integration into a landing pad located in the Fer1L4 gene in 'A' Pools 4, 5, 6, 7, 9, 11, 17, 18, 19, 21 and all of the analysed 'B' Pools. As expected, specific Rep/Cap integration was not detected in the CHOK1SV GS-KO™ and CHOK1SV GS-KO™ SSI host. FIG. 15B shows agarose gel analysis of genomic DNA PCR products for residual landing pad in the Fer1L4 gene using primer set P6. The expected product size is 487 bp. Results show some residual landing pad, and incomplete Rep/Cap integration into a landing pad located in the Fer1L4 gene in all of 'A' Pools, except 18, and all of 'B' Pools. There was a smaller PCR product in 'A' Pool 19, indicating loss of a part of sequence. As expected, the Fer1L4 landing pad was amplified in CHOK1SV GS-KO™ cells, but not detected in the CHOK1SV GS-KO™ SSI host.

FIG. 16A shows agarose gel analysis of genomic DNA PCR products for specific GOI integration into the NL1 landing pad using primer set P7. The expected product size is 1446 bp. Results show specific GOI integration into a landing pad located in the NL1 locus in all of 'B' Pools but not in 'A' Pools. As expected, specific GOI integration was not detected in the CHOK1SV GS-KO™ and CHOK1SV GS-KO™ SSI host. FIG. 16B shows agarose gel analysis of genomic DNA products for residual NL1 landing pad using primer set P8. The expected product size is 809 bp. Results show some residual landing pad, and incomplete GOI integration into a landing pad located in the NL1 gene in all of 'A' Pools, except 11, and all of 'B' Pools. According to the results, the NL1 landing pad was not intact in 'A' Pool 11, but GOI had not integrated into the landing pad. As expected, the NL1 landing pad was amplified in CHOK1SV GS-KO™ cells, but not detected in the CHOK1SV GS-KO™ SSI host.

FIG. 17. A shows the level of three E1A isoforms: E1A 289R, E1A 243R and E1A 171R. E1A protein levels were detected using a mouse anti-E1A antibody diluted 1:1000 (Abcam, ab33183). The molecular weight of E1A, Rep and Cap protein isoforms are shown in brackets. The levels of all three E1A isoforms were the same in all pools, and slightly higher than in CHOK1SV GS-KO™ cells. FIG. 17. B shows the levels of Rep78 and Rep52 protein. Rep protein levels were detected using a mouse anti Rep antibody diluted 1:1000 (ARP, 03-61069). Shown in brackets is the molecular weight. Rep78 was not detectable. Rep52 was detected in 'A' Pool 13 and 'B' Pools 6, 7, 8 and 10, indicated by *. FIG. 11. C shows the level of three Cap isoforms: VP1, VP2 and VP3 using a mouse anti Cap antibody diluted 1:1000 (ARP, 03-61058). Shown in brackets is the molecular weight. VP1, Vp2 and VP3 were not detected. FIG. 17. D shows the beta-actin loading control using a mouse anti beta-actin antibody diluted 1:1000 (TFS, MA5-1573).

FIG. 19.A shows Rep78 and Rep68 mRNA levels. ~6- and ~5-fold induction was observed in HEK293 and CHOK1SV GS-KO™ cells (respectively) following triple transfection. FIG. 19.B shows Rep78, Rep68, Rep52, and Rep40 mRNA levels. ~11- and ~5-fold induction was observed in HEK293 and CHOK1SV GS-KO™ cells (respectively) following triple transfection. FIG. 19.C shows Rep78 and Rep52 mRNA levels. ~17- and ~4-fold induction was observed in HEK293 and CHOK1SV GS-KO™ cells (respectively) following triple transfection. FIG. 19.D shows total Rep and Cap mRNA levels. ~20- and ~7-fold induction was observed in HEK293 and CHOK1SV GS-KO™ cells (respectively) following triple transfection. FIG. 19.E shows E1A mRNA levels. ~1-fold induction was observed in HEK293 following triple transfection. E1A mRNA was not detected in control CHOK1SV GS-KO™ cells, but was detected following transfection and infection with wt Ad5. FIG. 19. F shows E1B-19K mRNA levels. ~1-fold induction was observed in HEK293 following triple transfection. E1B-19K mRNA was not detected in control CHOK1SV GS-KO™ cells, but was detected following transfection and infection with wt Ad5. FIG. 19.G shows E1B-55K mRNA levels. ~1-fold induction was observed in HEK293 following triple transfection. E1B-55K mRNA was not detected in control CHOK1SV GS-KO™ cells, but was detected following transfection and infection with wt Ad5. FIG. 19.H shows E2A mRNA levels. E2A mRNA was not detectable in control samples, and was present following triple transfection. FIG. 19.I shows E4 mRNA levels. E4 mRNA was not detectable in control samples, and was present following triple transfection. FIG. 19.J shows VAI mRNA levels. VAI mRNA was not detectable in control samples, and was present following triple transfection. FIG. 19.K shows VAII mRNA levels. VAII mRNA was not detectable in control samples, and was present following triple transfection. All of the observed mRNA levels, except E4 were lower in CHOK1SV GS-KO™ in comparison with HEK293 cells (FIG. 19.A-K). These data show that the Rep-Cap mRNA induction and expression were lower in CHOK1SV GS-KO™ cells in comparison with HEK293 cells.

FIG. 20 shows the titers of rAAV from triple transfected HEK293 and CHOK1SV GS-KO™ cells. HEK293 cells were transfected with pHelper (6234, Clontech) and one pLMC32-35 or pRC-mi342 (6234, Clontech) and pLMC31 or pAAV-GFP (AAV-400, Cell Biolabs) vectors. CHOK1SV GS-KO™ cells were infected with wt Ad5 and one pLMC32-35 or pRC-mi342 (6234, Clontech) and pLMC31 or pAAV-GFP (AAV-400, Cell Biolabs) vectors. Three days after transfection, DNA was extracted for TaqMan-qPCR analysis for AAV expression. The AAV titer produced by CHOK1SV GS-KO™ cells was lower than in HEK293 cells, and the titers produced by triple transfected HEK293 cells using pHelper (6234, Clontech), pLMC31 and pLMC32-35 were significantly higher than in HEK293 cells triple transfected using the Clontech vectors (pHelper (6234, Clontech), pRC2-mi342 (6234, Clontech) and pAAV-GFP (AAV-400, Cell Biolabs).

FIG. 21 shows the primer sequences (SEQ ID NOS 43-74, respectively, in order of appearance) used for TaqMan-qPCR and genomic DNA PCR analysis.

DETAILED DESCRIPTION OF THE INVENTION

Figure 1:
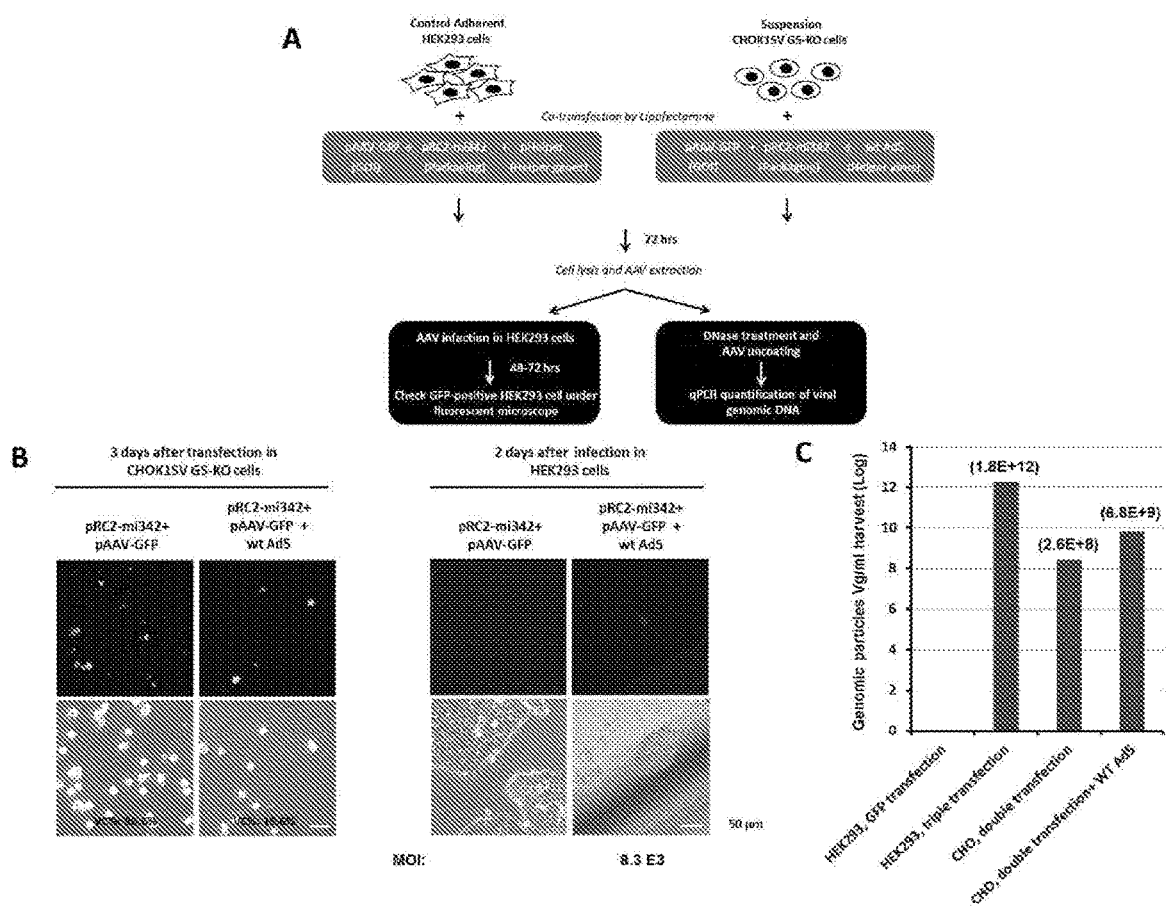
FIG. 1 shows the production of recombinant adeno-associated virus (rAAV) in HEK293 and CHOK1SV GS-KO™ cells. In HEK293 cells plasmid triple transfection was completed (pAAV-GFP (AAV-400, Cell Biolabs), pRC2-mi342 (6234, Clontech) and pHelper (6234, Clontech)). In CHOK1SV GS-KO™ a double transfection was completed (pAAV-GFP (AAV-400, Cell Biolabs) and pRC2-mi342 (6234, Clontech)) with helper virus co-infection (wt Ad5).

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the method/device being employed to determine the value, or the variation that exists among the study subjects. Typically the term is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability depending on the situation.

The use of the term "or" in the claims is used to mean "and/or" unless explicitly indicated to refer only to alternatives or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited, elements or method steps. It is contemplated that any embodiment discussed in this specification can be implemented with respect to any method, system, host cells, expression vectors, and/or composition of the invention. Furthermore, compositions, systems, cells, and/or vectors of the invention can be used to achieve any of the methods as described herein.

The use of the term "for example" and its corresponding abbreviation "e.g." (whether italicized or not) means that the specific terms recited are representative examples and embodiments of the disclosure that are not intended to be limited to the specific examples referenced or cited unless explicitly stated otherwise.

The present disclosure provides a mammalian cell comprising (i) at least four distinct recombination target sites (RTS), (ii) an adenovirus (Ad) gene comprising E1A, E1B or a combination thereof, and (iii) a promoter operatively linked to the Ad gene, wherein the RTS, the Ad gene, and the promoter are chromosomally-integrated.

A "nucleic acid," "nucleic acid molecule," or "oligonucleotide" means a polymeric compound comprising covalently linked nucleotides. The term "nucleic acid" includes polyribonucleic acid (RNA) and polydeoxyribonucleic acid (DNA), both of which may be single- or double-stranded. DNA includes, but is not limited to, complimentary DNA (cDNA), genomic DNA, plasmid or vector DNA, and synthetic DNA. RNA includes, but is not limited to, mRNA, tRNA, rRNA, snRNA, microRNA, miRNA, or MIRNA.

The term "recombinant" when used in reference to a nucleic acid molecule, peptide, polypeptide, or protein means of, or resulting from, a new combination of genetic material that is not known to exist in nature. A recombinant molecule can be produced by any of the well-known techniques available in the field of recombinant technology, including, but not limited to, polymerase chain reaction (PCR), gene cutting (e.g., using restriction endonucleases), and solid state synthesis of nucleic acid molecules, peptides, or proteins. In some embodiments, "recombinant" refers to a viral vector or virus that is not known to exist in nature, e.g. a viral vector or virus that has one or more mutations, nucleic acid insertions, or heterologous genes in the viral vector or virus. In some embodiments, "recombinant" refers to a cell or host cell that is not known to exist in nature, e.g. a cell or host cell that has one or more mutations, nucleic acid insertions, or heterologous genes in the cell or host cell.

An "isolated" polypeptide, protein, peptide, or nucleic acid is a molecule that has been removed from its natural environment. It is also to be understood that "isolated" polypeptides, proteins, peptides, or nucleic acids may be formulated with excipients such as diluents or adjuvants and still be considered isolated.

The terms "sequence identity" or "% identity" in the context of nucleic acid sequences or amino acid sequences refers to the percentage of residues in the compared sequences that are the same when the sequences are aligned over a specified comparison window. A comparison window can be a segment of at least 10 to over 1000 residues in which the sequences can be aligned and compared. Methods of alignment for determination of sequence identity are well-known in the art can be performed using publicly available databases such as BLAST (blast.ncbi.nlm.nih.gov/Blast.cgi.).

In some embodiments, polypeptides or nucleic acid molecules have at least about 70%, at least about 75%, at least about 80%, at least about 85%, at least about 90%, at least about 95%, at least about 97%, at least about 98%, at least about 99% or about 100% sequence identity with a reference polypeptide or nucleic acid molecule, respectively (or a fragment of the reference polypeptide or nucleic acid molecule). In certain embodiments of the disclosure, polypeptides or nucleic acid molecules have at least 70%, at least 75%, at least 80%, at least 85%, at least 90%, at least 95%, at least 97%, at least 98%, or at least 99% or 100% sequence identity with a reference polypeptide or nucleic acid molecule, respectively (or a fragment of the reference polypeptide or nucleic acid molecule). In some embodiments, polypeptides or nucleic acid molecules have about 90%, 91%, 92%, 93%, 94%, 95%, 96%, 97%, 98%, 99%, 99.5% sequence identity with a reference polypeptide or nucleic acid molecule, respectively.

As used herein, "promoter," "promoter sequence," or "promoter region" refers to a DNA regulatory region/sequence capable of binding RNA polymerase and involved in initiating transcription of a downstream coding or noncoding sequence. In some examples of the present disclosure, the promoter sequence includes the transcription initiation site and extends upstream to include the minimum number of bases or elements necessary to initiate transcription at levels detectable above background. In some embodiments, the promoter sequence includes a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the gene expression, e.g., in the host cell or vectors of the present disclosure. In some embodiments, the promoter is not a leaky promoter, i.e., the promoter is not constitutively expressing any one of the gene products as described herein.

As referred to herein, the term "mammalian cell" includes cells from any member of the order Mammalia, such as, for example, human cells, mouse cells, rat cells, monkey cells, hamster cells, and the like. In some embodiments, the cell is a mouse cell, a human cell, a Chinese hamster ovary (CHO) cell, a CHO-K1 cell, a CHO-DXB11 cell, a CHO-DG44 cell, a CHOK1SV™ cell including all variants (e.g. CHOK1SV POTELLIGEN®, Lonza, Slough, UK), a CHOK1SV GS-KO™ (XCEED®, Lonza, Slough, UK) cell including all variants, a HEK293 cell including adherent and suspension-adapted variants, a HeLa cell, or a HT1080 cell.

As referred to herein, the term "chromosomally-integrated" or "chromosomal integration" refers to the stable incorporation of a nucleic acid sequence into the chromosome of a host cell, e.g. a mammalian cell. i.e., a nucleic acid sequence that is chromosomally-integrated into the genomic DNA (gDNA) of a host cell, e.g. a mammalian cell. In some embodiments, a nucleic acid sequence that is chromosomally-integrated is stable. In some embodiments, a nucleic acid sequence that is chromosomally-integrated is not located on a plasmid or a vector. In some embodiments, a nucleic acid sequence that is chromosomally-integrated is not excised. In some embodiments, chromosomal integration is mediated by the clustered regularly interspaced short palindromic repeats (CRISPR) and CRISPR associated protein (Cas) gene editing system (CRISPR/CAS).

The terms "recombination target site-specific integration" or "site-specific integration" as used herein are interchangeable and can be used to introduce one or more genes into a host cell chromosome. See, e.g., Bode et al., *Biol. Chem.* 381:801-813 (2000), Kolb, Cloning and Stem Cells 4:381-392 (2002) and Coates et al., *Trends in Biotech.* 23:407-419 (2005), each of which is incorporated by reference. In some embodiments, "recombination target site-specific integration" or "site-specific integration" refers to integration of a nucleic acid sequence into a chromosome at a specific site. In some embodiments, site-specific integration is through site-specific recombination. In some embodiments, "site-specific recombination" refers to the rearrangement of two DNA partner molecules by specific enzymes performing recombination at their cognate pairs of sequences or target sites. Site-specific recombination and site-specific integration, in contrast to homologous recombination, require very little DNA homology between partner DNA molecules, is RecA-independent, and does not involve DNA replication at any stage. In some embodiments, site specific recombination uses a site-specific recombinase system to achieve site-specific integration of nucleic acids in host cells, e.g. mammalian cells. A recombinase system typically consists of three elements: two specific DNA sequences (recombination target sites) and a specific enzyme (recombinase). The recombinase catalyzes a recombination reaction between the specific recombination target sites.

Other means known to those in the art can be used to insert one or more of the desired nucleic acid sequences (e.g., genes). In some embodiments, one or more nucleic acid sequences (e.g., genes) are inserted into a chromosome using homologous recombination. Homologous recombination refers to refers genetic recombination in which nucleotide sequences are exchanged between two similar or identical molecules of DNA. In some embodiments, the region targeted for deletion/insertion (e.g., a gene) is deleted/inserted by homologous recombination. For example, a DNA construct comprising an incoming sequence having a selective marker flanked on each side by sequences that are homologous to the region targeted for deletion/insertion is used. The DNA construct can align with the homologous sequences of the host chromosome and in a double crossover event the region targeted for (i) deletion is excised out of the host chromosome, or (ii) insertion is added into the chromosome. In some embodiments, homologous recombination is not used to insert a recombination target site, an adenovirus (Ad) gene e.g., E1A, E1B, E2A, E4, VA, MIR342, or combination thereof, and/or a promoter operatively linked to the Ad gene.

A recombinase enzyme, or recombinase, is a specific enzyme that catalyzes recombination in site-specific recombination. In some embodiments of the disclosure, the recombinase used for site-specific recombination is derived from a non-mammalian system. In some embodiments, the recombinase is derived from bacteria, bacteriophage, or yeast.

In some embodiments, a nucleic acid sequence encoding a recombinase is integrated into the host cell, e.g. mammalian cell. In some embodiments, a nucleic acid sequence encoding a recombinase is delivered to the host cell by other methods known to molecular biology. In some embodiments, a recombinase polypeptide sequence can be delivered to the cell directly. In some embodiments, the recombinase is a Cre recombinase, a Dre recombinase, a KD recombinase, a B2B3 recombinase, a Hin recombinase, a Tre recombinase, a λ integrase, a HK022 integrase, a HP1 integrase, a γδ resolvase/invertase, a ParA resolvase/invertase, a Tn3 resolvase/invertase, a Gin resolvase/invertase, a φC31 integrase, a BxB1 integrase, a R4 integrase or another functional recombinase enzyme. See, e.g., Thorpe & Smith, *Proc. Nat'l. Acad. Sci. USA* 95: 5505-5510 (1998); Kuhstoss & Rao, *J. Mol. Biol.* 222: 897-890 (1991); U.S. Pat. No. 5,190,871; Ow & Ausubel, *J. Bacteriol.* 155: 704-713 (1983); Matsuura et al., *J. Bacteriol.* 178: 3374-3376 (1996); Sato et al., *J. Bacteriol.* 172: 1092-1098 (1990); Stragier et al., *Science* 243: 507-512 (1989); Carrasco et al., *Genes Dev.* 8: 74-83 (1994); Bannam et al., *Mol. Microbiol.* 16: 535-551 (1995); Crelin & Rood, *J. Bacteriol.* 179: 5148-5156 (1997).

In some embodiments, a recombinase as described herein is a FLP recombinase. A FLP recombinase is a protein which catalyzes a site-specific recombination reaction that is involved in amplifying the copy number of the 2 µm plasmid of *Saccharomyces cerevisiae* during DNA replication. In some embodiments, the FLP recombinase of the present disclosure is derived from species of the genus *Saccharomyces*. In some embodiments, the FLP recombinase is derived from *Saccharomyces cerevisiae*. In some embodiments, the FLP recombinases is derived from a strain of *Saccharomyces cerevisiae*. In some embodiments, the FLP recombinase is a thermostable, mutant FLP recombinase. In some embodiments, the FLP recombinase is FLP1 or FLPe. In some embodiments, the nucleic acid sequence encoding the FLP recombinase comprises human optimized codons.

In some embodiments, the recombinase is a Cre recombinase. Cre (causes recombination) is a member of the Int family of recombinases (Argos et al. (1986) EMBO J. 5:433) and has been shown to perform efficient recombination of lox sites (locus of X-ing over) not only in bacteria but also in eukaryotic cells (Sauer (1987) Mol. Cell. Biol. 7:2087; Sauer and Henderson (1988) Proc. Natl Acad. Sci. 85:5166). In some embodiments, the Cre recombinase as described and used herein is derived from bacteriophage. In some embodiments, the Cre recombinase is derived from P1 bacteriophage.

As referred to herein, the terms "recombination target site," "RTS" and "site-specific recombinase target site" refer to a short, e.g. less than 60 base pairs, nucleic acid site or sequence which is recognized by a site-specific recombinase and which become the crossover regions during the site-specific recombination event. The acronym "RTS" can refer to a single recombination target site, or plural recombination target sites. In some embodiments, the RTS is less than about 60 base pairs, less than about 55 base pairs, less than about 50 base pairs, less than about 45 base pairs, less than about 40 base pairs, less than about 35 base pairs, or less than about 30 base pairs. In some embodiments, the RTS is about 30 to about 60 base pairs, about 30 to about 55 base pairs, about 32 to about 52 base pairs, about 34 to about 44 base pairs, about 32 base pairs, about 34 base pairs, or about 52 base pairs. Examples of RTS include, but are not limited to, lox sites, rox sites, Frt sites, att sites and dif sites. In some embodiments, RTS are nucleic acids having substantially the same sequence as set forth in any of the sequences in Tables 1, 2, 3 or 4.

In some embodiments, the RTS is a lox site selected from Table 1. As referred to herein, the term "lox site" refers to a nucleotide sequence at which a Cre recombinase can catalyze a site-specific recombination. A variety of non-identical lox sites are known to the art. The sequences of the various lox sites are similar in that they all contain identical 13-base pair inverted repeats flanking an 8-base pair asymmetric core region in which the recombination occurs. It is the asymmetric core region that is responsible for the directionality of the site and for the variation among the different lox sites. Illustrative (non-limiting) examples of these include the naturally occurring loxP (the sequence found in the P1 genome), loxB, loxL and loxR (these are found in the *E. coli* chromosome) as well as several mutant or variant lox sites such as loxP511, loxΔ86, loxΔ117, loxC2, loxP2, loxP3, loxP23, loxC2, loxP2, and loxP3. In some embodiments, the RTS is a lox site selected from loxΔ86, loxΔ117, loxC2, loxP2, loxP3 and loxP23. In some embodiments, a lox RTS is a nucleic acid having at least 90%, 91%, 92%, 93%, 94%, 95%, 96%, 97%, 98%, 99%, or 100% sequence identity to the sequences found in Table 1.

TABLE 1

| Name | Identifier | Sequence |
| --- | --- | --- |
| loxP | SEQ ID NO.: 1 | ATAACTTCGTATAATGT ATGCTATACGAAGTTAT |
| loxP511 | SEQ ID NO.: 2 | ATAACTTCGTATAATGT ATACTATACGAAGTTAT |
| loxP2272 | SEQ ID NO.: 3 | ATAACTTCGTATAAAGT ATCCTATACGAAGTTAT |
| loxP5171 | SEQ ID NO.: 4 | ATAACTTCGTATAATGT GTACTATACGAAGTTAT |
| loxP2272(V) | SEQ ID NO.: 5 | ATAACTTCGTATAGGAT ACTTTATACGAAGTTAT |
| pLox2+ | SEQ ID NO.: 6 | ATAACTTCGTATAATGT ATGCTATACGAAGTTAT |
| loxC2 | SEQ ID NO.: 28 | ACAACTTCGTATAATGT ATGCTATACGAAGTTAT |
| loxP2 | SEQ ID NO.: 29 | TACCGTTCGTATAGTAT AGTATATACGAAGTTAT |
| loxP3 | SEQ ID NO.: 30 | TACCGTTCGTATAGTAT AGTATATACGAACGGTA |

In some embodiments, the RTS is a Frt site selected from Table 2. As referred to herein, the term "Frt site" refers to a nucleotide sequence at which the product of the FLP gene of the yeast 2 µm plasmid, FLP recombinase, can catalyze a site-specific recombination. A variety of non-identical Frt sites are known to the art. The sequences of the various Frt sites are similar in that they all contain identical 13-base pair inverted repeats flanking an 8-base pair asymmetric core region in which the recombination occurs. It is the asymmetric core region that is responsible for the directionality of the site and for the variation among the different Frt sites. Illustrative (non-limiting) examples of these include the naturally occurring Frt, and several mutant or variant Frt sites such as Frt1, Frt2. In some embodiments, the RTS is a Frt site selected from Frt (F), Frt F1 (F1), Frt F2 (F2), Frt F3 (F3), Frt F4 (F4) or Frt F5 (F5). In some embodiments, the RTS is a Frt site selected from Frt F6 (F6), Frt F7 (F7), Frt F14 (F14), Frt F15 (F15) or Ff61. In some embodiments, the RTS is a Frt site selected from F2151, Fw2, F2161 and F2262. In some embodiments, the Frt recombination target site is a nucleic acid having at least 90%, 91%, 92%, 93%, 94%, 95%, 96%, 97%, 98%, 99%, or 100% sequence identity to the sequences found in Table 2.

TABLE 2

| Name | Identifier | Sequence |
| --- | --- | --- |
| F | SEQ ID NO.: 7 | GAAGTTACTATTCCGAAGTTCCTA TTCTCTAGAAAGTATAGGAACTTC |
| F1 | SEQ ID NO.: 8 | GAAGTTACTATTCCGAAGTTCCTA TTCTCTAGATAGTATAGGAACTTC |

TABLE 2-continued

| Name | Identifier | Sequence |
| --- | --- | --- |
| F2 | SEQ ID NO.: 9 | GAAGTTACTATTCCGAAGTTCCTATTCTCTACTTAGTATAGGAACTTC |
| F3 | SEQ ID NO.: 10 | GAAGTTACTATTCCGAAGTTCCTATTCTTCAAATAGTATAGGAACTTC |
| F4 | SEQ ID NO.: 11 | GAAGTTACTATTCCGAAGTTCCTATTCTCTAGAAGGTATAGGAACTTC |
| F5 | SEQ ID NO.: 12 | GAAGTTCCTATTCCGAAGTTCCTATTCTTCAAAAGGTATAGGAACTTC |
| F6 | SEQ ID NO.: 13 | GAAGTTCCTATTCCGAAGTTCCTATTCTTCAAAAAGTATAGGAACTTC |
| F7 | SEQ ID NO.: 14 | GAAGTTCCTATTCCGAAGTTCCTATTCTTCAATAAGTATAGGAACTTC |
| F14 | SEQ ID NO.: 15 | GAAGTTCCTATTCCGAAGTTCCTATTCTATCAGAAGTATAGGAACTTC |
| F15 | SEQ ID NO.: 16 | GAAGTTCCTATTCCGAAGTTCCTATTCTTATAGGAGTATAGGAACTTC |
| Ff61 | SEQ ID NO.: 17 | GAAGTTACTATTCCGAAGTTCCTATACTTTCTGGAGAATAGGAACTTC |
| F2151 | SEQ ID NO.: 18 | GAAGTTACTATTCCGAAGTTCCTATACTCTCCAGAGAATAGGAACTTC |
| Fw2 | SEQ ID NO.: 19 | GAAGTTACTATTCCGAAGTTCCTATACTATCTACAGAATAGGAACTTC |
| F2161 | SEQ ID NO.: 20 | GAAGTTACTATTCCGAAGTTCCTATACTCTCTGGAGAATAGGAACTTC |
| F2262 | SEQ ID NO.: 21 | GAAGTTACTATTCCGAAGTTCCTATACTATCTTGAGAATAGGAACTTC |

In some embodiments, the RTS is a rox site selected from Table 3. As referred to herein, the term "rox site" refers to a nucleotide sequence at which a Dre recombinase can catalyze a site-specific recombination. A variety of non-identical rox sites are known to the art. Illustrative (non-limiting) examples of these include roxR and roxF. In some embodiments, a rox recombination target site is a nucleic acid having at least 90%, 91%, 92%, 93%, 94%, 95%, 96%, 97%, 98%, 99%, or 100% sequence identity to the sequences found in Table 3.

TABLE 3

| Name | Identifier | Sequence |
| --- | --- | --- |
| roxF | SEQ ID NO.: 22 | TAACTTTAAATAATGCCAATTATTTAAAGTTA |
| roxR | SEQ ID NO.: 23 | TAACTTTAAATAATTGGCATTATTTAAAGTTA |

In some embodiments, the RTS is an att site selected from Table 4. As referred to herein, the term "att site" refers to a nucleotide sequence at which a λ integrase or φC31 integrase, can catalyze a site-specific recombination. A variety of non-identical aat sites are known to the art. Illustrative (non-limiting) examples of these include attP, attB, proB, trpC, galT, thrA, and rrnB. In some embodiments, an att recombination target site is a nucleic acid having at least 90%, 91%, 92%, 93%, 94%, 95%, 96%, 97%, 98%, 99%, or 100% sequence identity to the sequences found in Table 4.

TABLE 4

| Name | Identifier | Sequence |
| --- | --- | --- |
| attB | SEQ ID NO.: 24 | CATCAGGGCGGTCAGGCCGTAGATGTGGAAGAACGGCAGCACGGCGAGGACG |
| attP | SEQ ID NO.: 25 | ATGTGGTCCTTTAGATCCACTGACGTGGGTCAGTGTCTCTAAAGGACTCGCG |
| attL | SEQ ID NO.: 26 | CATCAGGGCGGTCAGGCCGTAGATGTGGGTCAGTGTCTCTAAAGGACTCGCG |
| attR | SEQ ID NO.: 27 | ATGTGGTCCTTTAGATCCACTGACGTGGAAGAACGGCAGCACGGCGAGGACG |

As referred to herein, the term "distinct recombination target sites" refers to non-identical or hetero-specific recombination target sites. For example, several variant Frt sites exist, but recombination can usually occur only between two identical Frt sites. In some embodiments, distinct recombination target sites refer to non-identical recombination target sites from the same recombination system (e.g. LoxP and LoxR). In some embodiments, distinct recombination target sites refer to non-identical recombination target sites from different recombination systems (e.g. LoxP and Frt). In some embodiments, distinct recombination target sites refer to a combination of recombination target sites from the same recombination system and recombination target sites from different recombination systems (e.g. LoxP, LoxR, Frt, and Frt1).

Various combinations of RTS can be used. In some embodiments, the cell comprises four RTS. In some embodiments, the cell comprises six RTSs. In some embodiments, at least one RTS is selected from SEQ ID Nos.: 1-30. In some embodiments, at least one RTS is selected from SEQ ID Nos.: 1-6. In some embodiments, at least one RTS is selected from SEQ ID Nos.: 28-30. In some embodiments, at least one RTS is selected from SEQ ID Nos.: 7-21. In some embodiments, at least one RTS is selected from SEQ ID Nos.: 22-23. In some embodiments, at least one RTS is selected from SEQ ID Nos.: 24-27. In some embodiments, at least one RTS is selected from SEQ ID Nos.: 28-30. In some embodiments, the cell comprising at least four distinct RTS includes the following RTS: LoxP_511, Frt_F5, Frt, and LoxP. In some embodiments, the cell comprising at least four distinct RTS includes the following RTS: Frt_F14 and Frt_F15. In some embodiments, the cell comprising at least four distinct RTS includes the following RTS: LoxP_511, Frt_F5, Frt, LoxP, Frt_F14 and Frt_F15. In some embodiments, the cell comprising at least four distinct RTS can include the following RTS: Frt_1, Frt_2, Frt_3, Frt_4. In some embodiments, the cell comprising at least four distinct RTS includes the following RTS: Frt_m5, Frt_wt, Frt_m14, Frt_m15, Frt_m7 and Frt_m6.

As referred to herein, the term "landing pad" refers to a nucleic acid sequence comprising a first recombination target site chromosomally-integrated into a host cell. In some embodiments, a landing site comprises two or more recombination target sites chromosomally-integrated into a host cell. In some embodiments, the cell comprises 1, 2, 3, 4, 5, 6, 7, or 8 landing pads. In some embodiments, landing pads are integrated at up to 1, 2, 3, 4, 5, 6, 7, or 8 distinct chromosomal loci.

As referred to herein, the term "adenovirus" refers to a non-enveloped virus with an icosahedral nucleocapsid containing a double stranded DNA of the family Adenoviridae. Over 50 adenoviral subtypes have been isolated from humans and many additional subtypes have been isolated from other mammals and birds. Birds. See, e.g., Ishibashi et al., "Adenoviruses of animals," In *The Adenoviruses*, Ginsberg, ed., Plenum Press, New York, N.Y., pp. 497-562 (1984); Strauss, "Adenovirus infections in humans," In *The Adenoviruses*, Ginsberg, ed., Plenum Press, New York, N.Y., pp. 451-596 (1984). These subtypes belong to the family Adenoviridae, which is currently divided into two genera, namely Mastadenovirus and Aviadenovirus. All adenoviruses are morphologically and structurally similar. In humans, however, adenoviruses show diverging immunological properties and are, therefore, divided into serotypes. Two human serotypes of adenovirus, namely Ad2 and Ad5, have been studied intensively and have provided the majority of general information about adenoviruses.

A "gene" refers to an assembly of nucleotides that encode a polypeptide, and includes cDNA and genomic DNA nucleic acid molecules. "Gene" also refers to a nucleic acid fragment that can act as a regulatory sequence preceding (5' non-coding sequences) and following (3' non-coding sequences) the coding sequence. In some embodiments, genes are integrated with multiple copies. In some embodiments, genes are integrated at predefined copy numbers.

As referred to herein, the term "adenovirus gene" or "AV gene" refers to a gene that is composed of one or more nucleic acid sequences derived from one or more adenovirus subtypes or serotypes. In some embodiments, the Ad gene is a gene that contributes to Adeno-associated virus replication and packaging. In some embodiments, the Ad gene is E1A, E1B, E2A, E4, VA, MIR342, or a combination thereof or any other Ad gene. In some embodiments, the disclosure provides for a cell in which one or more of Ad genes is chromosomally-integrated into the cell. In some embodiments, the disclosure provides for a cell in which one or more of E1A, E1B, E2A, E4, VA, MIR342 is chromosomally-integrated into the cell. In some embodiments, the Ad gene comprises E1A. In some embodiments, the Ad gene comprises E1A and E1B. In some embodiments, the Ad gene comprises E1A, E1B, and E2A. In some embodiments, the Ad gene comprises E1A, E1B, E2A, and E4. In some embodiments, the Ad gene comprises E1A, E1B, E2A, E4, and VA. In some embodiments, the Ad gene comprises E1A, E1B, E2A, E4, VA, and MIR342. In some embodiments, the Ad gene comprises E1A and E2A. In some embodiments, the Ad gene comprises E1A, E2A, and E4. In some embodiments, the Ad gene comprises E1A, E2A, E4, and VA. In some embodiments, the Ad gene comprises E1A, E2A, E4, VA, and MIR342. In some embodiments, the Ad gene comprises E1A and E4. In some embodiments, the Ad gene comprises E1A, E4, and VA. In some embodiments, the Ad gene comprises E1A, E4, VA, and MIR342. In some embodiments, the Ad gene comprises E1A and VA. In some embodiments, the Ad gene comprises E1A, VA, and MIR342. In some embodiments, the Ad gene comprises E1A and M1R342. In some embodiments, the Ad gene comprises E1B. In some embodiments, the Ad gene comprises E1B and E2A. In some embodiments, the Ad gene comprises E1B, E2A, and E4. In some embodiments, the Ad gene comprises E1B, E2A, E4, and VA. In some embodiments, the Ad gene comprises E1B, E2A, E4, VA and MIR342. In some embodiments, the Ad gene comprises E1B, and E4. In some embodiments, the Ad gene comprises E1B, E4, and VA. In some embodiments, the Ad gene comprises E1B, E4, VA, and MIR342. In some embodiments, the Ad gene comprises E1B and VA. In some embodiments, the Ad gene comprises E1B, VA, and MIR342. In some embodiments, the Ad gene comprises E1B, and MR342. In some embodiments, the Ad gene comprises E2A. In some embodiments, the Ad gene comprises E2A and E4. In some embodiments, the Ad gene comprises E2A, E4, and VA. In some embodiments, the Ad gene comprises E2A, E4, VA, and M1R342. In some embodiments, the Ad gene comprises E2A and VA. In some embodiments, the Ad gene comprises E2A, VA, and MIR342. In some embodiments, the Ad gene comprises E2A and MIR342. In some embodiments, the Ad gene comprises E4. In some embodiments, the Ad gene comprises E4 and VA. In some embodiments, the Ad gene comprises E4, VA, and M1R342. In some embodiments, the Ad gene comprises E4 and M1R342. In some embodiments, the Ad gene comprises VA. In some embodiments, the Ad gene comprises VA and MIR342. In some embodiments, the Ad gene comprises MIR342. In some embodiments, the inventors find that when the Ad gene comprises E1A, E1B, E2A, E4, VA, and MIR342 wherein the Ad gene is chromosomally-integrated, more consistent Ad gene expression is observed. In some embodiments, the Ad gene comprises one or more selected from E1A, E1B, E2A, E4, VA, and MIR342.

As referred to herein, the term "regulatory element" refers to a genetic element which controls some aspect of the expression of nucleic acid sequences. As used herein, a "promoter" is a regulatory element which facilitates the initiation of transcription of an operably linked coding region. In some embodiments, a promoter is an Ad promoter. As used herein, the term "AV promoter" refers to such a regulatory element which is derived from an adenovirus system. In some embodiments, a promoter is an AAV promoter. As used herein, the term "AAV promoter" refers to such a regulatory element which is derived from an adeno-associated virus system. In some embodiments, the disclosure provides for a cell in which one or more AAV promoters are chromosomally-integrated into the cell. As used herein, the term "non-AV promoter" refers to such a regulatory element which is derived from a non-adenovirus system. In some embodiments, the non-AV promoter is derived from a prokaryotic system. In some embodiments, the non-AV promoter is derived from a eukaryotic system. In some embodiments, the disclosure provides for a cell in which one or more promoters are chromosomally-integrated into the cell. In some embodiments, the disclosure provides for a cell in which one or more of non-AV promoters are chromosomally-integrated into the cell. In some embodiments, the disclosure provides for a cell in which one or more of Ad promoters are chromosomally-integrated into the cell. In some embodiments, a promoter is a non-AAV promoter. As used herein, the term "non-AAV promoter" refers to such a regulatory element which is derived from a non adeno-associated virus system. In some embodiments, the non-AAV promoter is derived from a prokaryotic system. In some embodiments, the non-AAV promoter is derived from a eukaryotic system. In some embodiments, the disclosure provides for a cell in which one or more non-AAV promoters are chromosomally-integrated into the cell.

As referred to herein, the terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced. In some embodiments, an Ad gene is operably linked to a promoter, wherein the Ad gene is chromosomally-integrated into the host cell genome. In some embodiments, the Ad gene is operably linked to a non-Ad promoter, where in the Ad gene is chromosomally-integrated into the host cell genome. In some embodiments, the Ad gene is operably linked to an Ad promoter, wherein the Ad gene is chromosomally-integrated into the host cell genome. In some embodiments, an AAV gene is operably linked to a promoter, wherein the AAV gene is chromosomally-integrated into the host cell genome. In some embodiments, the AAV gene is operably linked to a non-AAV promoter, where in the AAV gene is chromosomally-integrated into the host cell genome. In some embodiments, the AAV gene is operably linked to an AAV promoter, where in the AAV gene is chromosomally-integrated into the host cell genome. In some embodiments, a GOI is operably linked to a promoter, wherein the GOI is chromosomally-integrated into the host cell genome. In some embodiments, the GOI gene is operably linked to a non-GOI promoter, wherein the GOI is chromosomally-integrated into the host cell genome. In some embodiments, a recombinase gene is operably linked to a promoter, wherein the recombinase gene is chromosomally-integrated into the host cell genome. In some embodiments, the recombinase gene is operably linked to a promoter, where in the recombinase gene is not integrated into the host cell genome. In some embodiments, a recombinase gene is operably linked to a promoter, wherein the recombinase gene is not chromosomally-integrated into the host cell genome. In some embodiments, the recombinase gene is operably linked to a promoter, where in the recombinase gene is not chromosomally-integrated into the host cell genome.

In some embodiments, regulatory elements operably link gene expression to the presence of an exogenously supplied ligand. In some embodiments, an Ad gene is operably linked to a promoter, wherein the promoter operably links gene expression to the presence of an exogenously supplied ligand and wherein the Ad gene is chromosomally-integrated into the host cell genome. In some embodiments, an AAV gene is operably linked to a promoter, wherein the promoter operably links gene expression to the presence of an exogenously supplied ligand and wherein the AAV gene is chromosomally-integrated into the host cell genome. In some embodiments, a GOI is operably linked to a promoter, wherein the promoter operably links gene expression to the presence of an exogenously supplied ligand and wherein the GOI is chromosomally-integrated into the host cell genome. In some embodiments, a recombinase gene is operably linked to a promoter, wherein the promoter operably links gene expression to the presence of an exogenously supplied ligand and wherein the recombinase gene is chromosomally-integrated into the host cell genome. In some embodiments, a recombinase gene is operably linked to a promoter, wherein the promoter operably links gene expression to the presence of an exogenously supplied ligand and wherein the recombinase gene is not chromosomally-integrated into the host cell genome. In some embodiments, E1A expression is operably linked to a promoter, wherein the promoter operably links gene expression to the production of rAAV. In some embodiments, E1A expression is operably linked to a promoter, wherein the promoter operably links gene expression to the presence of an exogenously supplied ligand and wherein gene expression operably links the present of the exogenously supplied ligand to the production of rAAV.

In some embodiments, at least one RTS, the Ad gene, and the promoter are integrated at a single chromosomal locus. In some embodiments, a first Ad gene E1A and E1B, and a second Ad gene comprising E2A, E4, VA and MIR342 are on two different loci. In some embodiments, a first Ad gene E1A and E1B, and a second Ad gene comprising E2A, E4, VA and MIR342 are on the same locus. In some embodiments, a first Ad gene E1A and E1B, and a second Ad gene comprising E2A, E4, VA and MIR342 are the same locus, and an adeno-associated virus (AAV) gene is on a different locus. In some embodiments, a first Ad gene E1A and E1B, and a second Ad gene comprising E2A, E4, VA and MIR342 are the same locus, and an adeno-associated virus (AAV) gene and an AAV vector cassette is on a different locus.

As referred to herein, the term "chromosomal locus" refers to a defined location of nucleic acids on the chromosome of the cell that may comprise at least one gene. In some embodiments, the chromosomal locus is about 500 base pairs to about 100,000 base pairs, about 5,000 base pairs to about 75,000 base pairs, about 5,000 base pairs to about 60,000 base pairs, about 20,000 base pairs to about 50,000 base pairs, about 30,000 base pairs to about 50,000 base pairs, or about 45,000 base pairs to about 49,000 base pairs. In some embodiments, the chromosomal locus extends up to about 100 base pairs, about 250 base pairs, about 500 base pairs, about 750 base pairs, or about 1000 base pairs to the 5' or the 3' end of the defined nucleic acid sequence. In some embodiments, the chromosomal locus comprises an endogenous nucleic acid sequence. In some embodiments, the chromosomal locus comprises an exogenous nucleotide sequence having been integrated into the chromosome using methods known to one of the art of molecular biology. In some embodiments, the chromosomal locus comprises a nucleotide sequence, in the genome of a host cell which provides for a strong and stable production of a protein encoded by a gene integrated within the chromosomal locus. In some embodiments, the chromosomal locus comprises a nucleotide sequence in the genome of a host cell which provides for a strong and stable viral gene expression. In some embodiments, the chromosomal locus comprises a nucleotide sequence in the genome of a host cell which provides efficient site specific recombination. In some embodiments, the chromosomal locus comprises Fer1L4 (see e.g. U.S. patent application Ser. No. 14/409,283), ROSA26, HGPRT, DHFR, COSMC, LDHA, or MGAT1. In some embodiments, the chromosomal locus comprises NL or NL2. In some embodiments, the chromosomal locus the first intron of MID1 on the X chromosome. In some embodiments, the chromosomal locus is an Enhanced Expression and Stability Region (Regeneron, Tarrytown, NY EESYRs, see, e.g., U.S. Pat. No. 7,771,997). In some embodiments, at least a portion of the nucleic acids in the chromosomal locus is deleted.

In some embodiments, the chromosomal locus comprises the NL1 locus, the NL2 locus, the NL3 locus, the NL4 locus, the NL5 locus, or the NL6 locus as described in Table A. In some embodiments, the disclosure is directed to a mammalian cell comprising at least two distinct recombination target sites (RTS) wherein at least one RTS, the Ad gene, and the promoter are integrated within the NL1 locus, the NL2 locus, the NL3 locus, the NL4 locus, the NL5 locus, or the NL6 locus. In some embodiments, a first Ad gene E1A and E1B, and a second Ad gene comprising E2A, E4, VA and MIR342 are on two different loci, one of which is within the NL1 locus, the NL2 locus, the NL3 locus, the NL4 locus, the NL5 locus, or the NL6 locus. In some embodiments, a first Ad gene E1A and E1B, and a second Ad gene comprising E2A, E4, VA and MIR342 are within the NL1 locus, the NL2 locus, the NL3 locus, the NL4 locus, the NL5 locus, or the NL6 locus. In some embodiments, a first Ad gene E1A and E1B, and a second Ad gene comprising E2A, E4, VA and M1R342 are within the NL1 locus, the NL2 locus, the NL3 locus, the NL4 locus, the NL5 locus, or the NL6 locus. In some embodiments, a first Ad gene E1A and E1B, and a second Ad gene comprising E2A, E4, VA and MIR342 are within the NL1 locus, the NL2 locus, the NL3 locus, the NL4 locus, the NL5 locus, or the NL6 locus. In some embodiments, the disclosure is directed to a mammalian cell comprising at least three distinct recombination target sites (RTS) wherein at least one RTS, the Ad gene, and the promoter are integrated within the NL1 locus, the NL2 locus, the NL3 locus, the NL4 locus, the NL5 locus, or the NL6 locus. In some embodiments, the disclosure is directed to a mammalian cell comprising at least four distinct recombination target sites (RTS) wherein at least one RTS, the Ad gene, and the promoter are integrated within the NL1 locus, the NL2 locus, the NL3 locus, the NL4 locus, the NL5 locus, or the NL6 locus. In some embodiments, the disclosure is directed to a mammalian cell comprising at least five distinct recombination target sites (RTS) wherein at least one RTS, the Ad gene, and the promoter are integrated within the NL1 locus, the NL2 locus, the NL3 locus, the NL4 locus, the NL5 locus, or the NL6 locus. In some embodiments, the disclosure is directed to a mammalian cell comprising at least six distinct recombination target sites (RTS) wherein at least one RTS, the Ad gene, and the promoter are integrated within the NL1 locus, the NL2 locus, the NL3 locus, the NL4 locus, the NL5 locus, or the NL6 locus.

50,000 bp, within about 40,000 bp, within about 30,000 bp, within 20,000 bp or within 10,000 bp of the indicated genomic coordinates.

In some embodiments, the cell comprises a site-specific recombinase gene. In some embodiments, the site-specific recombinase gene is chromosomally-integrated.

As referred to herein, the term "located between two of the RTS" refers to a gene located between two of the RTS, i.e., with one of the RTS located 5' of the gene and a different RTS located 3' of the gene. In some embodiments, the RTS are located directly adjacent to the gene located between them. In some embodiments, the RTS are located at a defined distance from the gene located between them. In some embodiments, the RTS are directional sequences. In some embodiments, the RTS 5' and 3' of the gene located between them are directly oriented (i.e. they are oriented in the same direction). In some embodiments, the RTS 5' and 3' of the gene located between them are inversely oriented (i.e. they are oriented in opposite directions).

In some embodiments, the cell further comprises an adeno-associated virus (AAV) gene, wherein the AAV gene is chromosomally-integrated. An AAV gene comprises any gene from any AAV serotype. In some embodiments, the AAV gene is Rep, Rep78, Rep68, Rep52, Rep40, Cap, VP1,

TABLE A

| New Loci | Loci Gene Annotation | | | Loci Location in *Cricetulus griseus* | | | Loci Location in *Homosapien* | | |
|---|---|---|---|---|---|---|---|---|---|
| | 5' gene | Within gene | 3' gene | NCBI Reference Sequence (*Cricetulus griseus*) | Vector Location | Landing Pad Location | Chromosome | Vector Location | Landing Pad Location |
| Fer1 | Ergic3 | Fer1L4 | Spag4 | gi\|351517716\|ref\|NW_003613833\|Scaffold 1492 SEQ ID NO: 31 | N/A | 24894-26755 | Chr 20 | 33613757-33614117 | 33630003-33629572 |
| NL1 | Col5a2 (pseudo) | No annotated gene | Col5a2 | gi\|351515650\|ref\|NW_003615899.1\|Scaffold 2552 SEQ ID NO: 32 | 143287 | 133598 | Chr 2 | 189725696-189726735 | 189725180-189727852 |
| NL2 | LOC103162114 | Naa15 (Intron between Exon 5 & 6) | Rab33b | gi\|351517715\|ref\|NW_003613834.1\|Scaffold2422 SEQ ID NO: 33 | 1303708 to 1308873 | 1313999 | Chr 4 | 140474660-140474867 | 140483934-140483457 |
| NL3 | CJO004127.1 | No annotated gene | Mthfd2 | gi\|351516540\|ref\|NW_003615009.1\|Scaffold3922 SEQ ID NO: 34 | 279558 | N/A | Chr 2 | 74277198-74297932 | N/A |
| NL4 | MORF4L1 | No annotated gene | No annotated gene | gi\|351516248\|ref\|NW_003615301.1\|Scaffold502 SEQ ID NO: 35 | 173850 | N/A | Chr 15 | 76952458 | N/A |
| NL5 | ZNHIT1 | No annotated gene | Tatc1 | gi\|351517397\|ref\|NW_003614152.1\|Scaffold3667 SEQ ID NO: 36 | 779010 | N/A | Chr 7 | 100648176-100653983 | N/A |
| NL6 | Arhgef28 | Utp15 | Ankra | gi\|351516957\|ref\|NW_003614592.1\|Scaffold7019 SEQ ID NO: 37 | 225021 | N/A | Chr 5 | 73084488-73084783 | N/A |

One of skill in the art will recognize that the term "integrated within the NL1 locus" or "integrated within the NL2 locus" will include integration into any part of the locus, and it not limited to just the indicated genomic coordinates. One of skill in the art will recognize that the term "integrated within the NL1 locus" or "integrated within the NL2 locus" would also include corresponding loci in corresponding organisms. Thus, in some embodiments, the term "integrated within the NL1 locus" or "integrated within the NL2 locus" will include an integration within about VP2, VP3, or a combination thereof. In some embodiments, the AAV gene is from adeno-associated virus type 2. In some embodiments, the AAV gene is from the adeno-associated virus Anc80. In some embodiments, the AAV gene comprises the ANC80 Rep and Cap genes. In some embodiments, the AAV gene is located between two of the RTS.

As referred to herein, the term "adeno-associated virus (AAV)" refers to a small sized, replicative-defective nonenveloped virus containing a single stranded DNA of the family Parvoviridae and the genus Dependoparvovirus.

Over 10 adeno-associated virus serotypes have been identified so far, with serotype AAV2 being the best characterized. Other (non-limiting) examples of AAV serotypes are ANC80, AAV1, AAV3, AAV4, AAV5, AAV6, AAV7, AAV8, AAV9, AAV10, and AAV11. In addition to these serotypes, AAV pseudotypes have been developed. An AAV pseudotype contains the capsid of a first serotype and the genome of a second serotype (e.g. the pseudotype AAV2/5 would correspond to an AAV with the genome of serotype AAV2 and the capsid of AAV5).

As used herein, the term "recombinant AAV" or "rAAV" is defined as an infectious, replication-defective virus composed of an AAV protein shell encapsidating (i.e., surrounding with a protein coat) a heterologous gene, which in turn is flanked 5' and 3' by AAV ITRs.

As used herein, the term replication competent adenovirus (RCA) refers to undesired contaminants of active adenovirus particles sometimes produced during rAAV production generated by homologous recombination between a recombinant adenovirus vector and the adenovirus genes present in the producer cell genome.

As referred to herein, the term "adeno-associated virus gene" refers to a gene that is composed of one or more nucleic acid sequences derived from one or more adeno-associated virus serotypes. In some embodiments, the AAV gene comprises a gene that contributes to AAV replication and packaging.

As referred to herein, the term "Rep" gene is meant the art-recognized region of the AAV genome which encodes the replication proteins of the virus which are collectively required for replicating the viral genome, or functional homologues thereof such as the human herpesvirus 6 (HHV-6) rep gene which is also known to mediate AAV-2 DNA replication. Thus, the rep coding region includes at least the genes encoding for AAV Rep78 and Rep68 (the "long forms of Rep"), and Rep52 and Rep40 (the "short forms of Rep"), or functional homologues thereof. For a further description of the AAV rep coding region. The rep coding region, as used herein, can be derived from any viral serotype, such as the AAV serotypes described above. The region need not include all wild-type genes but may be altered, (e.g., by insertion, deletion or substitution of nucleotides), so long as the rep genes present provide for sufficient integration functions when expressed in a suitable target cell. See, e.g. Muzyczka, N., *Current Topics in Microbiol. and Immunol.* 158:97-129 (1992); and Kotin, R. M., *Human Gene Therapy* 5:793-801 (1994).

As referred to herein, the term "Cap" gene refers to the art-recognized region of the AAV genome which encodes the capsid proteins of the virus. Illustrative (non-limiting) examples of these capsid proteins are the AAV capsid proteins VP1, VP2, and VP3. Cap genes used in this disclosure can come from any AAV serotype or a combination of AAV serotypes.

In some embodiments, the cell comprises a second Ad gene, wherein the second Ad gene is chromosomally-integrated. In some embodiments, the second Ad gene is E1A, E1B, E2A, E4, VA, MIR342, or a combination thereof. In some embodiments, the second Ad gene is from Ad5. In some embodiments, the second Ad gene is located between two of the RTS.

In some embodiments, the cell further comprises an AAV vector cassette, wherein the AAV vector cassette is chromosomally-integrated. In some embodiments, the AAV vector cassette is located between two of the RTS.

A "vector" or "expression vector" is a replicon, such as a plasmid, phage, virus, or cosmid, to which another DNA segment may be attached to bring about the replication and/or expression of the attached DNA segment in a cell. "Vector" includes episomal (e.g., plasmids) and non episomal vectors. In some embodiments of the present disclosure the vector is an episomal vector, which is removed/lost from a population of cells after a number of cellular generations, e.g., by asymmetric partitioning. The term "vector" includes both viral and non-viral means for introducing a nucleic acid molecule into a cell in vitro, in vivo, or ex vivo. The term vector may include synthetic vectors. Vectors may be introduced into the desired host cells by well-known methods, including, but not limited to, transfection, transduction, cell fusion, and lipofection. Vectors can comprise various regulatory elements including promoters.

"Transfection" as used herein means the introduction of an exogenous nucleic acid molecule, including a vector, into a cell. A "transfected" cell comprises an exogenous nucleic acid molecule inside the cell and a "transformed" cell is one in which the exogenous nucleic acid molecule within the cell induces a phenotypic change in the cell. The transfected nucleic acid molecule can be integrated into the host cell's genomic DNA and/or can be maintained by the cell, temporarily or for a prolonged period of time, extra-chromosomally. Host cells or organisms that express exogenous nucleic acid molecules or fragments are referred to as "recombinant," "transformed," or "transgenic" organisms. A number of transfection techniques are generally known in the art. See, e.g., Graham et al., *Virology*, 52:456 (1973); Sambrook et al., Molecular Cloning, a laboratory manual, Cold Spring Harbor Laboratories, New York (1989); Davis et al., Basic Methods in Molecular Biology, Elsevier (1986); and Chu et al., *Gene* 13:197 (1981). Such techniques can be used to introduce one or more exogenous DNA moieties, such as an AAV vector cassette, AAV helper constructs, and other nucleic acid molecules, into suitable host cells.

As used herein, the term "exchangeable cassette" or "cassette" is a type of mobile genetic element that contains a gene and a recombination site. In some embodiments, the exchangeable cassette comprises at least two RTS. In some embodiments, the exchangeable cassette comprises a reporter gene or a selection gene. In some embodiments, a cassette is exchanged through recombinase-mediated cassette-exchange (RMCE).

As referred to herein, the term "AAV vector cassette" refers to a cassette derived from an adeno-associated virus serotype vector. An AAV vector cassette can have one or more of the AAV wild-type genes deleted in whole or in part, e.g. the Rep and/or Cap genes, but retain functional flanking inverted terminal repeat (ITR) sequences.

As referred to herein, the term "functional flanking inverted terminal repeat" or "functional flaking ITR" sequences refer to the 145 base pair ITRs, the first 125 base pairs of which are capable of forming Y or T shaped duplex structures that are positioned at the 5' and 3' end of a gene of interest (GOI) in an AAV vector cassette. ITR sequences represent the minimal sequence required for replication, rescue, packaging and integration of the AAV genome.

As referred to herein, the terms "ancillary gene," "helper gene" and "ancillary helper gene" are used interchangeable to refer to a first gene that aids in the replication or packaging of rAAV. In some embodiments, the helper gene comprises a viral gene. In some embodiments, the helper gene comprises an Ad gene. In some embodiments, the helper gene comprises an AAV gene. In some embodiments, the helper gene comprises the AAV gene rep, cap or a combination thereof. In some embodiments, the helper gene comprises a prokaryotic gene. In some embodiments, the helper gene comprises a eukaryotic gene. In some embodiments, the helper gene comprises a gene encoding an RNA. In some embodiments, the helper gene comprises an interferon (IFN) antagonist. In some embodiments, the helper gene encodes a protein that is a Protein Kinase R (PKR) inhibitor. In some embodiments, the helper gene comprises a gene encoding the influenza NS1 protein. In some embodiments, the helper gene comprises a gene encoding the Vaccinia virus E3L protein, see e.g. de Vries et al, *Gene Ther.* 15:545-52, (2008). In some embodiments, the helper gene encodes a virus-encoded soluble IFN-alpha/beta receptor decoys which counteract the IFN response in infected cells. In some embodiments, the helper gene encodes NS1, E3L, or similar proteins. In some embodiments, the helper gene encodes NS1, E3L or proteins with homologous sequences or motifs.

As referred to herein, the term "gene of interest" or "GOI" is used to describe a heterologous gene. As referred to herein, the term "heterologous gene" or "HG" as it relates to nucleic acid sequences such as a coding sequence or a control sequence, denotes a nucleic acid sequence, e.g. a gene, that is not normally joined together, and/or are not normally associated with a particular cell. In some embodiments, a heterologous gene is a construct where the coding sequence itself is not found in nature (e.g., synthetic sequences having codons different from the native gene). Allelic variation or naturally occurring mutational events do not give rise to heterologous DNA, as used herein.

In some embodiments, the gene of interest comprises a reporter gene, a selection gene, a gene of therapeutic interest, or a combination thereof.

As referred to here, a "reporter gene" is a gene whose expression confers a phenotype upon a cell that can be easily identified and measured. In some embodiments, the reporter gene comprises a fluorescent protein gene. In some embodiments, the reporter gene comprises a selection gene.

As referred to herein, the term "selection gene" refers to the use of a gene which encodes an enzymatic activity that confers the ability to grow in medium lacking what would otherwise be an essential nutrient; in addition, a selection gene may confer resistance to an antibiotic or drug upon the cell in which the selection gene is expressed. A selection gene may be used to confer a particular phenotype upon a host cell. When a host cell must express a selection gene to grow in selective medium, the gene is said to be a positive selection gene. A selection gene can also be used to select against host cells containing a particular gene; a selection gene used in this manner is referred to as a negative selection gene.

As referred to herein, the term "gene of therapeutic interest" refers to any functionally relevant nucleotide sequence. Thus, the gene of therapeutic interest of the present disclosure can comprise any desired gene that encodes a protein that is defective or missing from a target cell genome or that encodes a non-native protein having a desired biological or therapeutic effect (e.g., an antiviral function), or the sequence can correspond to a molecule having an antisense or ribozyme function. Representative (non-limiting) examples of suitable genes of therapeutic interest include those used for the treatment of inflammatory diseases, autoimmune, chronic and infectious diseases, including such disorders as AIDS, cancer, neurological diseases, cardiovascular disease, hypercholestemia; various blood disorders including various anemias, thalassemias and hemophilia; genetic defects such as cystic fibrosis, Gaucher's Disease, adenosine deaminase (ADA) deficiency, emphysema, etc. Several antisense oligonucleotides (e.g., short oligonucleotides complementary to sequences around the translational initiation site (AUG codon) of an mRNA) that are useful in antisense therapy for cancer and for viral diseases have been described in the art and are also examples of suitable genes of therapeutic interest.

In some embodiments, the cell is substantially free of helper virus. As referred to herein, a 'helper virus' is any non-AAV virus that is added to enable the replication and packaging of adeno-associated virus. Representative (non-limiting) examples of helper viruses are adenovirus and herpes virus. In some embodiments, the term substantially free of helper virus refers to a cell that has fewer than 100, fewer than 10, or fewer than 1 helper virus per cell. In some embodiments, the term substantially free of helper virus refers to a cell in which no helper viruses are present or to a population of cells in which no helper viruses are present using detection methods known to those skilled in the art. In some embodiments, no wild-type helper virus is in the cell. In some embodiments, the term wild-type virus refers to any complete-non-AAV virus that can replicate in the cell independently of any other virus.

In some embodiments, the present disclosure provides a mammalian cell comprising (i) at least four distinct recombination target sites (RTS), (ii) an adenovirus (Ad) gene E2A, E4, VA, M1R342 or a combination thereof; and (iii) a promoter operatively linked to the Ad gene, wherein the RTS, the Ad gene and the promoter are chromosomally-integrated. In some embodiments, the cell is a mouse cell, a human cell, a CHO cell, a CHO-K1 cell, a CHO-DXB11 cell, a CHO-DG44 cell, a CHOK1SV™ cell including all variants (e.g. CHOK1SV™ POTELLIGENT®), a CHOK1SV GS-KO™ cell including all variants (e.g. XCEED™), a HEK293 cell including adherent and suspension-adapted variants, a HeLa cell, or a HT1080 cell.

In some embodiments, the cell comprises four RTSs. In some embodiments, the cell comprises six RTSs. In some embodiments, at least one RTS is selected from SEQ ID NOs.: 1-30. In some embodiments, the RTS, the Ad gene, and the promoter are integrated at a single chromosomal locus. In some embodiments, the chromosomal locus is Fer1L4, ROSA26, HGPRT, DHFR, COSMC, LDHa, MGAT1, GRIK1, NL1, NL2, NL3, NL4, NL5, NL6, the first intron of MID1 on the X chromosome, or Enhanced Expression and stability regions (EESYRs). In some embodiments, the cell comprises a site-specific recombinase gene. In some embodiments, the site-specific recombinase gene is chromosomally-integrated. In some embodiments, the cell further comprises a second Ad gene, wherein the second Ad gene is chromosomally-integrated. In some embodiments, the second Ad gene comprises E1A, E1B, E2A, E4, VA, MIR342, or a combination thereof. In some embodiments, the second Ad gene is from Ad5. In some embodiments, the second Ad gene is located between two of the RTS. In some embodiments, the cell further comprises an adeno-associated virus (AAV) gene, wherein the AAV gene is chromosomally-integrated. In some embodiments, the AAV gene comprises Rep, Cap, or a combination thereof. In some embodiments, the AAV gene is from adeno-associated virus type 2. In some embodiments, the AAV gene is located between two of the RTS. In some embodiments, the cell further comprises an AAV vector cassette, wherein the AAV vector cassette is chromosomally-integrated. In some embodiments, the AAV vector cassette is a reporter gene, a selection gene, a gene of therapeutic interest or a combination thereof. In some embodiments, the AAV vector cassette is located between two of the RTS. In some embodiments, the cell is substantially free of helper virus.

In some embodiments, the present disclosure provides a mammalian cell comprising (i) at least four distinct recombination target sites (RTS); and (ii) and an adeno-associated virus (AAV) gene comprising Rep, Cap, or a combination thereof, wherein the RTS and the AAV gene are chromosomally-integrated. In some embodiments, the cell is a mouse cell, a human cell, a CHO cell, a CHO-K1 cell, a CHO-DXB11 cell, a CHO-DG44 cell, a CHOK1SV™ cell including all variants (e.g. CHOK1SV POTELLIGENT®), a CHOK1SV GS-KO™ cell including all variants, a HEK293 cell including adherent and suspension-adapted variants, a HeLa cell, or a HT1080 cell. In some embodiments, the cell comprises four RTS. In some embodiments, the cell comprises six RTS. In some embodiments, at least one RTS is selected from SEQ ID Nos.: 1-30. In some embodiments, the RTS and the AAV gene are integrated at a single chromosomal locus. In some embodiments, the chromosomal locus is Fer1L4, ROSA26, HGPRT, DHFR, COSMC, LDHa, MGAT1, GRIK1, NL1, NL2, the first intron of MID1 on the X chromosome, or Enhanced Expression and stability regions (EESYRs). In some embodiments, the cell comprises a site-specific recombinase gene. In some embodiments, the site-specific recombinase gene is chromosomally-integrated. In some embodiments, the cell further comprises an Ad gene and a promoter operatively linked to the Ad gene, whereby the Ad gene and the promoter are chromosomally-integrated. In some embodiments, the Ad gene comprises E1A, E1B, E2A, E4, VA, MIR342 or a combination thereof. In some embodiments, the Ad gene is from Ad5. In some embodiments, the AAV gene is located between two of the RTS. In some embodiments, the cell further comprises an AAV vector cassette. In some embodiments, the AAV vector cassette comprises a reporter gene, a selection gene, a gene of therapeutic interest or a combination thereof. In some embodiments, the gene of interest is located between two of the RTS. In some embodiments, the cell is substantially free of helper virus. In some embodiments, the cell is completely free of helper virus.

In some embodiments, the present disclosure provides a Chinese hamster ovary (CHO) cell comprising: six distinct recombination target sites (RTS) wherein at least one RTS is selected from SEQ ID NOs.:1-30; an adenovirus (Ad) gene comprising E1A and E1B; a promoter operatively linked to the Ad gene, wherein the RTS, the Ad gene and the promoter are chromosomally-integrated; a second Ad gene comprising E2A, E4, VA, and MIR342, wherein the second Ad gene is located between two of the RTS; an adeno-associated virus (AAV) gene comprising Rep and Cap, wherein the AAV gene is located between two RTS; and an AAV vector cassette comprising a reporter gene, a selection gene or a gene of therapeutic interest, wherein the AAV vector cassette is located between two RTS.

In some embodiments, the present disclosure provides a Chinese hamster ovary (CHO) cell comprising an adenovirus (Ad) gene comprising E1A and E1B and a promoter operatively linked to the Ad gene, a second Ad gene comprising E2A, E4, VA, and M1R342, an adeno-associated virus (AAV) gene comprising Rep and Cap, and an AAV vector cassette comprising a reporter gene, a selection gene, a gene of therapeutic interest or a combination thereof.

In some embodiments, the present disclosure provides a method for producing a recombinant adeno-associated virus (rAAV) producer cell comprising: providing a cell that comprises at least four distinct recombination target sites (RTS), an adenovirus (Ad) gene comprising E1A, E1B, or a combination thereof, and a promoter operatively linked to the Ad gene, wherein the RTS, the Ad gene and the promoter are chromosomally-integrated, transfection of the cell provided with a vector comprising an exchangeable cassette encoding an adeno-associated virus (AAV) gene, a second Ad gene, an AAV vector cassette, or a combination thereof, integrating the exchangeable cassette into the chromosome, and selecting rAAV producer cells with the exchangeable cassette integrated into the chromosome. In some embodiments, the transfection is with two vectors, the first vector comprising an exchangeable cassette comprising the second Ad gene and the AAV gene and the second vector comprising an exchangeable cassette comprising the AAV vector cassette. In some embodiments, the transfection is with two vectors, the first vector comprising an exchangeable cassette comprising the second Ad gene and the second vector comprising an exchangeable cassette comprising the AAV gene. In some embodiments, the transfection is with three vectors, the first vector comprising an exchangeable cassette comprising the second Ad gene, the second vector comprising an exchangeable cassette comprising the AAV gene, and the third vector comprising the exchangeable cassette comprising the AAV vector cassette. In some embodiments, each exchangeable cassette further comprises two RTS, matching two of the RTS of the cell. In some embodiments, the inventors find that the use of SSI eliminates the need to clone cells from those transfected, as the cells are homogenous in their genetic composition.

The term "matching" in reference to two RTS sequences refers to two sequences that have the ability to be bound by a recombinase and to affect a site-specific recombination between the two sequences. In some embodiments, an RTS of an exchangeable cassette matching an RTS of the cell refers to the RTS of the cassette having a sequence substantially identical to the RTS of the cell. In some embodiments, the exchangeable cassette contains a sequence substantially identical to one or two of the RTS chromosomally-integrated in the cell.

In some embodiments, the term integrating refers to the integration, e.g. insertion, of the exchangeable cassette into the chromosome. In some embodiments, integration is mediated by a site-specific recombinase.

In some embodiments, the term "selecting" refers to identifying cells containing a chromosomally-integrated marker. In some embodiments, selection is through the detection of the presence of a marker using methods known to those skilled in the art. In some embodiments, selection is through the detection of the absence of a marker using methods known to those skilled in the art.

In some embodiments, the second Ad gene comprises E1A, E1B, E2A, E4, VA, MIR342, or a combination thereof. In some embodiments, the AAV gene is Rep, Cap, or a combination thereof. In some embodiments, the AAV vector cassette comprises a reporter gene, a selection gene, a gene of therapeutic interest or a combination thereof.

In some embodiments, the present disclosure provides a method for producing recombinant adeno-associated virus (rAAV) comprising of (i) infecting a host cell with AAV, (ii) producing rAAV packaged with an AAV vector cassette, and (iii) purifying the packaged rAAV, wherein the host cell comprises: at least four distinct recombination target sites (RTS), an adenovirus (Ad) gene comprising E1A, E1B or a combination thereof, a promoter operatively linked to the Ad gene, wherein the RTS, the Ad gene and the promoter are chromosomally-integrated, a second Ad gene comprising E1A, E1B, E2A, E4, VA, MIR342, or a combination thereof, an adeno-associated virus (AAV) gene comprising Rep, Cap, or a combination thereof, and the AAV vector cassette comprising a reporter gene, a selection gene, a gene of therapeutic interest or a combination thereof. In some embodiments, no live wild-type helper virus is required for rAAV production and packaging. In some embodiments, expression of E1A is not required for rAAV production. In some embodiments, a minimum of $1.0 \times 10^9$ vg/mL active rAAV is obtained after purification. In some embodiments of the disclosure, rAAV is produced substantially free of replication competent adenovirus (RCA). E.g., in some embodiments of the disclosure, RCA is below the limit of detection before purification. Methods of quantification of virus particles are known to those of skill in the art and can include quantitative polymerase chain reaction (qPCR) analysis, infection titration analysis, endpoint dilution assay, and viral plaque assay. In some embodiments, the inventors have found that the use of SSI to prepare rAAV producer cells ensures the pool of producer cells is homogenous in its genetic makeup. In some embodiments, the inventors have found that the use of SSI to prepare rAAV producer cells ensures the pool of producer cells is homogenous in its efficiency. In some embodiments, the inventors have found that the use of SSI to prepare rAAV producer cells ensures the pool of producer cells is homogenous in the ration of a first helper gene to a second helper gene. In some embodiments, the inventors have found that the use of SSI to prepare rAAV producer cells ensures the pool of producer cells is homogenous in the ratio of helper genes to genes of therapeutic interest. In some embodiments, the inventors have found that the use of SSI to prepare rAAV producer cells ensures more consistent rAAV product quality.

An "amino acid" as used herein refers to a compound containing both a carboxyl (—COOH) and amino (—NH$_2$) group. "Amino acid" refers to both natural and unnatural, i.e., synthetic, amino acids. Natural amino acids, with their three-letter and single letter abbreviations, include alanine (Ala; A); arginine (Arg, R); asparagine (Asn; N); aspartic acid (Asp; D); cysteine (Cys; C); glutamine (Gln; Q); glutamic acid (Glu; E); glycine (Gly; G); histidine (His; H); isoleucine (Ile; I); leucine (Leu; L); lysine (Lys; K); methionine (Met; M); phenylalanine (Phe; F); proline (Pro; P); serine (Ser; S); threonine (Thr; T); tryptophan (Trp; W); tyrosine (Tyr; Y); and valine (Val; V).

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The desired cell line including prokaryotic and/or eukaryotic cell lines can be cultured using any suitable device, facility and methods described herein. Further, in embodiments, the devices, facilities and methods are suitable for culturing suspension cells or anchorage-dependent (adherent) cells and are suitable for production operations configured for production of pharmaceutical and biopharmaceutical products—such as polypeptide products, nucleic acid products (for example DNA or RNA), or mammalian or microbial cells and/or viruses such as those used in cellular and/or viral and microbiota therapies.

In some embodiments, the cells express or produce a product, such as a recombinant therapeutic or diagnostic product. As described in more detail below, examples of products produced by cells include, but are not limited to, antibody molecules (e.g., monoclonal antibodies, bispecific antibodies), antibody mimetics (polypeptide molecules that bind specifically to antigens but that are not structurally related to antibodies such as e.g. DARPins, affibodies, adnectins, or IgNARs), fusion proteins (e.g., Fc fusion proteins, chimeric cytokines), other recombinant proteins (e.g., glycosylated proteins, enzymes, hormones), viral therapeutics (e.g., anti-cancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (such as e.g. siRNA) or DNA (such as e.g. plasmid DNA), antibiotics or amino acids. In embodiments, the devices, facilities and methods can be used for producing biosimilars.

As mentioned, in embodiments, devices, facilities and methods allow for the production of eukaryotic cells, e.g., mammalian cells or lower eukaryotic cells such as for example yeast cells or filamentous fungi cells, or prokaryotic cells such as Gram-positive or Gram-negative cells and/or products of the eukaryotic or prokaryotic cells, e.g., proteins, peptides, antibiotics, amino acids, nucleic acids (such as DNA or RNA), synthesized by the eukaryotic cells in a large-scale manner. In some embodiments, also disclosed are the use of microbial organisms and spores thereof utilized in microbiota therapeutics. Unless stated otherwise herein, the devices, facilities, and methods can include any desired volume or production capacity including but not limited to bench-scale, pilot-scale, and full production scale capacities.

Moreover and unless stated otherwise herein, the devices, facilities, and methods can include any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermenter or fermentation unit, or any other reaction vessel and the term "reactor" is used interchangeably with "fermenter." The term fermenter or fermentation refers to both microbial and mammalian cultures. For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and C02 levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316L or any other suitable stainless steel) and Inconel, plastics, and/or glass.

In embodiments and unless stated otherwise herein, the devices, facilities, and methods described herein can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally and unless otherwise stated, the devices, systems, and methods described herein can be housed and/or performed in a single location or facility or alternatively be housed and/or performed at separate or multiple locations and/or facilities.

By way of non-limiting examples and without limitation, U.S. Publication Nos. 2013/0280797; 2012/0077429; 2011/0280797; 2009/0305626; and U.S. Pat. Nos. 8,298,054; 7,629,167; and 5,656,491, which are hereby incorporated by reference in their entirety, describe example facilities, equipment, and/or systems that may be suitable.

In embodiments, the cells are eukaryotic cells, e.g., mammalian cells. The mammalian cells can be for example human or rodent or bovine cell lines or cell strains. Examples of such cells, cell lines or cell strains are e.g. mouse myeloma (NSO)-cell lines, Chinese hamster ovary (CHO)-cell lines, HT1080, H9, HepG2, MCF7, MDBK Jurkat, NIH3T3, PC12, BHK (baby hamster kidney cell), VERO, SP2/0, YB2/0, Y0, C127, L cell, COS, e.g., COS1 and COS7, QC1-3, HEK293, VERO, PER.C6, HeLa, EB1, EB2, EB3, oncolytic or hybridoma-cell lines. Preferably the mammalian cells are CHO cell lines. In one embodiment, the cell is a CHO cell. In one embodiment, the cell is a CHO-K1 cell, a CHOK1SV™ cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHOK1SV GS-KO (part of Lonza's XCEED® Expression System, Lonza, Slough, UK). The CHO FUT8 knockout cell is, for example, the CHOK1SV™ POTELLIGENT® (Lonza, Slough, UK). Eukaryotic cells can also be avian cells, cell lines or cell strains, such as for example, EBX® cells, EB14, EB24, EB26, EB66, or EBvl3.

In some embodiments, the eukaryotic cells are stem cells. The stem cells can be, for example, pluripotent stem cells, including embryonic stem cells (ESCs), adult stem cells, induced pluripotent stem cells (iPSCs), tissue specific stem cells (e.g., hematopoietic stem cells) and mesenchymal stem cells (MSCs).

In one embodiment, the cell is a differentiated form of any of the cells described herein. In one embodiment, the cell is a cell derived from any primary cell in culture. In some embodiments, the cells are not derived from stem cells. For example, in some embodiments, the cells are used in immunotherapies (e.g., lymphocytes) both extracted and isolated from individual patients or from established cell banks. In some embodiments, the cells can include genetically manipulated cells (i.e. CAR-T, etc.)

In embodiments, the cell is a hepatocyte such as a human hepatocyte, animal hepatocyte, or a non-parenchymal cell. For example, the cell can be a plateable metabolism qualified human hepatocyte, a plateable induction qualified human hepatocyte, plateable QUALYST TRANSPORTER CERTIFIED™ human hepatocyte, suspension qualified human hepatocyte (including 10-donor and 20-donor pooled hepatocytes), human hepatic Kupffer cells, human hepatic stellate cells, dog hepatocytes (including single and pooled Beagle hepatocytes), mouse hepatocytes (including CD-1 and C57Bl/6 hepatocytes), rat hepatocytes (including Sprague-Dawley, Wistar Han, and Wistar hepatocytes), monkey hepatocytes (including Cynomolgus or Rhesus monkey hepatocytes), cat hepatocytes (including Domestic Shorthair hepatocytes), and rabbit hepatocytes (including New Zealand White hepatocytes). Example hepatocytes are commercially available from Triangle Research Labs, LLC, 6 Davis Drive Research Triangle Park, North Carolina, USA 27709.

In one embodiment, the eukaryotic cell is a lower eukaryotic cell such as e.g. a yeast cell (e.g., *Pichia* genus (e.g. *Pichia pastoris, Pichia methanolica, Pichia kluyveri*, and *Pichia angusta*), *Komagataella* genus (e.g. *Komagataella pastoris, Komagataella pseudopastoris* or *Komagataella phaffli*), *Saccharomyces* genus (e.g. *Saccharomyces cerevisiae, Saccharomyces kluyveri, Saccharomyces uvarum*), *Kluyveromyces* genus (e.g. *Kluyveromyces lactis, Kluyveromyces marxianus*), the *Candida* genus (e.g. *Candida utilis, Candida cacaoi, Candida boidinii*), the *Geotrichum* genus (e.g. *Geotrichum fermentans*), *Hansenula polymorpha, Yarrowia lipolytica,* or *Schizosaccharomyces pombe*. Preferred is the species *Pichia pastoris*. Examples for *Pichia pastoris* strains are X33, GS115, KM71, KM71H; and CBS7435.

In one embodiment, the eukaryotic cell is a fungal cell (e.g. *Aspergillus* (such as *A. niger, A. fumigatus, A. orzyae, A. nidula*), *Acremonium* (such as *A. thermophilum*), *Chaetomium* (such as *C. thermophilum*), *Chrysosporium* (such as *C. thermophile*), *Cordyceps* (such as *C. militaris*), *Corynascus, Ctenomyces, Fusarium* (such as *F. oxysporum*), *Glomerella* (such as *G. graminicola*), *Hypocrea* (such as *H. jecorina*), *Magnaporthe* (such as *M. orzyae*), *Myceliophthora* (such as *M. thermophile*), *Nectria* (such as *N. heamatococca*), *Neurospora* (such as *N. crassa*), *Penicillium, Sporotrichum* (such as *S. thermophile*), *Thielavia* (such as *T. terrestris, T. heterothallica*), *Trichoderma* (such as *T. reesei*), or *Verticillium* (such as *V. dahlia*)).

In one embodiment, the eukaryotic cell is an insect cell (e.g., Sf9, MIMIC™ Sf9, Sf21, HIGH FIVE™ (BT1-TN-5B1-4), or BT1-Ea88 cells), an algae cell (e.g., of the genus *Amphora, Bacillariophyceae, Dunaliella, Chlorella, Chlamydomonas, Cyanophyta* (cyanobacteria), *Nannochloropsis, Spirulina*, or *Ochromonas*), or a plant cell (e.g., cells from monocotyledonous plants (e.g., maize, rice, wheat, or *Setaria*), or from a dicotyledonous plants (e.g., cassava, potato, soybean, tomato, tobacco, alfalfa, *Physcomitrella patens* or *Arabidopsis*).

In one embodiment, the cell is a bacterial or prokaryotic cell. In some embodiments, the prokaryotic cell is a Gram-positive cell such as *Bacillus, Streptomyces Streptococcus, Staphylococcus* or *Lactobacillus. Bacillus* that can be used is, e.g. the *B. subtilis, B. amyloliquefaciens, B. licheniformis, B. natto,* or *B. megaterium*. In embodiments, the cell is *B. subtilis*, such as *B. subtilis* 3NA and *B. subtilis* 168. *Bacillus* is obtainable from, e.g., the *Bacillus* Genetic Stock Center, Biological Sciences 556, 484 West 12$^{th}$ Avenue, Columbus Ohio 43210-1214.

In one embodiment, the prokaryotic cell is a Gram-negative cell, such as *Salmonella* spp. or *Escherichia coli*, such as e.g., TG1, TG2, W3110, DH1, DHB4, DH5a, HMS 174, HMS174 (DE3), NM533, C600, HB101, JM109, MC4100, XL1-Blue and Origami, as well as those derived from *E. coli* B-strains, such as for example BL-21 or BL21 (DE3), all of which are commercially available. Suitable host cells are commercially available, for example, from culture collections such as the DSMZ (Deutsche Sammlung von Mikroorganismen and Zellkulturen GmbH, Braunschweig, Germany) or the American Type Culture Collection (ATCC). In some embodiments, the cells include other microbiota utilized as therapeutic agents. These include microbiota present in the human microbiome belonging to the phyla Firmicutes, Bacteroidetes, Proteobacteria, Verrumicrobia, Actinobacteria, Fusobacteria and Cyanobacteria. Microbiota can include both aerobic, strict anaerobic or facultative anaerobic and include cells or spores. Therapeutic Microbiota can also include genetically manipulated organisms and vectors utilized in their modification. Other microbiome-related therapeutic organisms can include: archaea, fungi and virus. See, e.g., The Human Microbiome Project Consortium. *Nature* 486, 207-214 (14 Jun. 2012); Weinstock, *Nature,* 489 (7415): 250-256 (2012); Lloyd-Price, Genome Medicine 8:51 (2016).

In some embodiments, the cultured cells are used to produce proteins e.g., antibodies, e.g., monoclonal antibodies, and/or recombinant proteins, for therapeutic use. In embodiments, the cultured cells produce peptides, amino acids, fatty acids or other useful biochemical intermediates or metabolites. For example, in embodiments, molecules having a molecular weight of about 4000 Daltons to greater than about 140,000 Daltons can be produced. In embodiments, these molecules can have a range of complexity and can include post-translational modifications including glycosylation.

In embodiments, the protein is, e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleulin, denileukin diftitox, interferon alpha-n3 (injection), interferon alpha-ni, DL-8234, interferon, Suntory (gamma-la), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alpha, collagenase, carperitide, recombinant human epidermal growth factor (topical gel, wound healing), DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphnmate, octocog alpha, Factor VIII, palifermin, Indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, Eutropin, KP-102 program, somatropin, mecasermin (growth failure), enlfavirtide, Org-33408, insulin glargine, insulin glulisine, insulin (inhaled), insulin lispro, insulin deternir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alpha, trafermin, ziconotide, taltirelin, diboterminalfa, atosiban, becaplermin, eptifibatide, Zemaira, CTC-11, Shanvac-B, HPV vaccine (quadrivalent), octreotide, lanreotide, ancestirn, agalsidase beta, agalsidase alpha, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant Cl esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alpha-n3 (oral), belatacept, transdermal insulin patches, AMG-531, MBP-8298, Xerecept, opebacan, AID-SVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, rornidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, T-10, ularitide, depelestat, hematide, Chrysalin (topical), rNAPc2, recombinant Factor V111 (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, ACM-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutancous injection, eczema), pitrakinra (inhaled dry powder, asthma), Multikine, RG-1068, MM-093, NBI-6024, AT-001, PI-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alpha-n3 (topical), IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague FIV vaccine, AG-702, OxSODrol, rBetV1, Der-p1/Der-p2/Der-p7 allergen-targeting vaccine (dust mite allergy), PRI peptide antigen (leukemia), mutant ras vaccine, HPV-16 E7 lipopeptide vaccine, labyrinthin vaccine (adenocarcinoma), CML vaccine, WTI-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCRI, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1, AC-162352, PRX-302, LFn-p24 fusion vaccine (Therapore), EP-1043, *S. pneumoniae* pediatric vaccine, malaria vaccine, *Neisseria meningitidis* Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, and TP-9201.

In some embodiments, the polypeptide is adalimumab (HUMIRA), infliximab (REMICADE™), rituximab (RITUXAN™/MABTHERA™) etanercept (ENBREL™), bevacizumab (AVASTIN™), trastuzumab (HERCEPTIN™), pegrilgrastim (NEULASTA™), or any other suitable polypeptide including biosimilars and biobetters.

Other suitable polypeptides are those listed below in Table 6 and in Table 1 of US2016/0097074. One of skill in the art can appreciate that the disclosure of the present invention additional would encompass combinations of products and/or conjugates as described herein [(i.e. multi-proteins, modified proteins (conjugated to PEG, toxins, other active ingredients)].

TABLE 6

| Protein Product | Reference Listed Drug |
|---|---|
| interferon gamma-1b | ACTIMMUNE ® |
| alteplase; tissue plasminogen activator | ACTIVASE ®/CATHFLO ® |
| recombinant antihemophilic factor | ADVATE |
| human albumin | ALBUTEIN ® |
| Laronidase | ALDURAZYME ® |
| interferon alfa-N3, human leukocyte derived | ALFERON N ® |
| human antihemophilic factor | ALPHANATE ® |
| virus-filtered human coagulation factor IX | ALPHANINE ® SD |
| Alefacept; recombinant, dimeric fusion protein LFA3-Ig | AMEVIVE ® |
| Bivalirudin | ANGIOMAX ® |
| darbepoetin alfa | ARANESP ™ |
| Bevacizumab | AVASTIN ™ |
| interferon beta-1a; recombinant | AVONEX ® |
| coagulation factor IX | BENEFIX ™ |
| interferon beta-1b | BETASERON ® |
| Tositumomab | BEXXAR ® |
| antihemophilic factor | BIOCLATE ™ |
| human growth hormone | BIOTROPIN ™ |
| botulinum toxin type A | BOTOX ® |
| Alemtuzumab | CAMPATH ® |
| acritumomab; technetium-99 labeled | CEA-SCAN ® |
| alglucerase; modified form of beta-glucocerebrosidase | CEREDASE ® |
| imiglucerase; recombinant form of beta-glucocerebrosidase | CEREZYME ® |
| crotalidae polyvalent immune Fab, ovine | CROFAB ™ |
| Digoxin immune fab [ovine] | DIGIFAB ™ |
| Rasburicase | ELITEK ® |
| Etanercept | ENBREL ® |
| Epoietin alfa | EPOGEN ® |

TABLE 6-continued

| Protein Product | Reference Listed Drug |
|---|---|
| Cetuximab | ERBITUX ™ |
| Algasidase beta | FABRAZYME ® |
| Urofollitropin | FERINEX ™ |
| Follitropin beta | FOLLISTIM ™ |
| Teriparatide | FORTEO ® |
| Human somatropin | GENOTROPIN ® |
| Glucagon | GLUCAGEN ® |
| Follitropin alfa | GONAL-F ® |
| Antihemophillic factor | HELIXATE ® |
| Antihemophilic factor; Factor XIII | HEMOFIL |
| Adefovir dipivoxil | HEPSERA ™ |
| trastuzumab | HERCEPTIN ® |
| Insulin | HUMALOG ® |
| Antihemophilic factor/von Willebrand factor complex-human | HUMATE-P ® |
| Somatotropin | HUMATROPE ® |
| Adalimumab | HUMIRA ™ |
| Human insulin | HUMULIN ® |
| Recombinant human hyaluronidase | HYLENEX ™ |
| Interferon alfacon-1 | INFERGEN ® |
| Eptifibatide | INTEGRILLIN ™ |
| Alpha-interferon | INTRON A ® |
| Palifermin | KEPIVANCE |
| Anakinra | KINERET ™ |
| Antihemophilic factor | KOGENATE ®FS |
| Insulin glargine | LANTUS ® |
| Granulocyte macrophage colony-simulating factor | LEUKINE ®/LEUKINE ®LIQUID |
| Lutropin alfa for injection | LUVERIS |
| OspA lipoprotein | LYMERIX ™ |
| Ranibizumab | LUCENTIS ® |
| Gemtuzumab ozogamicin | MYLOTARG ™ |
| Galsulfase | NAGLAZYME ™ |
| Nesiritide | NATRECOR ® |
| Pegfilgrastim | NEULASTA ™ |
| Oprelvekin | NEUMEGA ® |
| Filgrastim | NEUPOGEN ® |
| Fanolesomab | NEUTROSPEC ™ (FORMERLY LEUTECH ®) |
| Somatropin [rDNA] | NORDITROPIN ®/NORDITROPIN NORDIFLEX ® |
| Mitoxantrone | NOVANTRONE ® |
| Insulin; zinc suspension | NOVOLIN L ® |
| Insulin; isophane suspension | NO VOLIN N ® |
| Insulin, regular | NOVOLIN R ® |
| Insulin | NOVOLIN ® |
| Coagulation factor VIIa | NOVOSEVEN ® |
| Somatropin | NUTROPIN ® |
| Immunoglobulin intravenous | OCTAGAM ® |
| PEG-L-asparaginase | ONCASPAR ® |
| Abatacept, fully human soluable fusion protein | ORENCIA ™ |
| Muromomab-CD3 | ORTHOCLONE OKT3 ® |
| High-molecular weight hyaluronan | ORTHOVISC ® |
| Human chorionic gonadotropin | OVIDREL ® |
| Live attenuated *Bacillus* Calmette-Guerin | PACIS ® |
| Peginterferon alfa-2a | PEGASYS ® |
| Pegylated version of interferon alfa-2b | PEG-INTRON ™ |
| Abarelix (Injection suspension); gonadotropin-releasing hormone antagonist | PLENAXIS ™ |
| Epoietin alfa | PROCRIT ® |
| Aldesleukin | PROLEUKIN, IL-2 ® |
| Somatrem | PROTROPIN ® |
| Dornase alfa | PULMOZYME ® |
| Efalizumab; selective, reversible T-cell blocker | RAPTIVA ™ |
| Combination of ribavirin and alpha interferon | REBETRON ™ |
| Interferon beta 1a | REBIF ® |
| Antihemophilic factor | RECOMBINATE ® RAHF |
| Antihemophilic factor | REFACTO ® |
| Lepirudin | REFLUDAN ® |
| Infliximab | REMICADE ® |
| Abciximab | REOPRO ™ |
| Reteplase | RETAVASE ™ |
| Rituxima | RITUXAN ™ |
| Interferon alfa-2[a] | ROFERON-A ® |
| Somatropin | SAIZEN ® |
| Synthetic porcine secretin | SECREFLO ™ |
| Basiliximab | SIMULECT ® |
| Eculizumab | SOLIRIS ® |
| Pegvisomant | SOMAVERT ® |

TABLE 6-continued

| Protein Product | Reference Listed Drug |
|---|---|
| Palivizumab; recombinantly produced, humanized mAb | SYNAGIS ™ |
| Thyrotropin alfa | THYROGEN ® |
| Tenecteplase | TNKASE ™ |
| Natalizumab | TYSABRI ® |
| Human immune globulin intravenous 5% and 10% solutions | VENOGLOBULIN-S ® |
| Interferon alfa-n1, lymphoblastoid | WELLFERON ® |
| Drotrecogin alfa | XIGRIS ™ |
| Omaluzumab; recombinant DNA-derived humanized monoclonal antibody targeting immunoglobulin-E | XOLAIR ® |
| Daclizumab | ZENAPAX ® |
| Ibritumomab tiuxetan | ZEVALIN ™ |
| Somatotropin | ZORBTIVE ™ (SEROSTIM ®) |

In embodiments, the polypeptide is a hormone, blood clotting/coagulation factor, cytokine/growth factor, antibody molecule, fusion protein, protein vaccine, or peptide as shown in Table 7.

TABLE 7

Exemplary Products

| Therapeutic Product type | Product | Trade Name |
|---|---|---|
| Hormone | Erythropoietin, Epoein-α | Epogen, Procrit |
| | Darbepoetin-α | Aranesp |
| | Growth hormone (GH), somatotropin | Genotropin, Humatrope, Norditropin, NovIVitropin, Nutropin, Omnitrope, Protropin, Siazen, Serostim, Valtropin |
| | Human follicle-stimulating hormone (FSH) | Gonal-F, Follistim |
| | Human chorionic gonadotropin | Ovidrel, Luveris |
| | Lutropin-α | GlcaGen |
| | Glucagon | Geref |
| | Growth hormone releasing hormone (GHRH) | ChiRhoStim (human peptide), SecreFlo (porcine peptide) |
| | Secretin | |
| | Thyroid stimulating hormone (TSH), thyrotropin | Thyrogen |
| Blood Clotting/ Coagulation Factors | Factor VIIa | Novo Seven |
| | Factor VIII | Bioclate, Helixate, Kogenate, Recombinate, ReFacto |
| | Factor IX | Benefix |
| | Antithrombin III (AT-III) | Thrombate III |
| | Protein C concentrate | Ceprotin |
| Cytokine/Growth factor | Type I alpha-interferon | Infergen |
| | Interferon-αn3 (IFNαn3) | Alferon N |
| | Interferon-β1a (rIFN-β) | Avonex, Rebif |
| | Interferon-β1b (rIFN-β) | Betaseron |
| | Interferon-γ1b (IFN γ) | Actimmune |
| | Aldesleukin (interleukin 2(IL2), epidermal theymocyte activating factor; ETAF | Proleukin |
| | Palifermin (keratinocyte growth factor; KGF) | Kepivance |
| | Becaplemin (platelet-derived growth factor; PDGF) | Regranex |
| | Anakinra (recombinant IL1 antagonist) | Anril, Kineret |
| Antibody molecules | Bevacizumab (VEGFA mAb) | Avastin, Erbitux |
| | Cetuximab (EGFR mAb) | Vectibix |
| | Panitumumab (EGFR mAb) | Campath |
| | Alemtuzumab (CD52 mAb) | Rituxan |
| | rituximab (CD20 chimeric Ab) | Herceptin, Orencia |
| | Trastuzumab (HER2/Neu mAb) | Humira, Enbrel |
| | Abatacept (CTLA Ab/Fc fusion) | Remicade |
| | Adalimumab (TNFα mAb) | Amevive |
| | Etanercept (TNF receptor/Fc fusion) | Raptiva, Tysabri |
| | Infliximab (TNFα chimeric mAb) | Soliris, Orthoclone, OKT3 |
| | Alefacept (CD2 fusion protein) | |
| | Efalizumab (CD11a mAb) | |

TABLE 7-continued

Exemplary Products

| Therapeutic Product type | Product | Trade Name |
|---|---|---|
| | Natalizumab (integrin α4 subunit mAb) | |
| | Eculizumab (C5mAb) | |
| | Muromonab-CD3 | |
| Other: | Insulin | Humulin, Novolin |
| | Hepatitis B surface antigen (HBsAg) | Engerix, Recombivax HB |
| | HPV vaccine | Gardasil |
| Fusion proteins/Protein vaccines/Peptides | OspA | LYMErix |
| | Anti-Rhesus(Rh) immunoglobulin G | Rhophylac |
| | Enfuvirtide | Fuzeon |
| | Spider silk, e.g., fibrion | QMONOS |

In embodiments, the protein is multispecific protein, e.g., a bispecific antibody as shown in Table 8.

TABLE 8

Bispecific Formats

| Name (other names, sponsoring organizations) | BsAb format | Targets | Proposed mechanisms of action | Development stages | Diseases (or healthy volunteers) |
|---|---|---|---|---|---|
| Catumaxomab (REMOVAB ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech, Fresenius Biotech) | BsIgG: Triomab | CD3, HER2 | Retargeting of T cells to tumor | Phase I/II | Advanced solid tumors |
| Blinatumomab (BLINCYTO ®, AMG 103, MT 103, MEDI 538, Amgen) | BiTE | CD3, CD19 | Retargeting of T cells to tumor | Approved in USA Phase II and III Phase II Phase I | Precursor B-cell ALL ALL DLBCL NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adenocancinoma |
| RO6958688 (Roche) | BsAb | CD3, CEA | | | |
| BAY2010112 (AMG 212, Bayer; Amgen) | BiTE | CD3, PSMA | Retargeting of T cells to tumor | Phase I | Prostate cancer |
| MGD006 (Macrogenics) | DART | CD3, CD123 | Retargeting of T cells to tumor | Phase I | AML |
| MGD007 (Macrogenics) | DART | CD3, gpA33 | Retargeting of T cells to tumor | Phase I | Colorectal cancer |
| MGD011 (Macrogenics) | DART | CD19, CD3 | | | |
| SCORPION (Emergent Biosolutions, Trubion) | BsAb | CD3, CD19 | Retargeting of T cells to tumor | | |
| AFM11 (Affimed Therapeutics) | TandAb | CD3, CD19 | Retargeting of T cells to tumor | Phase I | NHL and ALL |
| AFM12 (Affimed Therapeutics) | TandAb | CD19, CD16 | Retargeting of NK cells to tumor cells | | |
| AFM13 (Affimed Therapeutics) | TandAb | CD30, CD16A | Retargeting of NK cells to tumor cells | Phase II | Hodgkin's Lymphoma |

TABLE 8-continued

Bispecific Formats

| Name (other names, sponsoring organizations) | BsAb format | Targets | Proposed mechanisms of action | Development stages | Diseases (or healthy volunteers) |
|---|---|---|---|---|---|
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |
| Anti-EGFR-armed activated T-cells (Barbara Ann Karmanos Cancer Institute) | T cells preloaded with BsAb | CD3, EGFR | Autologous activated T cells to EGFR-positive tumor | Phase I | Colon and pancreatic cancers |
| rM28 (University Hospital Tübingen) | Tandem scFv | CD28, MAPG | Retargeting of T cells to tumor | Phase II | Metastatic melanoma |
| IMCgp100 (Immunocore) | ImmTAC | CD3, peptide MHC | Retargeting of T cells to tumor | Phase I/II | Metastatic melanoma |
| DT2219ARL (NCI, University of Minnesota) | 2 scFv linked to diphtheria toxin | CD19, CD22 | Targeting of protein toxin to tumor | Phase I | B cell leukemia or lymphoma |
| XmAb5871 (Xencor) | BsAb | CD19, CD32b | | | |
| NI-1701 (NovImmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II Phase II | Head and neck cancer Colorectal cancer |
| LY3164530 (Eli Lily) | Not disclosed | EGFR, MET | Blockade of 2 receptors | Phase I | Advanced or metastatic cancer |
| MM-111 (Merrimack Pharmaceuticals) | HSA body | HER2, HER3 | Blockade of 2 receptors | Phase II Phase I | Gastric and esophageal cancers Breast cancer |
| MM-141, (Merrimack Pharmaceuticals) | IgG-scFv | IGF-1R, HER3 | Blockade of 2 receptors | Phase I | Advanced solid tumors |
| RG7221 (RO5520985, Roche) | CrossMab | Ang2, VEGFA | Blockade of 2 proangiogenics | Phase I | Solid tumors |
| RG7716 (Roche) | CrossMab | Ang2, VEGFA | Blockade of 2 proangiogenics | Phase I | Wet AMD |
| OMP-305B83 (OncoMed) | BsAb | DLL4/VEGF | | | |
| TF2 (Immunomedics) | Dock and lock | CEA, HSG | Pretargeting tumor for PET or radioimaging | Phase II | Colorectal, breast and lung cancers |
| ABT-981 (AbbVie) | DVD-Ig | IL-1α, IL-1β | Blockade of 2 proinflammatory cytokines | Phase II | Osteoarthritis |
| ABT-122 (AbbVie) | DVD-Ig | TNF, IL-17A | Blockade of 2 proinflammatory cytokines | Phase II | Rheumatoid arthritis |
| COVA322 | IgG-fynomer | TNF, IL17A | Blockade of 2 proinflammatory cytokines | Phase I/II | Plaque psoriasis |
| SAR156597 (Sanofi) | Tetravalent bispecific tandem IgG | IL-13, IL-4 | Blockade of 2 proinflammatory cytokines | Phase I | Idiopathic pulmonary fibrosis |

TABLE 8-continued

Bispecific Formats

| Name (other names, sponsoring organizations) | BsAb format | Targets | Proposed mechanisms of action | Development stages | Diseases (or healthy volunteers) |
|---|---|---|---|---|---|
| GSK2434735 (GSK) | Dual-targeting domain | IL-13, IL-4 | Blockade of 2 proinflammatory cytokines | Phase I | (Healthy volunteers) |
| Ozoralizumab (ATN103, Ablynx) | Nanobody | TNF, HSA | Blockade of proinflammatory cytokine, binds to HSA to increase half-life | Phase II | Rheumatoid arthritis |
| ALX-0761 (Merck Serono, Ablynx) | Nanobody | IL-17A/F, HSA | Blockade of 2 proinflammatory cytokines, binds to HSA to increase half-life | Phase I | (Healthy volunteers) |
| ALX-0061 (AbbVie, Ablynx; | Nanobody | IL-6R, HSA | Blockade of proinflammatory cytokine, binds to HSA to increase half-life | Phase I/II | Rheumatoid arthritis |
| ALX-0141 (Ablynx, Eddingpharm) | Nanobody | RANKL, HSA | Blockade of bone resorption, binds to HSA to increase half-life | Phase I | Postmenopausal bone loss |
| RG6013/ACE910 (Chugai, Roche) | ART-Ig | Factor IXa, factor X | Plasma coagulation | Phase II | Hemophilia |

To realize the benefit of the system for therapeutic proteins, the CHOK1SV SSI comprising multiple RTS sites can be tested for the expression of therapeutic proteins as outlined in Table 10. Experiments can be separated into three phases; Phase 1: Tests the application of multisite SSI to increase qP; Phase 2: Tests the capability of multisite SSI to express a three-gene bispecific mAb across the two SSIS; Phase 3: To express ancillary genes in one site in order to aid the expression of a DtE protein encoded in the other site.

Phase 1:

The limitation of some cell lines comprising a single RTS site is that a single copy of the necessary transcription units is not sufficient to generate suitable titers for clinical manufacturing. Therefor we can evaluate the option to use multiple RTS to increase the integrated copy number of mAb genes. In such an approach mAb genes can be targeted to both landing pads A and B. The homogeneity of the pool can be determined by FACS sorting and analysis of supernatants by Protein A HPLC.

Phase 2:

For the majority of next generation antibodies (e.g. tetravalent bispecific antibodies) the assembly of multiple heavy or light chains is a recurrent problem. In order to obtain optimal product quality with very few unwanted side products, the selection of an appropriate CHO clone expressing as many as four antibody chains in a stable and reproducible is beneficial. As a result, a large amount of product analytics utilizing ELISAs, RP-HPLC or CD-SDS during clone selection is often required. However, in a cell line comprising multiple RTS, the genes encoding a multi chain protein are separated across two sites spatially with individual promoters. This ensure that copy number and relative expression of individual chains are consistent as early as transfectant pools and enabling empirical fine-tuning of the availability of individual polypeptide chains through promoter strength or copy number manipulation of the encoding transcription units. The advantage of this are that product quality is more consistent, reducing the proportion of misfolded multichain recombinant protein produced from SSI-generated pools and cell lines, dramatically recuing the need for early stage assessments. Test molecule: cergutumab amunaleukin.

Phase 3:

Expression of endogenous proteins which results in the expansion of the secretion capacity of the CHOK1SV GS-KO™ cell line is a proven approach to increase product titers. Candidates can be identified from PCT application WO2015018703 A1 and those in Tables 9 and 10 can be evaluated on a cell line comprising multiple distinct recombination target sites (RTS). Product titers can be measured by Protein A HPLC and antibody assembly can be assessed by SDS-PAGE and IEF. Tets molecule: Rituximab, cB72.3, infliximab and Etanercept.

TABLE 9

| Phase | Rational | Therapeutic protein | Ancillary Gene |
|---|---|---|---|
| 1 | mAb genes in multiple SSIS to increase qP | Rituximab, cB72.3 and H31K5 etc. | N/A |
| 2 | Bispecific mAb and >2 chain DtE genes expressed from SSIS | Cergutuzumab amunaleukin etc. | N/A |
| 3 | Ancillary gene expression to increase product quality of DtE | Infliximab etc. | Lipid genes from Candidates identified in U.S. application No. 62/322,621, incorporated herein by reference, the miRNA sponge vectors as found in FIG. 20, and any blood factor proteases. |

TABLE 10

| miR | Target Gene (miR binding site in 3'UTR) | Sponge Sequence (miR Target Sequence in Gene 3'UTR) | Copies of 3'UTR target site |
|---|---|---|---|
| miR-15b and miR-16-1 | CPEB2A | 5'-aggggcaacaca gtctgctgcta-3' (SEQ ID NO: 38) | 1, 3, 6, 9 and 12 |
| miR-15b and miR-16-1 | CPEB2B | 5'-aagctgtattag ctttgctgcta-3' (SEQ ID NO: 39) | |
| miR-34c | SRPRα | 5'-taatcatgttac aatcactgcc-3' (SEQ ID NO: 40) | |
| miR-708 | CNTFR | 5'-caccatcagatt ataagctcctg-3' (SEQ ID NO: 41) | |
| miR-186 | EIF3A | 5'-cagtctaaattg aattcttta-3' (SEQ ID NO: 42) | |

EXAMPLES

Figure 6:
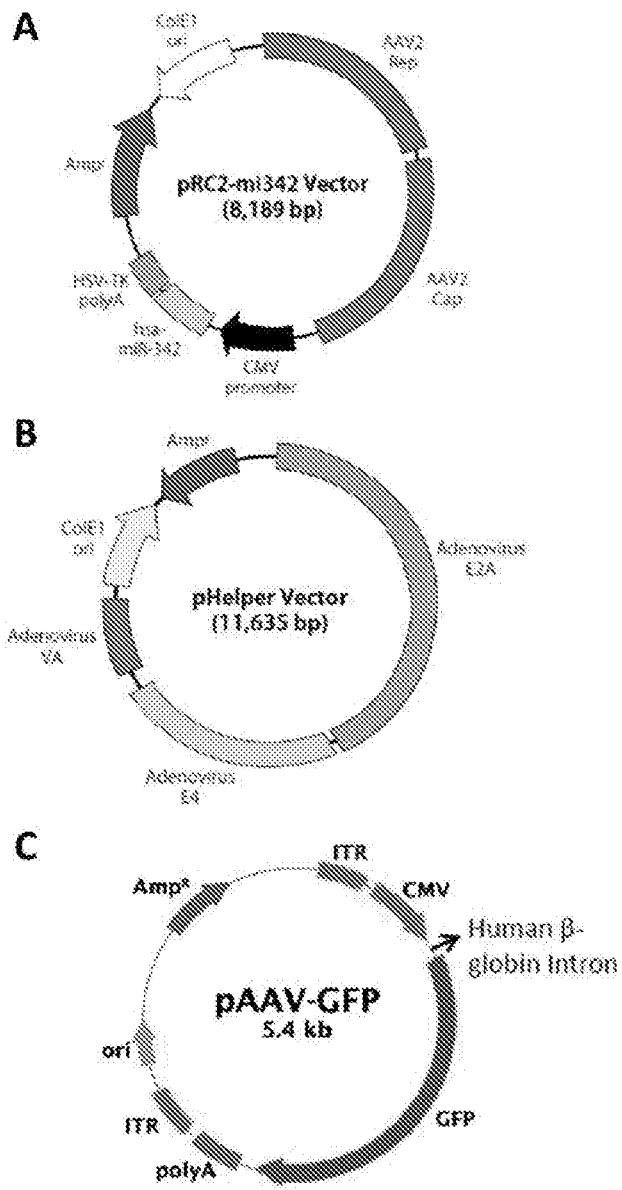
FIG. 6 shows a vector diagram of pRC2-miRNA342 (6234, Clontech) (FIG. 6A), pHelper (6234, Clontech) (FIG. 6B) and pAAV-GFP (AAV-400, Cell Biolabs) (FIG. 6C).

Example 1: Transient AAV Production in CHOK1SV GS-KO™ with Adenovirus 5 Virus Co-Infection To determine whether CHOK1SV GS-KO™ (Lonza, Slough, UK) cells are biologically capable of producing and assembling rAAV vector proteins, CHOK1SV GS-KO™ cells were transfected with two plasmids—pRC2-mi342 (6234, Clontech) and pAAV-GFP (AAV-400, Cell Biolabs) Control Vector (Catalogue number: AAV-400 Cell Biolabs, San Diego, USA) (FIG. 6), in presence of wt Ad5 virus (Catalogue Number: ATCC® VR-1516™, American Type Culture Collection, Manassas, USA). Under natural conditions, CHOK1SV GS-KO™ cells are not receptive to adenovirus since they lack the viral receptor, however, in presence of cationic transfection reagents (lipofectamine or PEI); the negatively charged adenovirus 5 is able to enter the CHOK1SV GS-KO™ cells, thus providing all the helper elements. This concept was used in designing this evaluation experiment where the CHOK1SV GS-KO™ cells were provided all the elements (Rep-Cap and GOI by transfection and Ad5 elements by infection). Cells were harvested 72 hours post-transfection/infection and lysed by going through 4 freeze/thaw cycles, followed by a benzonase treatment to digest any plasmid DNA. The lysate was tested by qPCR for AAV titer, as well as tested for transduction efficiency of HEK293 for transgene (green fluorescent protein—GFP) expression. As a control for this experiment, adherent HEK293 cells were used and cell lysates from a HEK293 triple transfection (pHelper (6234, Clontech), pRC2-mi342 (6234, Clontech), pAAV-GFP (AAV-400, Cell Biolabs) (FIG. 6)) was analyzed the same as for CHOK1SV GS-KO™ cells transfected with pRC2-mi342 (6234, Clontech), pAAV-GFP and infected with wt Ad5. The experimental outline and results from this experiment are presented in FIG. 1. Green fluorescence was detected in CHOK1SV GS-KO™ cells following transfection, indicating successful transfection (FIG. 1B, left panel). The lysate from in CHOK1SV GS-KO™ cells following transfection was used to transduce HEK293 cells, and green fluorescence was detected in HEK293 cells, albeit low (FIG. 1B, right panel), suggesting low level production of AAV. The qPCR data shows an AAV titer of 6.8E+09 vg/mL (FIG. 1C). The positive control, HEK293 with triple transfection produced a higher AAV titer of 1.8e+12 as expected and no AAV was produced in the negative control, HEK293 GFP transfection. To summarize, this is first known experiment, showing that CHOK1SV GS-KO™ cells are capable of producing AAV when provided with all known genomic elements required for AAV packaging.

Figure 2:
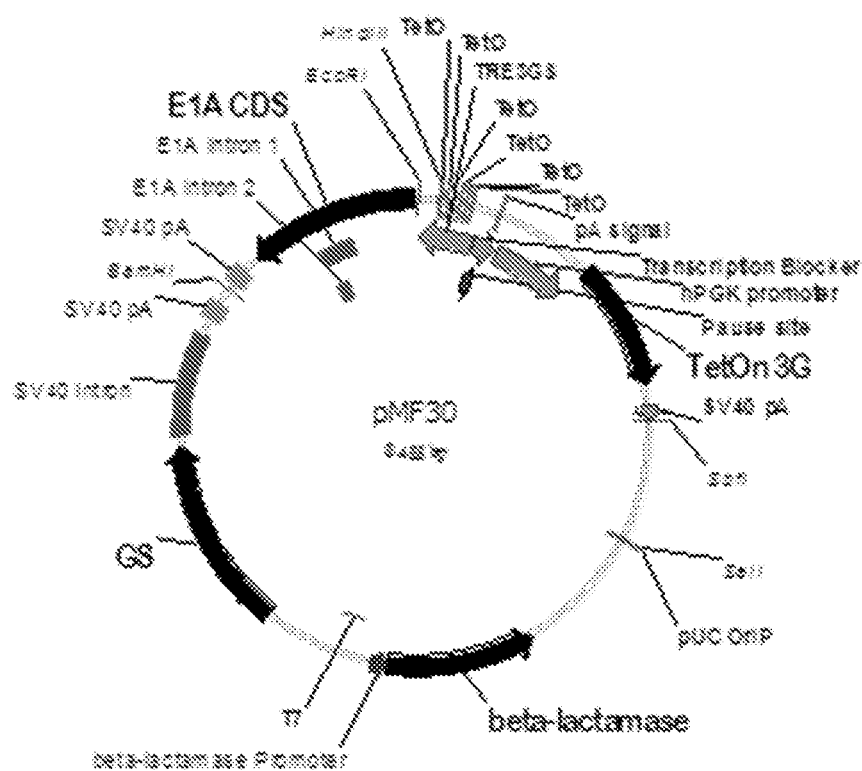
FIG. 2 shows a pMF30 vector diagram. E1A in a TET inducible vector bearing a GS selection marker.
Figure 3:
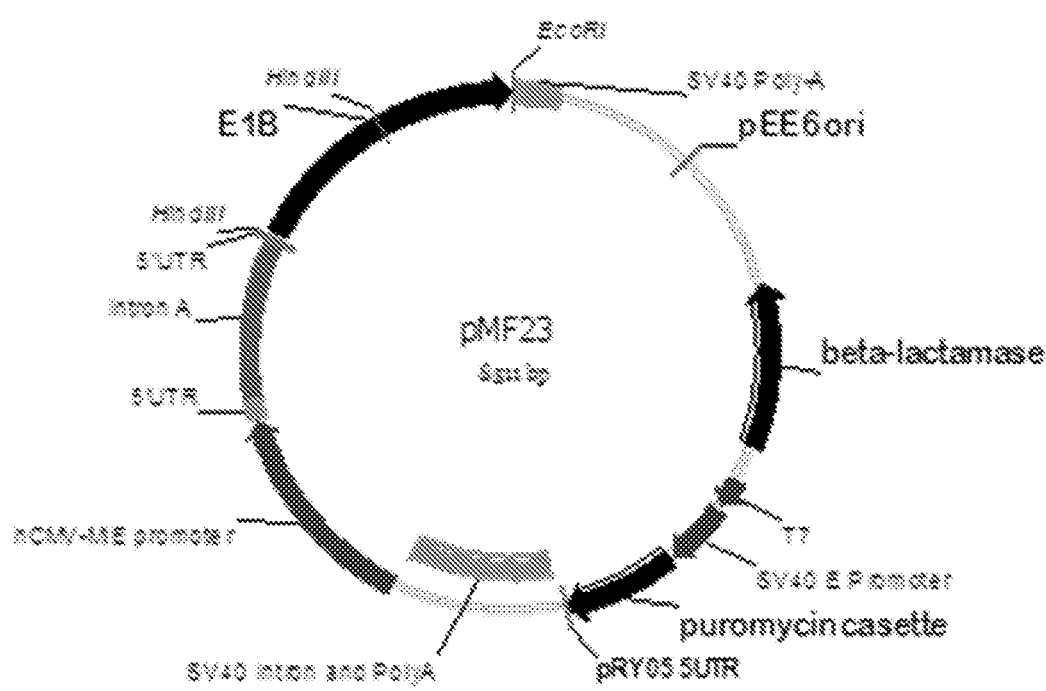
FIG. 3 shows a pMF23 vector diagram. E1B in a constitutive vector bearing a PAC selection marker.
Figure 4:
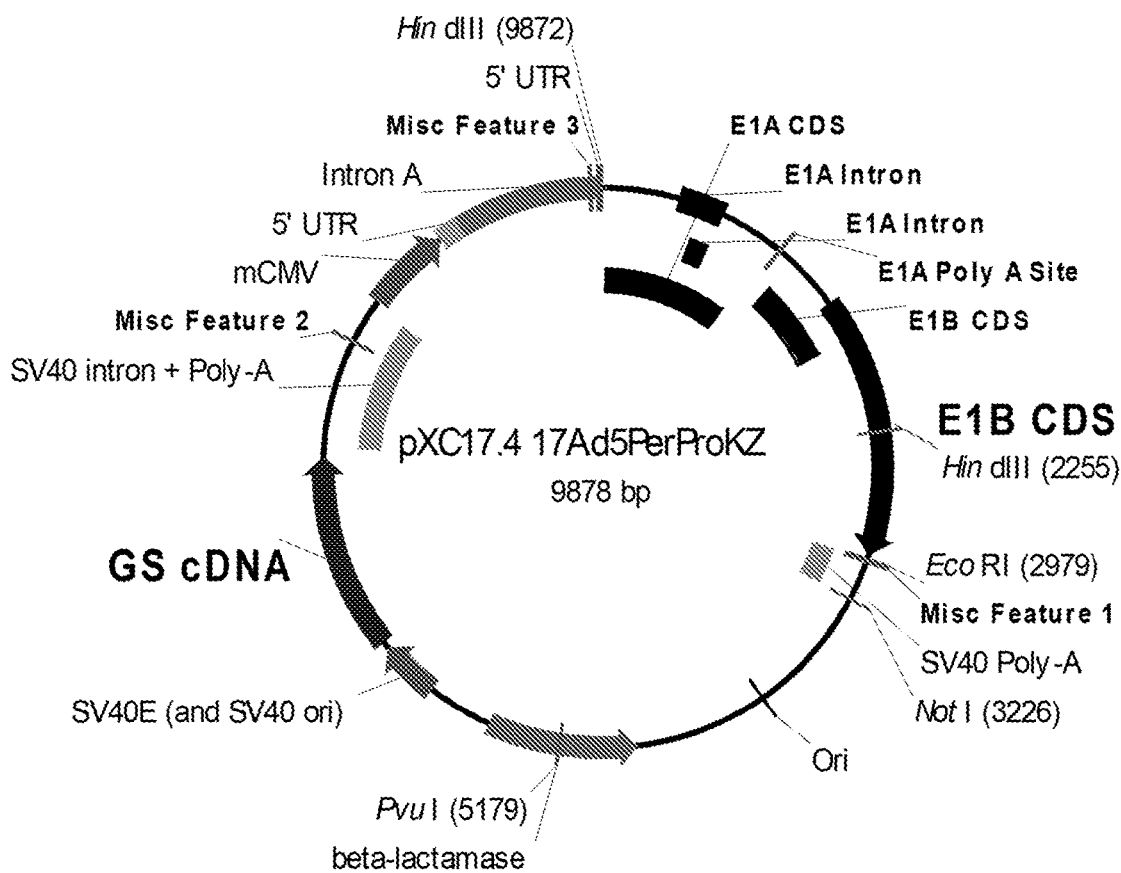
FIG. 4 shows a pXC17.4_17Ad5PerProKZ vector diagram. E1A and E1B was expressed from a single promoter (viral regulatory regions between the two gene and the viral promoter region (nucleotides 498-3635) located between E1A and E1B coding sequence were retained) as described by Qiao et al., *J. Virol.* 76:1904-13 (2002). Annotation matches co-ordinates described in Qiao et al., *J. Virol.* 76:1904-13 (2002).
Figure 5:
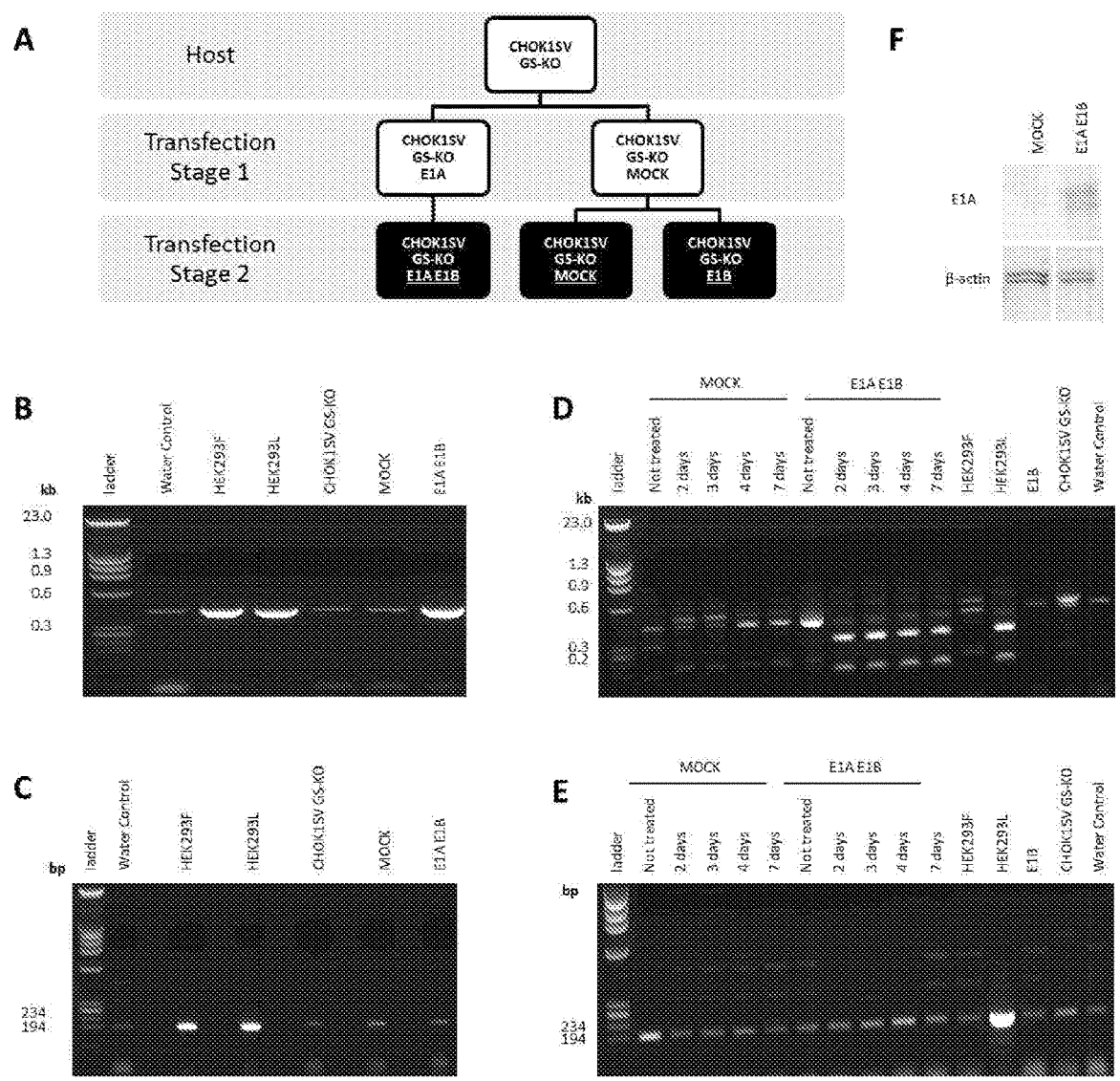
FIG. 5 shows construction of CHOK1SV GS-KO™ pools expressing wt Ad5 E1A and E1B to enable rAAV production in these cells the absence of helper virus.

Example 2: Transient rAAV Production in CHOK1SV GS-KO™ without Virus Co-Infection To determine whether CHOK1SV GS-KO™ cells are capable of producing rAAV in the absence of wt Ad5 virus, cells were engineered to express Ad5 E1A and E1B in a similar approach to Howe et al., 2005. Plasmid constructs were created which express E1A under the control of a TET-on promoter (pMF30, FIG. 2), E1B under the control of a constitutive human CMV promoter (pMF23, FIG. 3) and the Ad5 E1A-E1B open reading frame (pXC17.4_17AV5PerProKZ, FIG. 4). CHOK1SV GS-KO™ derived pools were created by transfecting with pMF30 and selecting for those cells which are able to survive in glutamine-free media supplemented with 50 μM L-MSX (FIG. 5A). This CHOK1SV GS-KO™ E1A was then transfected with pMF23 and selecting for those cells which are able to survive in glutamine-free media supplemented with 50 μM L-MSX and 10 μg/mL Puromycin (FIG. 5A). The water control was contaminated in all of the genomic DNA PCRs, but it is clear that E1A PCR products were amplified in HEK293F and HEK293L cells and pXC17.4_17AV5PerProKZ (FIG. 1B). CHOK1SV GS-KO™ MOCK (MOCK) and CHOK1SV GS-KO™ E1A E1B (E1A E1B) pools were treated with doxycycline (2 μg/ml) to activate the TET promoter and E1A transcription for 0 (not treated), 2, 3, 4 and 7 days, and then the mRNA was isolated for reverse-transcription PCR using primers for E1A (FIG. 1D) and E1B (FIG. 1E). Results show a higher level of E1A 243R and E1A 171R in CHOK1SV GS-KO™ E1A E1B pools treated with doxycycline and in HEK293L cells. The amount of E1B mRNA product did not change following doxycycline treatment, but was noticeably higher in HEK293L cells. E1A protein was detected in CHOK1SV GS-KO™ E1A E1B pool treated with doxycycline for 7 days (E1A E1B), and was not detectable in CHOK1SV GS-KO™ MOCK (MOCK) protein lysates (FIG. 5F). This pool CHOK1SV GS-KO™ E1A_E1B was then tested for the ability to produce rAAV with and without Doxycycline (2 μg/ml). To ensure a high expression of E1A and E1B protein, transient transfection of E1A-E1B plasmid (pXC17.4_17AV5PerProKZ, FIG. 4) in CHOK1SV GS-KO™ cells was also performed. These data show that E1A protein expression can be achieved in CHO without the requirement for wt Ad infection. Confirmation of E1B integration and expression was more challenging.

Figure 7:
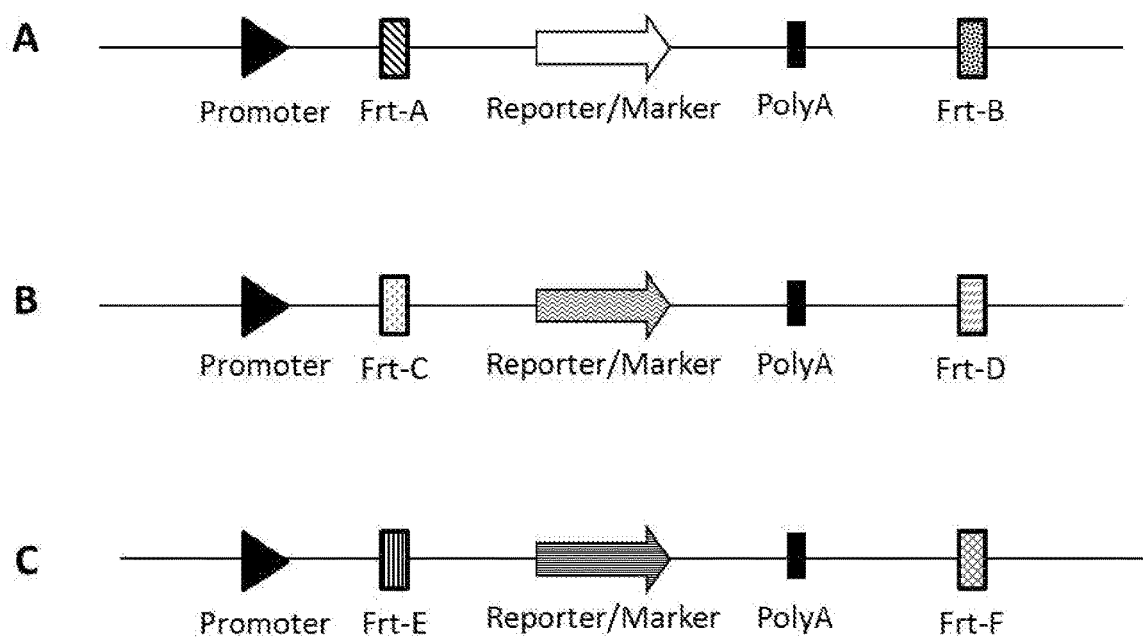
FIG. 7 shows a schematic for three independently addressable site-specific integration sites (SSIS) in CHOK1SV GS-KO™ and HEK293 site-specific integration cell line.
Figure 8:
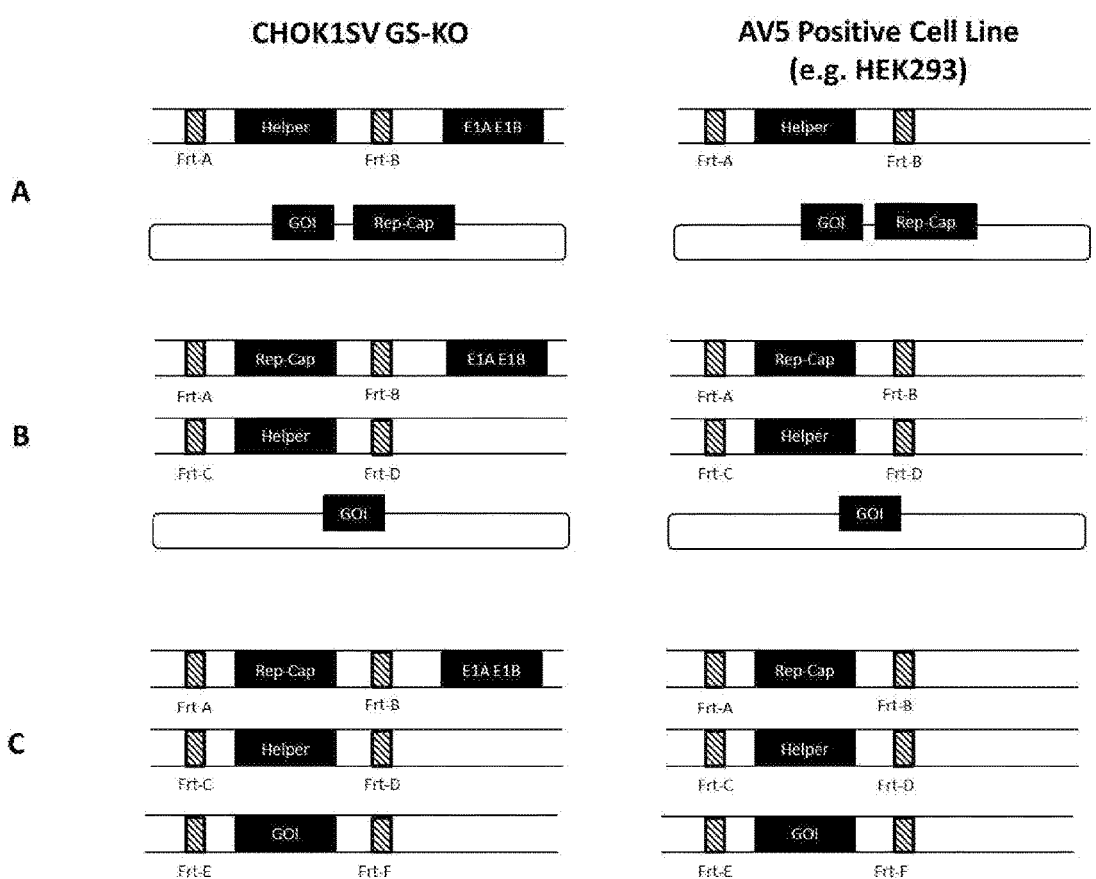
FIG. 8 shows a system schematic for a method of preparing CHOK1SV GS-KO™-AAV producer cells. The SSISs are used for introducing adenovirus (Ad) genes (helper genes), the AAV genes (Rep/Cap) and the AAV vector cassette (e.g. ITR-GOI-ITR), and in CHOK1SV GS-KO™ additional Ad genes (E1A/E1B) are introduced elsewhere with an inducible promoter. In this instance Frt sites A-F could be any of those described in Table 2.

Example 3: Permanent rAAV Production in CHOK1SV GS-KO™ and HEK293 without Virus Co-Infection Landing pads suitable for subsequent RMCE were integrated into the CHOK1SV GS-KO™ and HEK293 genome as loci identified from recombinant CHOK1SV™ cell lines (Fer1L4, NL1, 2, 3, 4, 5 and 6 (see, e.g., WO2013190032A1 and EP2711428A1)). A schematic of the arrangement of elements within these landing pads is presented in FIGS. 7A, B and C). The positioning of the Frt sites between the SV40E promoter and selection marker enables it be used in subsequent rounds of RMCE. The use of incompatible Frt sites (A, B, C, D, E, and F) and a different report/selection marker ensures sites are independently addressable. FIG. 8 shows the various arrangements of AAV, Ad5 and GOI genes following RMCE in 1 (FIG. 8A), 2 (FIG. 8B) and 3 (FIG. 8C) site CHO- and HEK293-derived SSI cells lines.

In order to generate a HEK293 SSI host, CHOK1SV derived vector integration sites and landing pad locations were BLAT searched against the human genome (version: March 2006 (NCBI36/hg18)) using a stand-alone copy of the University of California Santa Cruz (UCSC) human genome data base. This identifies sequences of 95% (and greater) similarity, in at least 25 base pairs of CHOK1SV sequence. Regions of similarity were visualized in IGV viewer (Broad institute version 2.4). Crispr-Cas9 gRNA were design using an in house Crispr-Cas9 design tool. CHOK1SV and HEK293 loci are summarized in Table A.

Example 4: Ancillary Gene Expression to Enhance rAAV Production in CHOK1SV GS-KO™

The mammalian innate immune system senses viral infection by recognizing viral signatures and activates potent antiviral responses (e.g. RIG-1 IFNα response). There is accumulating evidence that RNA silencing or RNA interference (RNAi) serves as an antiviral mechanism in mammalian cells. Mammalian viruses encode IFN antagonists such as the influenza NS1 protein and Vaccinia virus E3L protein, see e.g. de Vries et al, *Gene Ther.*, 15:545-52 (2008), which inhibit PKR, and Vaccinia virus-encoded soluble IFN-alpha/beta receptor decoys counteract the IFN response in infected cells. The co-expression of IFN antagonists can be investigated as a possible approach to overcome poor Ad5 and AAV genes expression observed in Examples 2 and 3.

Example 5: rAAV Production in CHOK1SV GS-KO™ Using Site Specific Integration

Section 1: Construction of Dual Landing Pad CHOK1SV GS-KO™ SSI Host

Figure 9:
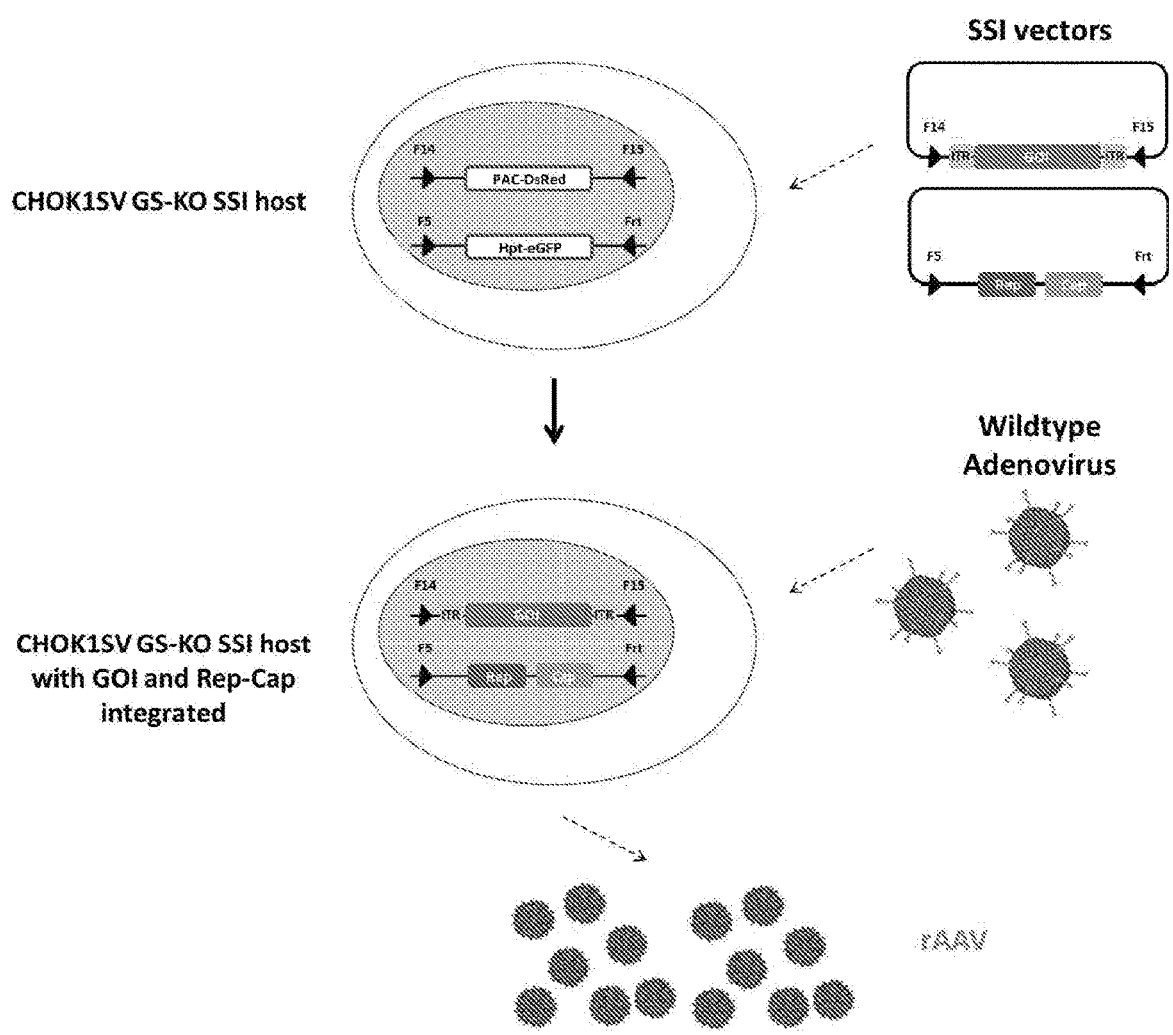
FIG. 9 shows a schematic of rAAV production in a CHOK1SV GS-KO™ site-specific integration (SSI) host utilizing site-specific integration of a GOI and Rep/Cap genes at different sites. To produce rAAV, a CHOK1SV GS-KO™ SSI host was infected with wt Ad5 to provide the helper gene functions required for rAAV replication.

The CHOK1SV GS-KO™ SSI host was created by inserting two landing pads in the genome of the CHOK1SV GS-KO™ host (FIG. 9). Landing pad A is located in the Fer1L4 gene (see Table 10) and is composed of SV40 early promoter (SV40E), hygromycin phosphotransferase-eGFP fusion gene (Hpt-eGFP) and SV40 polyadenylation sequence (pA). The Hpt-eGFP gene and SV40 pA are flanked by incompatible Frt sites (Frt_5 and Frt_wt, respectively) to facilitate RMCE of recombinant genes into the CHOK1SV GS-KO™ genome. Landing pad B is located in the NL1 locus (see Table A) and is composed of SV40 early promoter (SV40E), puromycin N-acetyltransferase-DsRed fusion gene (PAC-DsRed) and SV40 polyadenylation sequence (pA). The PAC-DsRed gene and SV40 pA are flanked by incompatible Frt sites (Frt14 and Frt1S5, respectively). In both landing pads the positioning of a Frt site between the SV40E promoter and selection marker enable it to be used in subsequent rounds of RMCE. Targeting vectors designed for RMCE in the CHOK1SV GS-KO™ SSI host contain a positive selection marker (e.g. GS) arranged immediately to the 3' of a Frt site compatible with the destination landing pad (FIG. 9). The remainder of the vector contains transcription units for the GOI followed by a Frt site compatible to the second Frt site in the landing pad.

Figure 10:
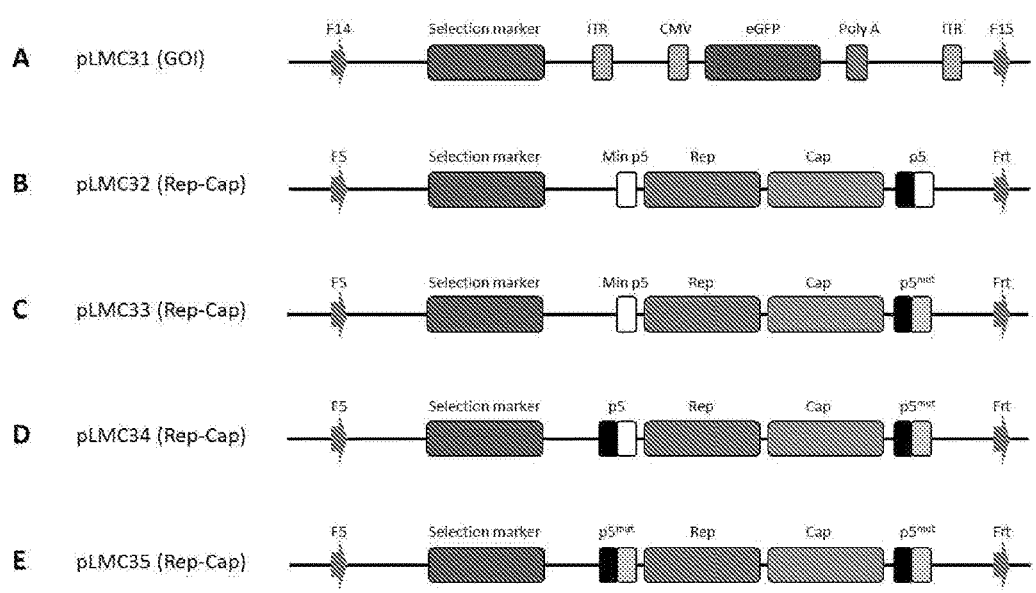
FIG. 10 shows a schematic of the GOI vector and four designs of Rep/Cap genes for site-specific integration in the CHOK1SV GS-KO™ host. All vectors were flanked by two Frt sites to allow for SSI into a CHOK1SV GS-KO™ SSI host cell.

Targeting vector DNA (FIG. 10) is co-transfected with a vector expressing Flp recombinase. Transfected cells are incubated for 24 hours and selection pressure is then applied (e.g. removal of glutamine from culture medium). Successful RMCE is marked by the loss of the Hpt-eGFP or PAC-DsRed gene and replacement with the positive selection marker gene. Cells appear dark under the fluorescent microscope or with flow cytometer analysis. Non-exchanged cells which recover in positive selection are easily removed by FACS.

Section 2: Construction of Rep-Cap and GOI Expression Vectors Compatible with the CHOK1SV GS-KO™ SSI Host To generate CHOK1SV GS-KO™ SSI host derived pools expressing both Rep-Cap and GOI genes (FIG. 9), five vectors were designed (pLMC31-35, FIG. 10A to E). pLMC31 (FIG. 10A) is a targeted vector for creating GOI (eGFP) producing cell lines in the CHOK1SV GS-KO™ SSI host. Transcription of eGFP is driven by the promoter of the hCMV major intermediate early gene 1 (hCMV) and uses a β-globin polyadenylation (pA) sequence. The entire transcription cassette is flanked by inverted terminal repeats (ITR) which are the only cis-acting elements necessary for virus replication and encapsulation. Neomycin phosphotransferase I (nptI) gene is arranged immediately to the 3' of Frt14 and successful RMCE transcription in driven by SV40E promoter located in the landing pad in the NL1 loci. pLMC32 to 35 (FIG. 10B to E) are targeting vectors containing Rep-Cap expression cassettes with different conformations of the AAV p5 promoter for creating AAV Rep-Cap producing cell lines in the CHOK1SV GS-KO™ SSI host (FIG. 10B to E). Normal Rep78 expression driven by the wild-type p5 promoter was shown to inhibit AAV production. The aim of the different conformations is to reduce Rep78 expression, while maintaining Cap expression to maximize AAV production. The glutamine synthetase (GS) cDNA is arranged immediately to the 3' of Frt5 and successful RMCE transcription is driven by SV40E promoter located in the landing pad in the Fer1L4 locus. pLMC32 (FIG. 10B) contains the minimal p5 (white square) with two of the enhancer elements removed. The full p5 (black and white square) is located in 3' of Cap gene to enhance Cap expression. pLMC33 (FIG. 10C) also has the minimal p5 promoter (white square) (similar to pLMC32) but the p5$^{mut}$ promoter (black and grey square) at the 3' of the Cap gene contains a mutated (GGGGGGG) TATA box. In pLMC34 (FIG. 10D) contains the p5 promoter (black and white square) 5' to Rep, and a p5$^{mut}$ promoter (black and grey square) with the TATA box mutated to GGGGGGG was located 3' end of Cap. pLMC35 (FIG. 10E) has the TATA mutation in both p5 promoters (black and grey square). pLMC32-35 use the GS cDNA selection marker.

Figure 11:
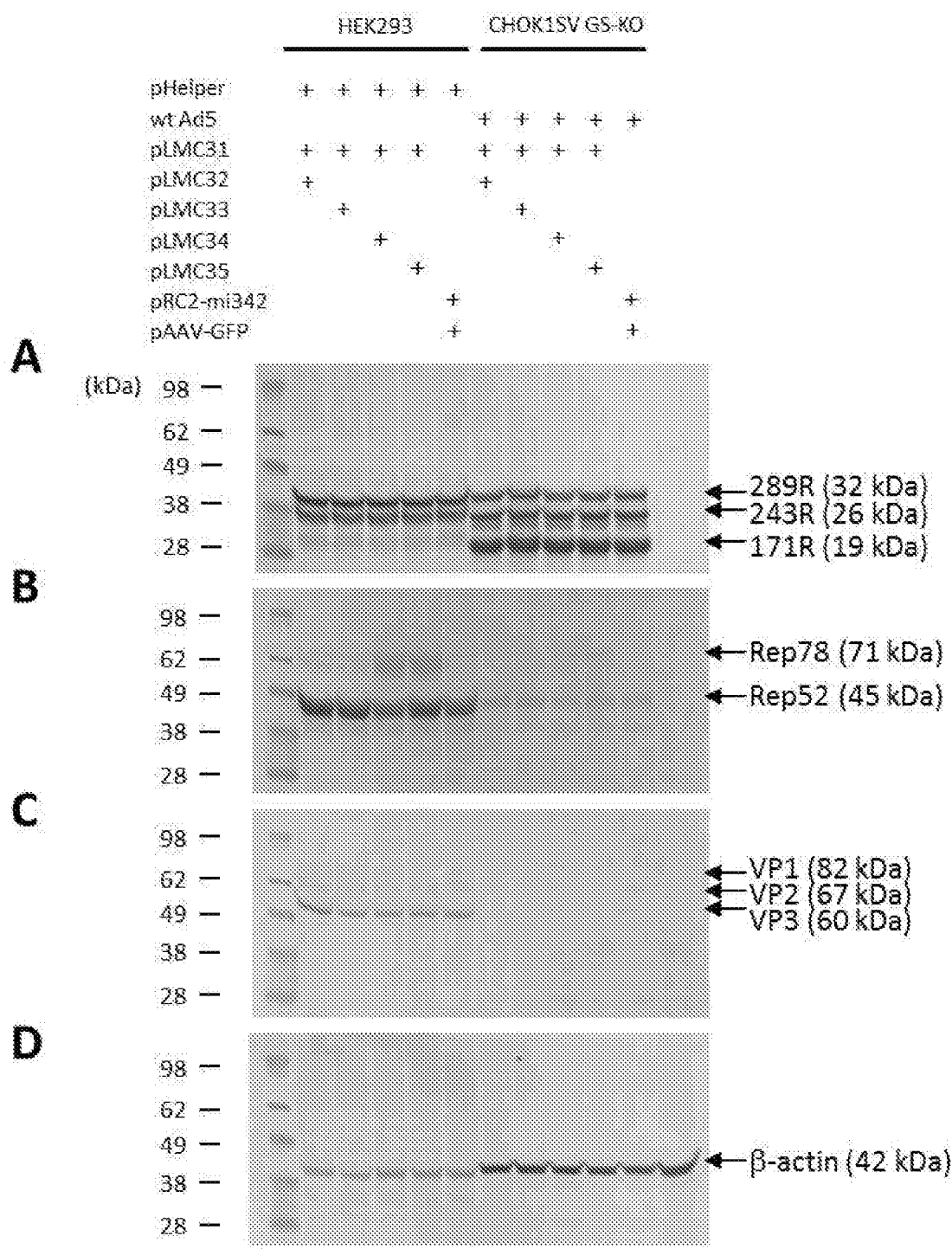
FIG. 11 shows protein expression of E1A, Rep and Cap in HEK293 and CHOK1SV GS-KO™ cells by western blot analysis. HEK293 cells were transfected with pHelper (6234, Clontech), GOI (pLMC31) and one Rep-Cap vector (pLMC32-35) or triple transfected with pHelper (6234, Clontech), pRC2-mi342 (6234, Clontech) and pAAV-GFP (AAV-400, Cell Biolabs). CHOK1SV GS-KO™ cells were infected with wt Ad5 and transfected with GOI (pLMC31) and one Rep-Cap vector (pLMC32-35) or infected with wt Ad5 and transfected with pRC2-mi342 (6234, Clontech) and pAAV-GFP (AAV-400, Cell Biolabs). Three days post transfection, the protein lysates were analysed by western blotting.
Figure 12:
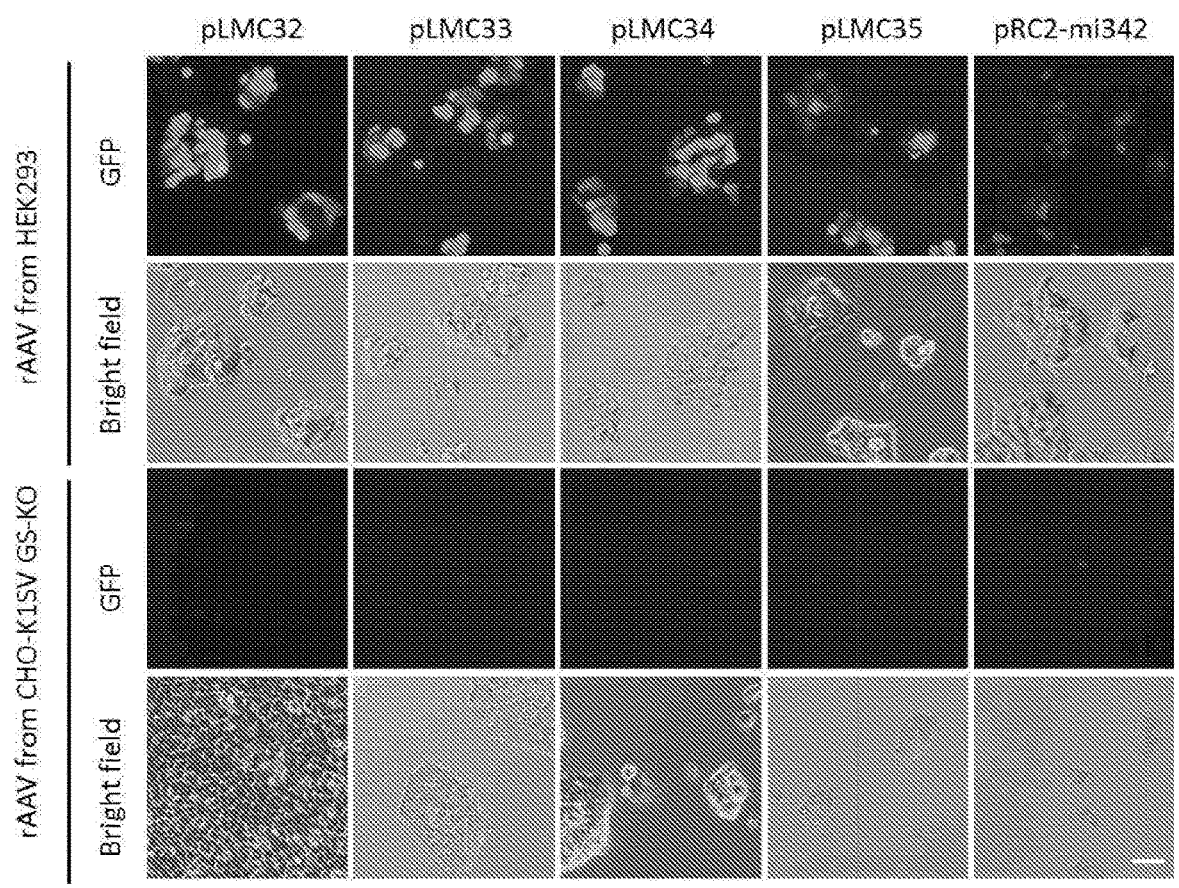
FIG. 12 shows the infectivity of rAAV produced by HEK293 and CHOK1SV GS-KO™ cells. HEK293 cells were triple transfected with Rep/Cap, GOI and pHelper (6234, Clontech). CHOK1SV GS-KO™ cells were transfected with Rep/Cap and GOI, and infected with wt Ad5. Three days post transfection, an equal volume of crude rAAV harvest was used to infect HEK293 cells. Two days post transduction, green fluorescence and bright field images were acquired. Green fluorescence is produced by the GOI-packaged rAAV. The scale bar presented represents 50 µm. The infectivity of rAAV produced by triple transfected HEK293 cells (pHelper (6234, Clontech), pRC2-mi342 (6234, Clontech), pAAV-GFP (AAV-400, Cell Biolabs)) (top panel) was higher than rAAV produced by transfected CHOK1SV GS-KO™ cells (third panel). Of note, the infectivity of rAAV produced by HEK293 cells transfected with pLMC32-35 was higher than HEK293 cells transfected with pRC2-mi342 (6234, Clontech) (top panel).

Section 3: Production of rAAV in CHOK1SV GS-KO™ and HEK293 Cells by Triple Transfection with Four Rep-Cap Configurations The ability of GOI (pLMC31) and Rep-Cap (pLMC32 to 35) expression vectors to support rAAV production in CHOK1SV GS-KO™ co-infected with wt Ad5 virus or HEK293 co-transfected with pHelper (6234, Clontech) vector. Western blot analysis confirmed the transduction of wt Ad5 in CHOK1SV GS-KO™ cells by E1A protein expression (FIG. 11A), and revealed the high level of Rep and Cap protein expression with pLMC31-35 vectors in HEK293 cells, low level of Rep protein expression and Cap protein was not detectable in CHOK1SV GS-KO™ cells (FIGS. 11B and 11C). TaqMan-qPCR analysis showed 3-5 fold increased AAV titer with these pLMC32-35 vectors compared to original plasmids from Clontech (5 #, pRC2-mi342 (6234, Clontech) and pAAV-GFP) in HEK293 cells, while the production was lower in CHOK1SV GS-KO™ cells (FIG. 20). The infectivity assay confirmed the qPCR titer, showing a high level of virus transduction for HEK293 samples and low-level infection for CHOK1SV GS-KO™ samples (FIG. 12). In summary, these data validated the functionality of pLMC32-35 vectors for AAV production in HEK293 and CHO cells, suggesting that they are capable of rAAV production in CHO cells once stably expressed.

Section 4: Generation of CHO Cells with Stable Expression of Rep-Cap and GOI by Site Specific Integration (SSI).

Figure 13:
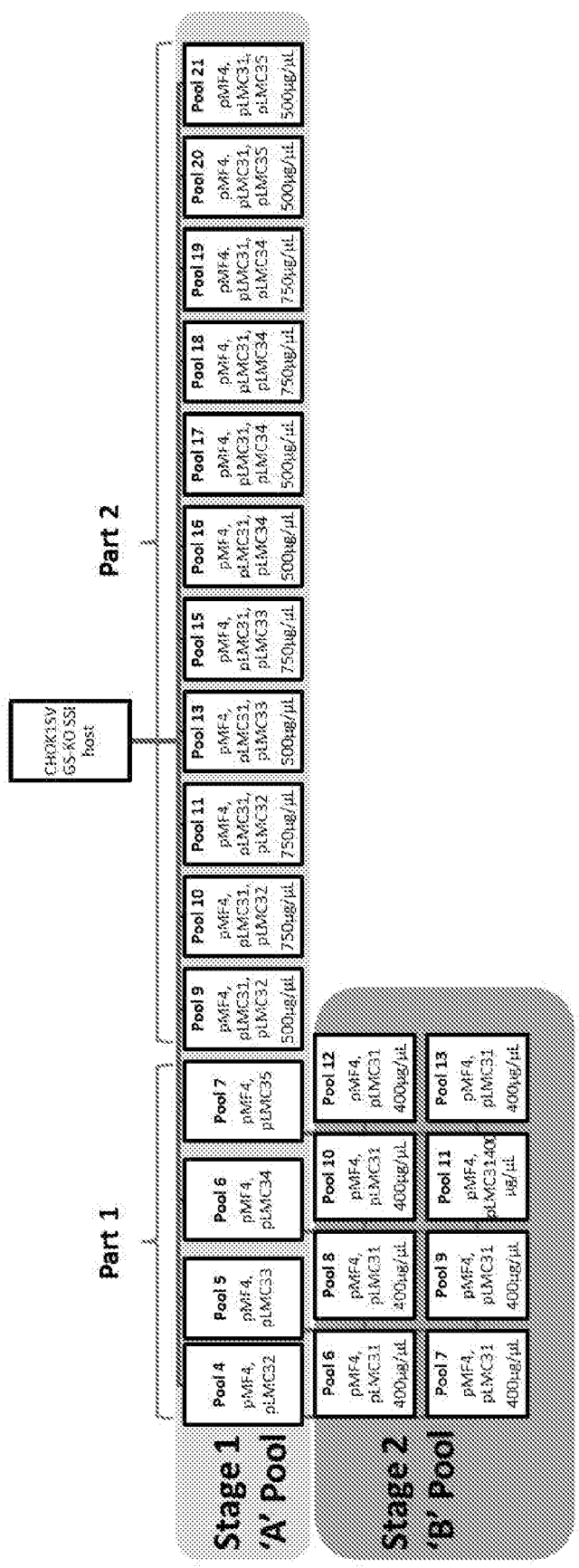
FIG. 13 shows construction of CHOK1SV GS-KO™ SSI host derived pools with SSI of GOI and one of the four Rep-Cap configurations. Pools were generated in two stages. In stage 1 part 1, the CHOK1SV GS-KO™ SSI host was transfected with FLP recombinase vector (pMF4) and one Rep-Cap vector (pLMC32-35) and then selected in glutamine-free media. In stage 1 part 2, the CHOK1SV GS-KO™ SSI host was transfected with FLP recombinase vector (pMF4), one Rep-Cap vector (pLMC32-35) and GOI vector (pLMC31), and then selected in glutamine-free media containing Geneticin (500 µg/mL or 750 µg/mL). These became 'A' Pools. In stage 2, 'A' Pools 4-7 were transfected with FLP recombinase (pMF4) and GOI vector (pLMC31), and then selected in media containing Geneticin (400 µg/mL). These became 'B' Pools.
Figure 14:
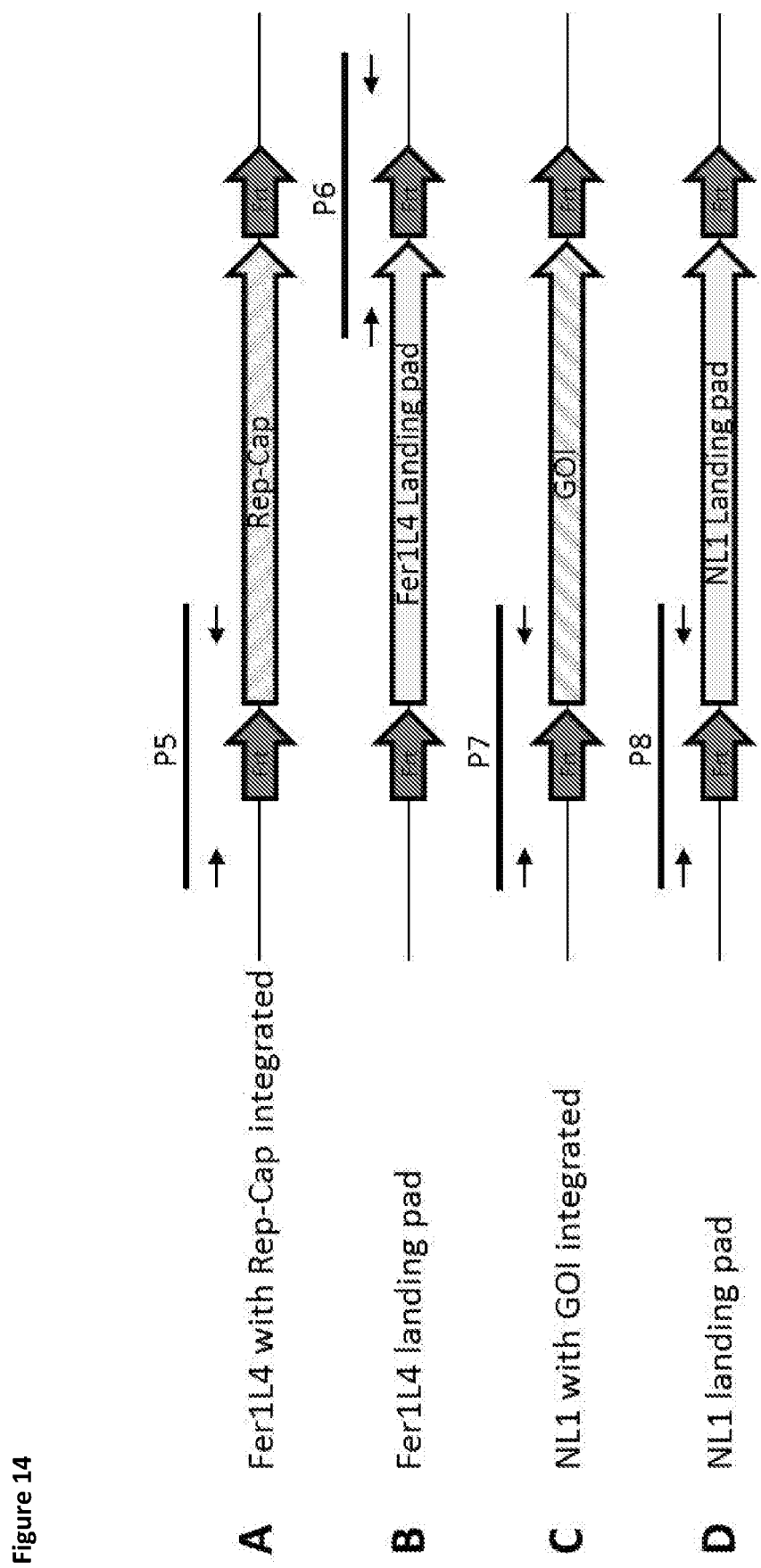
FIG. 14 shows a schematic of primer locations for detection of on-target SSI and residual (non-exchanged) landing pad. Primer set P5 was designed for detecting specific Rep/Cap integration into a landing pad located in the Fer1L4 gene. The expected product size is 1524 bp. Primer set P6 was designed for detecting residual landing pad. The expected product size is 487 bp. Primer set P7 was designed for detecting specific GOI integration into a landing pad located in the NL1 locus. The expected product size is 1446 bp. Primer set P8 was designed for detecting residual NL1 landing pad. The expected product size is 809 bp.
Figure 15:
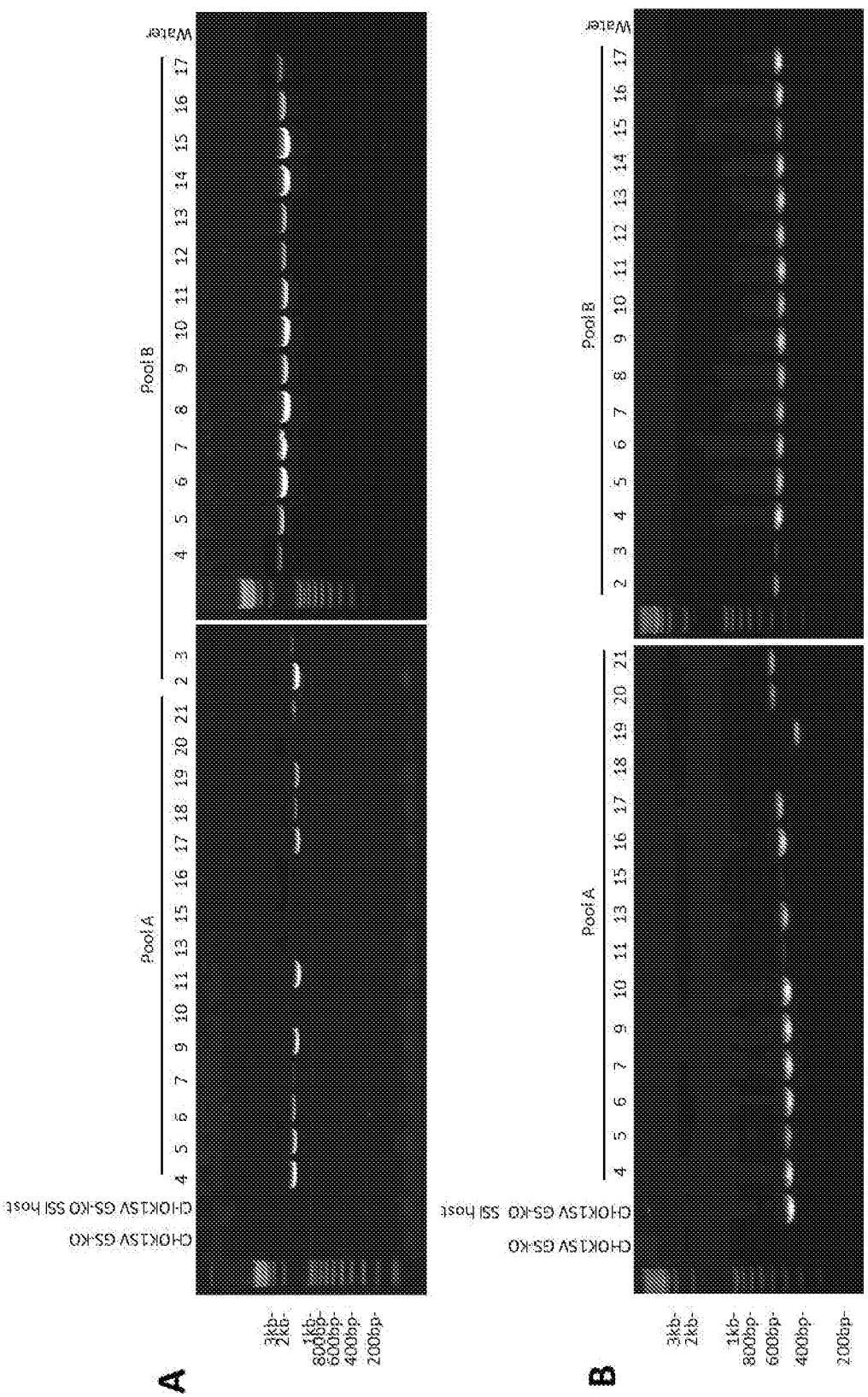
FIG. 15 shows agarose gel analysis of genomic DNA PCR products for Rep/Cap integration into the Fer1L4 landing pad. Genomic DNA was harvested from 'A' Pools, 'B' Pools, CHOK1SV GS-KO™ and CHOK1SV GS-KO™ SSI host, and then amplified using primer set 5 or 6 by PCR. PCR products were resolved by agarose gel electrophoresis.
Figure 16:
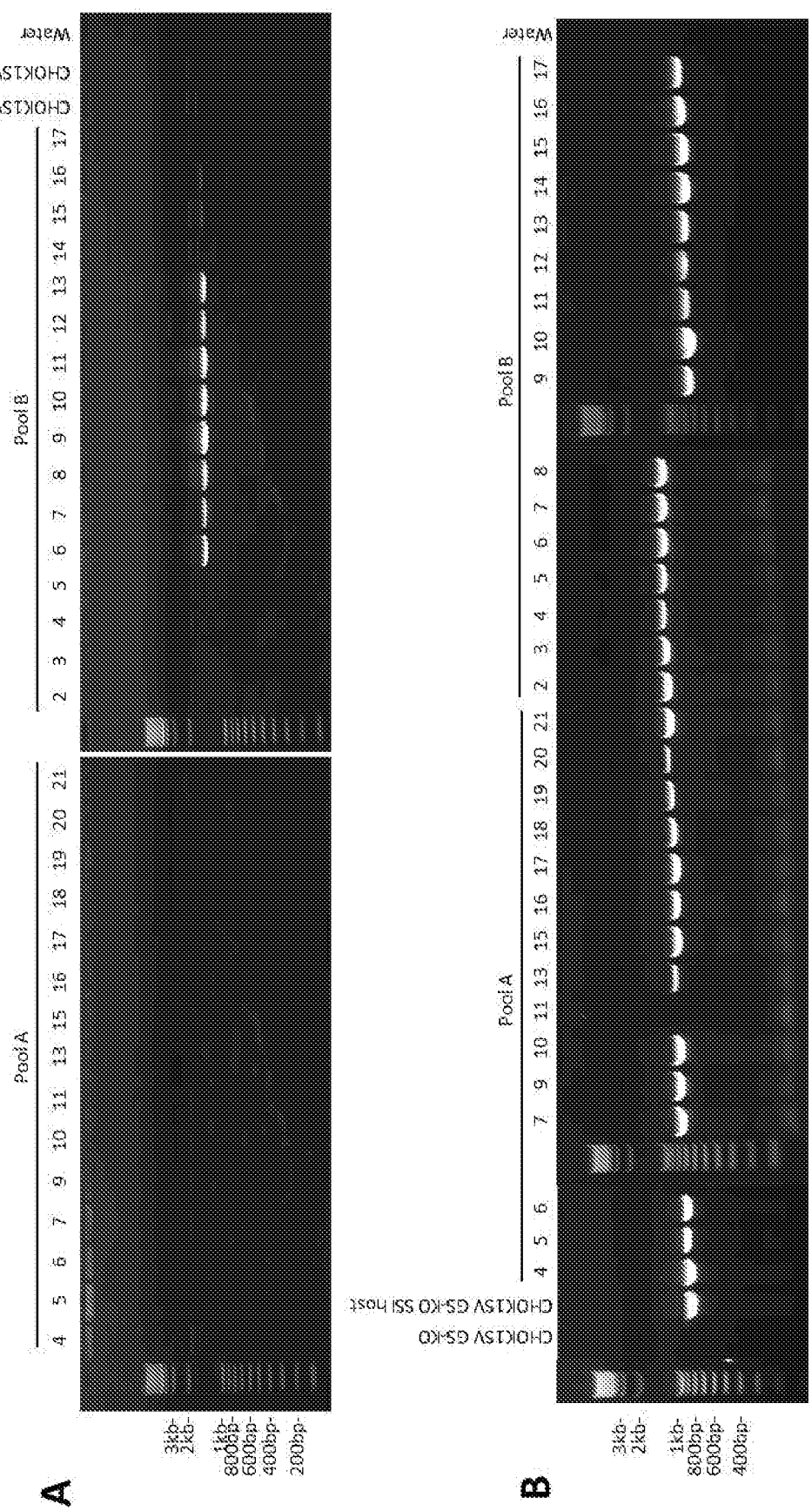
FIG. 16 shows agarose gel analysis of genomic DNA PCR products for GOI integration into the NL1 landing pad. Genomic DNA was harvested from 'A' Pools, 'B' Pools, CHOK1SV GS-KO™ and CHOK1SV GS-KO™ SSI host, and then amplified using primer set 7 or 8 by PCR. PCR products were resolved by agarose gel electrophoresis.
Figure 17:
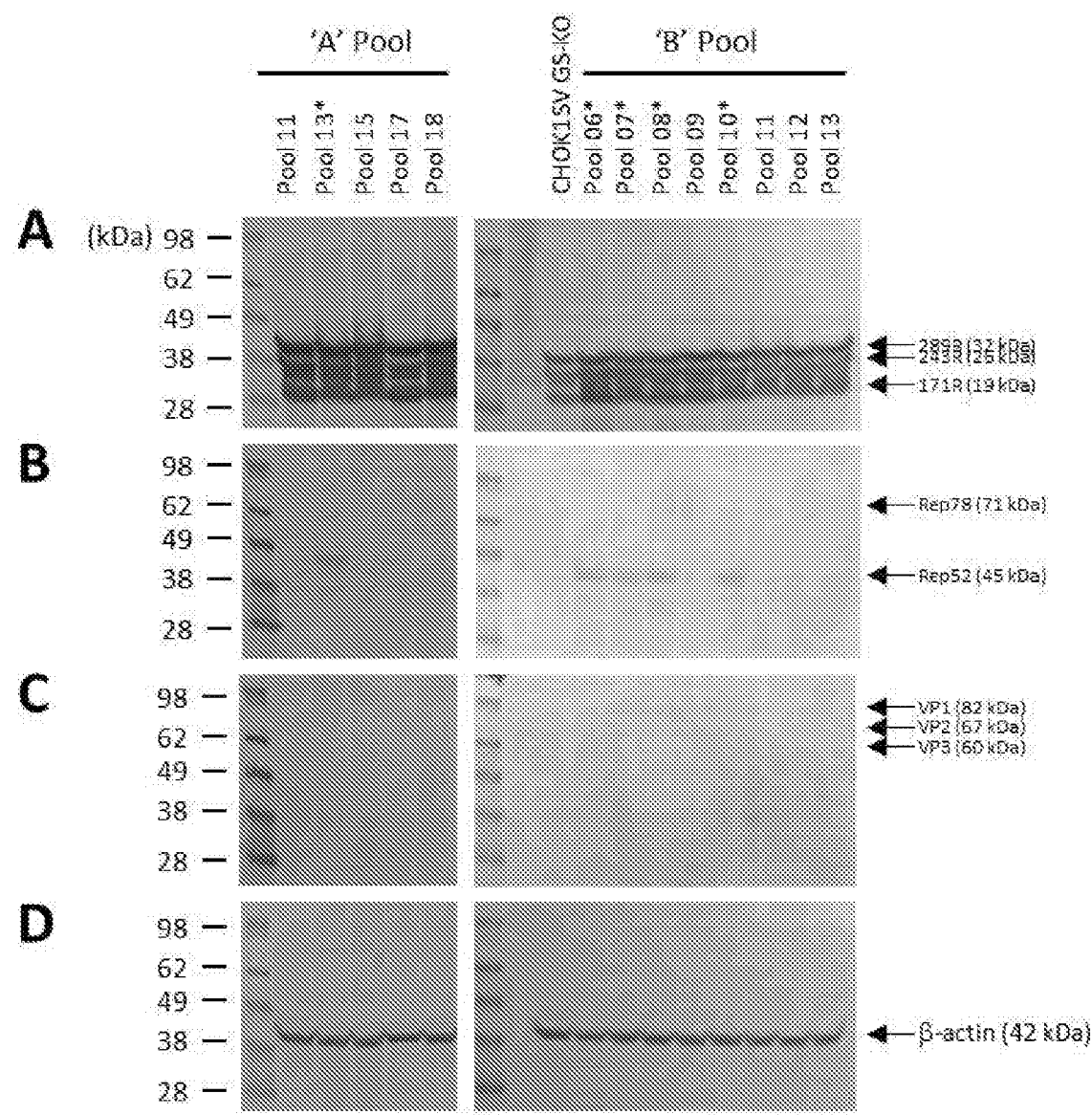
FIG. 17 shows protein expression of E A, Rep and Cap in wt Ad5 infected CHOK1SV GS-KO™ cells by western blot analysis. 'A' Pools and 'B' Pools were infected with wt Ad5 for three days, and then harvested for E1A, Rep, Cap and beta-actin protein expression analysis.
Figure 18:
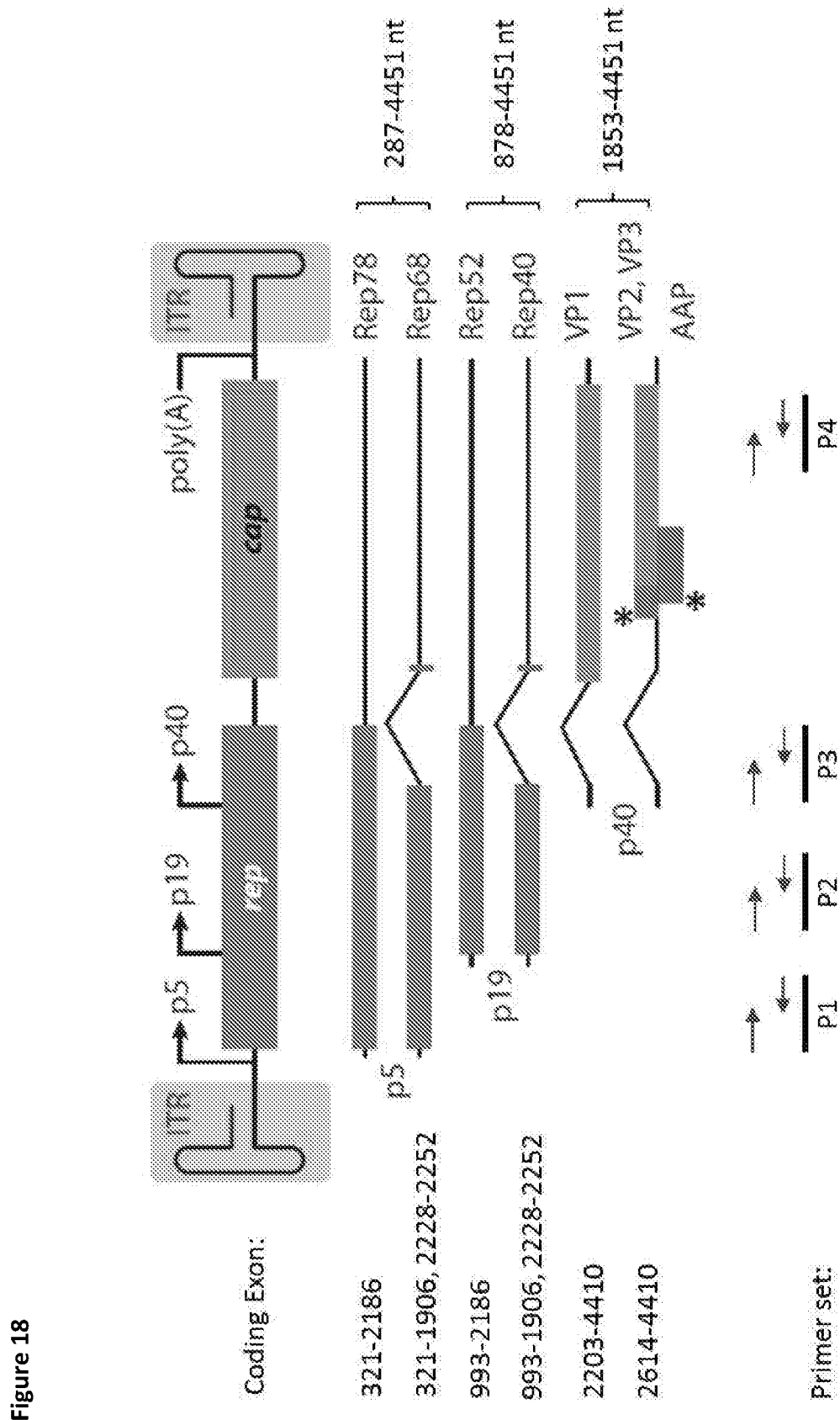
FIG. 18 shows a schematic of primer locations for detection of AAV2 Rep and Cap mRNA. Primer set P1 for Rep78 and Rep68. Primer set P2 for Rep78, Rep68, Rep52, and Rep40. Primer set P3 for Rep78 and Rep52. Primer set P4 for total Rep and Cap. * indicates the alternative ACG codon used to produce VP3. AAV2 genome structure was adapted from Samulski and Muzyczka, *Annu. Rev. Virol.* 1:427-451 (2014).
Figure 19:
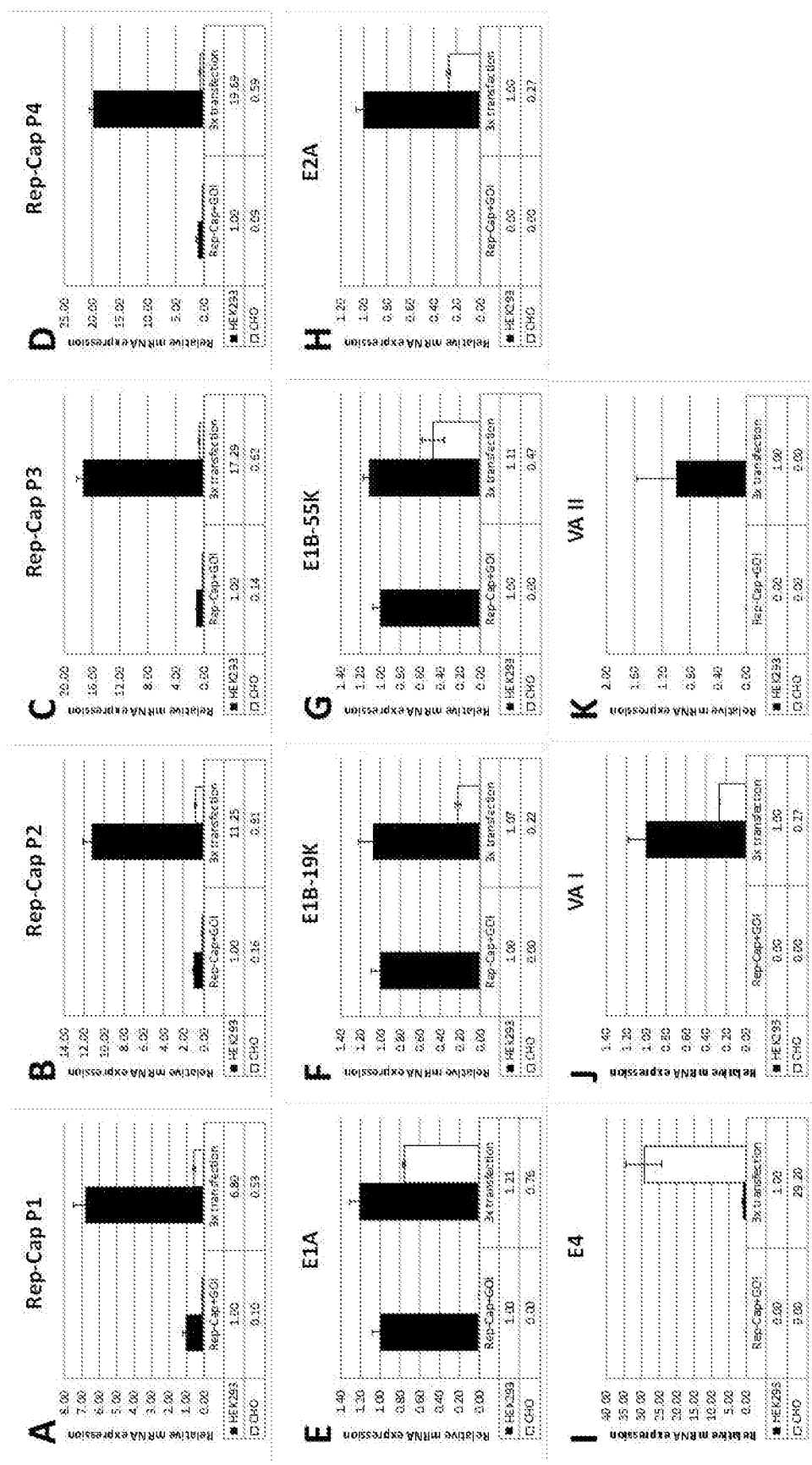
FIG. 19 shows mRNA expression analysis on Rep-Cap genes and Ad5 helper genes from transfected HEK293 and CHOK1SV GS-KO™ cells. HEK293 cells were triple transfected with pRC2-mi342 (6234, Clontech), pAAV-GFP (AAV-400, Cell Biolabs) vectors (black bars). CHOK1SV GS-KO™ cells were transfected with pRC2-mi342 and pAAV-GFP, and infected with wt Ad5 (white bars). Controls include HEK293 or CHOK1SV GS-KO™ cells transfected with pRC2-mi342 (bars on the left). cDNA was prepared for RT-qPCR analysis for Rep/Cap and Ad helper genes. Expression data was internally normalized with beta-actin and then compared to the HEK293 control sample. Primer sequences are included in FIG. 21.

To determine whether the CHOK1SV GS-KO™ SSI host with stable integration of GOI and Rep/Cap can support rAAV production, the GOI (pLMC31) and each of the Rep-Cap vectors (pLMC32-35) were transfected with FLP recombinase-expressing vector (pMF4) into the CHOK1SV GS-KO™ SSI host. Two sets of pools were generated by simultaneous or sequential integration of Rep-Cap and GOI (FIG. 13). PCR analysis using primers designed to anneal to either Rep-Cap, Fer1L landing pad, GOI or NL1 landing pad (FIG. 14) showed successful integration of Rep/Cap into a landing pad located in the Fer1L4 gene in the majority of pools (FIG. 15A). PCR products of residual Fer1L4A landing pad was detected in all, except two of the pools ('A' Pools 18 and 19), indicating complete SSI in these pools (FIG. 15B). However, GOI was only integrated into a landing pad located in the NL1 locus of pools generated by targeting sequentially ('B' Pools) (FIG. 16A), and residual landing pad was detected in all of the Pools (FIG. 16B). Western blot analysis identified five pools with stable expression of Rep, while Cap protein expression was undetectable (FIG. 17). To substantiate the Rep-Cap expression in CHOK1SV GS-KO™ cells, mRNA expression of these genes was analyzed by TaqMan-qPCR assay, using the primers for detecting different isoforms of Rep and Cap (FIG. 18 and FIG. 21). Transfection of CHOK1SV GS-KO™ cells with Rep-Cap2, GOI and pHelper (6234, Clontech) vectors induced ~5-fold higher Rep mRNA levels (FIG. 19A-C), and ~7-fold for Rep and Cap mRNA levels (FIG. 19D) in comparison with GOI (pLMC31) and Rep-Cap (pLMC32-35) vectors (FIG. 19A-C). E1A, E1B, E2A, E4 and VA I mRNA levels were only detectable when CHOK1SV GS-KO™ cells were transfected with Rep-Cap2, GOI and pHelper (6234, Clontech), and not when transfected with GOI (pLMC31) and Rep-Cap (pLMC32-35) (FIG. 19E-J). VA II mRNA levels were not detectable in CHOK1SV GS-KO™ cells (FIG. 19K). All of the observed mRNA levels, except E4 were lower in CHOK1SV GS-KO™ in comparison with HEK293 cells (FIG. 19A-K). These data show that the Rep-Cap mRNA induction and expression were lower in CHOK1SV GS-KO™ cells in comparison with HEK293 cells. In summary, CHOK1SV GS-KO™ cells can express Ad5 helper genes and Rep-Cap, but the expression levels of these genes need to be further optimized.

SEQUENCE LISTING

The patent contains a lengthy sequence listing. A copy of the sequence listing is available in electronic form from the USPTO web site (https://seqdata.uspto.gov/?pageRequest=docDetail&DocID=US11781116B2). An electronic copy of the sequence listing will also be available from the USPTO upon request and payment of the fee set forth in 37 CFR 1.19(b)(3).

What is claimed is:

1. A CHOK1SV glutamine synthetase knock-out cell comprising (i) at least four distinct recombination target sites (RTS), (ii) an adenovirus (Ad) gene comprising E1A, E1B or a combination thereof, and (iii) a promoter operatively linked to the Ad gene, wherein the RTS, the Ad gene, and the promoter are chromosomally-integrated, at least one RTS, the Ad gene, and the promoter are integrated at a single chromosomal locus, the chromosomal locus is Fer1L4, ROSA26, HGPRT, DHFR, COSMC, LDHa, MGAT1, GRIK1, NL1, NL2, the first intron of MID1 on the X chromosome, or Enhanced Expression and stability regions, wherein the CHOK1SV glutamine synthetase knock-out cell is a Chinese hamster ovary cell adapted for growth in suspension and serum-free medium and having glutamine synthetase gene knockout, and wherein the CHOK1SV glutamine synthetase knock-out cell comprising (i), (ii) and (iii) expresses E1A mRNA and E1B in an amount sufficient to produce adeno-associated virus (AAV).

2. The cell of claim 1, wherein the cell comprises four RTS.

3. The cell of claim 1, wherein the cell comprises six RTS.

4. The cell of claim 1, wherein at least one RTS is selected from the group consisting of SEQ ID NOs.: 1-30.

5. The cell of claim 1, further comprising a site-specific recombinase gene.

6. The cell of claim 1, further comprising a second Ad gene, wherein the second Ad gene is chromosomally-integrated.

7. The cell of claim 6, wherein the second Ad gene is located between two of the RTS.

8. The cell of claim 1, further comprising an adeno-associated virus (AAV) gene, wherein the AAV gene is chromosomally-integrated.

9. The cell of claim 8, wherein the AAV gene is located between two of the RTS.

10. The cell of claim 1, further comprising an AAV vector cassette, wherein the AAV vector cassette is chromosomally-integrated.

11. The cell of claim 10 wherein the AAV vector cassette comprises a reporter gene, a selection gene, a gene of therapeutic interest, or a combination thereof.

12. The cell of claim 1, wherein the cell is substantially free of helper virus.

* * * * *